United States Patent
Bryce et al.

(10) Patent No.: US 11,723,974 B2
(45) Date of Patent: Aug. 15, 2023

(54) METHODS FOR TREATING DIGITALLY IDENTIFIED IL-4/IL-13-RELATED DISORDERS BY ADMINISTERING AN ANTI-IL4R-ALPHA ANTIBODY

(71) Applicant: Sanofi Biotechnology, Paris (FR)

(72) Inventors: Paul Bryce, Bridgewater, NJ (US); Emanuele De Rinaldis, Bridgewater, NJ (US); Ramon Antonio Hernandez Vecino, Paris (FR); Francisco Javier Jimenez Jimenez, Brookline, MA (US); Cliona Marie Molony, Bridgewater, NJ (US)

(73) Assignee: Sanofi-Aventis Biotechnology, Paris (FR)

( * ) Notice: Subject to any disclaimer, the term of this patent is extended or adjusted under 35 U.S.C. 154(b) by 0 days.

(21) Appl. No.: 17/115,618

(22) Filed: Dec. 8, 2020

(65) Prior Publication Data

US 2021/0220470 A1     Jul. 22, 2021

Related U.S. Application Data

(60) Provisional application No. 63/028,919, filed on May 22, 2020, provisional application No. 62/945,807, filed on Dec. 9, 2019.

(30) Foreign Application Priority Data

Nov. 2, 2020 (EP) .................................. 20315281
Nov. 13, 2020 (EP) .................................. 20315450

(51) Int. Cl.

| | | |
|---|---|---|
| A61K 39/395 | (2006.01) | |
| A61K 9/00 | (2006.01) | |
| A61K 45/06 | (2006.01) | |
| C07K 16/28 | (2006.01) | |
| G06N 20/00 | (2019.01) | |
| A61K 31/137 | (2006.01) | |
| A61K 31/522 | (2006.01) | |
| A61K 31/56 | (2006.01) | |
| A61K 31/573 | (2006.01) | |
| A61K 39/00 | (2006.01) | |

(52) U.S. Cl.
CPC ........ *A61K 39/3955* (2013.01); *A61K 9/0019* (2013.01); *A61K 31/137* (2013.01); *A61K 31/522* (2013.01); *A61K 31/56* (2013.01); *A61K 31/573* (2013.01); *A61K 45/06* (2013.01); *C07K 16/2866* (2013.01); *G06N 20/00* (2019.01); *A61K 2039/545* (2013.01); *C07K 2317/565* (2013.01)

(58) Field of Classification Search
CPC .............. A61K 39/3955; A61K 9/0019; A61K 31/137; A61K 31/522; A61K 31/56; A61K 31/573; A61K 45/06; A61K 2039/545; C07K 16/2866; C07K 2317/565

See application file for complete search history.

(56) References Cited

U.S. PATENT DOCUMENTS

| | | |
|---|---|---|
| 5,545,807 A | 8/1996 | Sumni et al. |
| 6,596,541 B2 | 7/2003 | Murphy et al. |
| 6,787,637 B1 | 9/2004 | Schenk |
| 7,186,809 B2 | 3/2007 | Pluenneke |
| 7,605,237 B2 | 10/2009 | Stevens et al. |
| 7,608,693 B2 | 10/2009 | Martin et al. |
| 8,092,804 B2 | 1/2012 | Eriksson et al. |
| 8,945,559 B2 | 2/2015 | Dix et al. |
| 9,290,574 B2 | 3/2016 | Kostic et al. |
| 9,574,004 B2 | 2/2017 | Ardeleanu et al. |
| 10,059,771 B2 | 8/2018 | Mannent et al. |
| 10,066,017 B2 * | 9/2018 | Mannent ............ A61K 39/3955 |
| 10,137,193 B2 * | 11/2018 | Pirozzi ............... C07K 16/2866 |
| 10,314,904 B2 | 6/2019 | Purcell et al. |
| 10,370,449 B2 | 8/2019 | Graham et al. |
| 10,392,439 B2 | 8/2019 | Stahl et al. |
| 2016/0185866 A1 | 6/2016 | Mannent et al. |
| 2017/0333557 A1 | 11/2017 | Ardeleanu et al. |
| 2018/0078603 A1 | 3/2018 | Radin et al. |
| 2019/0040126 A1 | 2/2019 | Radin et al. |
| 2019/0183904 A1 | 6/2019 | Ghosh et al. |

FOREIGN PATENT DOCUMENTS

| | | |
|---|---|---|
| WO | WO 2014/197470 | 12/2014 |
| WO | WO 2014/205365 | 12/2014 |
| WO | WO 2015/006571 | 1/2015 |
| WO | WO 2015/130975 | 9/2015 |
| WO | WO 2016/077675 | 5/2016 |
| WO | WO 2018/045130 | 3/2018 |
| WO | WO 2019/089473 | 5/2019 |

OTHER PUBLICATIONS

Goldminz AM and Scheinman PL (Nov. 2018) Dermatol Ther. 31(6):e12701. (doi: 10.1111/dth.12701. Epub Sep. 24, 2018).*
Weston GK, et al. (Mar. 1, 2018) J Drugs Dermatol. 17(3):355-356.*
Oosterhaven JAF, et al. (Aug. 2019) J Dermatol. 46(8):680-685. (doi:10.1111/1346-8138.14982. Epub Jun. 12, 2019).*
Lee JK and Simpson RS (May-Jun. 2019) J Allergy Clin Immunol Pract. 7(5):1659-1661.e1. (doi:10.1016/j.jaip.2018.11.018. Epub Nov. 27, 2018).*
Fleming P and Drucker AM (Jan. 2018) J Am Acad Dermatol. 78(1):62-69. (doi.org/10.1016/j.jaad.2017.09.052).*
Gasparini G, et al. (Jan. 2020) Cytokine. 125:154799. (doi:10.1016/j.cyto.2019.154799. Epub Aug. 7, 2019).*
<Span style="font-family: "Windows Arial Unicode";">Rial MJ, et al. (Feb. 2019) </span><span style="font-family: "Windows Arial Unicode";">J Allergy Clin Immunol Pract. 7(2):673-674. (doi:10.1016/j.jaip.2018.07.027. Epub Aug. 1, 2018)</span>.*

(Continued)

*Primary Examiner* — Robert S Landsman
(74) *Attorney, Agent, or Firm* — Fish & Richardson P.C.

(57) ABSTRACT

Disclosed are methods of treating various disorders with anti-IL-4Rα antibodies and fragments thereof.

48 Claims, 14 Drawing Sheets

Specification includes a Sequence Listing.

(56) References Cited

OTHER PUBLICATIONS

<Span style="font-family: "Windows Arial Unicode";">https://clinicaltrials.gov/ct2/show/NCT04148352 (Andrew Long, sponsor)</span>.*
<Span style="font-family: "Windows Arial Unicode";">Willsmore ZN et al. (Nov. 2018) </span><span style="font-family: "Windows Arial Unicode";">Br J Dermatol. 181(5):1068-1070. (doi:10.1111/bjd.18031. Epub Jul. 18, 2019)</span>.*
<Span style="font-family: "Windows Arial Unicode";">Chu C-Y (2019) </span><span style="font-family: "Windows Arial Unicode";">British Journal of Dermatology. 181:436-437. </span><span style="font-family: "Windows Arial Unicode";">(doi</span><span style="font-family: "Windows Arial Unicode";">:10.1111/bjd.18255)</s.*
Rial MJ, et al. (Feb. 2019) J Allergy Clin Immunol Pract. 7(2):673-674. (doi:10.1016/j.aip.2018.07.027. Epub Aug. 1, 2018).*
https://clinicaltrials.giv/ct2/show/NCT04148352.*
Willsmore ZN, et al. (Nov. 2018) Br J Dermatol. 181(5):1068-1070. (doi:10.1111/bjd.18031. Epub Jul. 18, 2019).*
Chu C-Y (2019) British Journal of Dermatology. 181:436-437. (doi.10.1111/bjd.18255).*
PCT International Search Report and Written Opinion in International Application No. PCT/US2020/063835, dated May 12, 2021, 23 pages.
Agarwal et al., "Severe asthma and fungi: current evidence", Medical Mycology, Apr. 2011, 49(Suppl. 1): S150-S157.
Bird et al., "Single-chain antigen-binding proteins", Science, Oct. 1988, 242:423-426.
Cho et al., ""Chronic Rhinosinusitis without Nasal Polyps"", The Journal of Allergy and Clinical Immunology: In Practice, Jul. 2016, 4(4):575-582 575-582.
Corren et al., ""A Randomized, Controlled, Phase 2 Study of AMG 317, an IL-4Ra Antagonist, in Patients with Asthma"", American Journal of Respiratory and Critical Care Medicine, 2010, 181(8):788-796.
Demehri et al., "Chronic allergic contact dermatitis promotes skin cancer", The Journal of Clinical Investigation, Nov. 2014,124(11): 5037-5041.
Denning et al., "Fungal allergy in asthma—state of the art and research needs", Clinical and Translational Allergy, 2014, 23 pages.
Glass et al., "Allergic fungal rhinosinusitis: a review", The Ochsner Journal, 2011, 11(3): 271-275.
Global Initiative for Asthma, "Global Strategy for Asthma Management and Prevention", 2009, 112 pages.
Green et al., "Antigen-specific human monoclonal antibodies from mice engineered with human Ig heavy and light chain YACs", Nature Genetics, May 1994, 7:13-21.
Holliger et al., ""Diabodies": small bivalent and bispecific antibody fragments", Proceedings of the National Academy of Sciences USA, Jul. 1993, 90:6444-6448.
Hulse et al., "Pathogenesis of nasal polyposis", Clinical and Experimental Allergy, Feb. 2015, 45(2): 328-346.
Huston et al., "Protein engineering of antibody binding sties: recovery of specific activity in an anti-digoxin single-chain Fv analogue produced in *Escherichia coli*", Proceedings of the National Academy of Sciences USA, Aug. 1988, 85:5879-5883.
Kazane et al., "Self-Assembled Antibody Multimers through Peptide Nucleic Acid Conjugation", Journal of the American Chemical Society, 2013, 135(1) 340-346.
Kim et al., "Engineering of anti-human interleukin-4 receptor alpha antibodies with potent antagonistic activity", Scientific Reports, May 2019, 9(1):7772.
Klein et al., "Progress in overcoming the chain association issue in bispecific heterodimeric IgG antibodies", mAbs, Aug. 2012, 4(6) 653-663.
Langer, "New methods of drug delivery", Science, Sep. 1990, 249:1527-1533.
MedImmune LLC, "Safety and Tolerability of MEDI9314 as Single Ascending Dose in Healthy Subjects", U.S. National Library of Medicine, Feb. 2016, 10 pages.
National Heart, Lung and Blood Institute, "Expert Panel Report 3: Guidelines for the Diagnosis and Management of Asthma," U.S. Department of Health and Human Services, Aug. 2007, 440 pages.
Needleman et al., "A general method applicable to the search for similarities in the amino acid sequence of two proteins", Journal of Molecular Biology, Mar. 1970, 48:444-453.
Stevens et al., "Cytokines in Chronic Rhinosinusitis Role in Eosinophilia and Aspirin-exacerbated Respiratory Disease", American Journal of Respiratory and Critical Care Medicine, 2015, 192:682-694.
Taylor et al., "A transgenic mouse that expresses a diversity of human sequence heavy and light chain immunoglobulins", Nucleic Acids Research, Dec. 1992, vol. 20, Issue 23, pp. 6287-6295.
Wang et al., "A Randomized, Double-Blind, Placebo-Controlled, Multiple Ascending Dose Study of the Safety, Pharmacokinetics and Preliminary Efficacy of CBP-201 in Adult Patients with Moderate to Severe Atopic Dermatitis (CBP-201AU002)", 29th EADV Congress, Oct. 2020, 1 page.
Ward et al., "Binding activities of a repertoire of single immunoglobulin variable domains secreted from *Escherichia coli*", Nature, Oct. 1989, 241:544-546.
Wu et al., "Receptor-mediated in vitro gene transformation by a soluble DNA carrier system", The Journal of Biological Chemistiy, Apr. 1987, 262:4429-4432.
Youakim et al., ""Interferon-γ decreases barrier function in T84 cells by reducing ZO-1 levels and disrupting apical actin"", American Journal of Physiology—Gastrointestinal and Liver Physiology, May 1999, 276(5): G1279-G1288.
Zackheim et al., "Prognosis in cutaneous T-cell lymphoma by skin stage: Long-term survival in 489 patients", Journal of American Academy of Dermatology, Mar. 1999, 40(3):418-25.
Langhauser et al., "A diseasome cluster-based drug repurposing of soluble guanylate cyclase activators from smooth muscle relaxation to direct neuroprotection", NPJ Systems Biology and Applications, Feb. 2019, 4(1):1-13.
Optum Humedica, "Optum Integrated Data", Jan. 2014, retrieved on Apr. 14, 2021, retreived from URL <"https://www.optum.com/content/dam/optum/resources/productSheets/5359_NA_All_LS OptumIntegratedDataPS_LR.pdf">, 2 pages.
Pan et al., "Pathway Analysis for Drug Repositioning Based on Public Database Mining", Journal of Chemical Information and Modeling, Feb. 2014, 54(2): 407-418.
PCT Invitation to Pay Additional Fees in International Application No. PCT/US2020/063835, dated Mar. 18, 2021, 19 pages.
International Preliminary Report on Patentability in International Application No. PCT/US2020/063835, dated Jun. 23, 2022, 15 pages.
ClinicalTrials.gov [online], "Treatment of Alopecia Areata (AA) With Dupilumab in Patients With and Without Atopic Dermatitis (AD)," NCT03359356, Nov. 27, 2017, retrieved on Mar. 6, 2023, retrieved from URL <https://clinicaltrials.gov/ct2/history/NCT03359356?V_1=View#StudyPageTop>, 6 pages.
Gandhi et al., "Targeting key proximal drivers of type 2 inflammation in disease," Nature Reviews: Drug Discovery, Jan. 2016, 15:35-50.

* cited by examiner

FIG. 6A

Ranked for Asthma Co-occurrence

| | Feature | ASTHMA_FEATURE | TA |
|---|---|---|---|
| 1 | Upper respiratory tract hyper-sensitivity reaction, site unspecified | 1 | Respiratory |
| 2 | Anaphylaxis | 0.864462142 | Allergy |
| 3 | Other female pelvic inflammatory diseases | 0.817473105 | Other |
| 4 | Chronic diseases of tonsils and adenoids | 0.793869361 | Other |
| 5 | Food allergy | 792945806 | Allergy |
| 6 | Hypertrophy of adenoids | 0.774518783 | Other |
| 7 | Endometriosis | 0.769509079 | Other |
| 8 | Chronic sinusitis | 0.761959091 | Respiratory |
| 9 | Inflammatory disease of cervix uteri | 0.728455217 | Other |
| 10 | Other and unspecified allergy | 0.727873011 | Allergy |
| 11 | Other specified disorders of nose and nasal sinuses | 0.726268239 | Other |
| 12 | Eosinophilic colitis | 0.72115905 | Other |
| 13 | Allergic and dietetic gastroenteritis and colitis | 0.720740392 | Other |
| 14 | Allergic rhinitis | 0.719719858 | Respiratory |
| 15 | Eosinophilic gastritis or gastroenteritis | 0.711833307 | Other |
| 16 | Salpingitis and oophoritis | 0.698437236 | Other |
| 17 | Urticaria | 0.679490875 | Dermatology |
| 18 | Acute lymphadenitis | 0.673085112 | Other |
| 19 | Nonsuppurative otitis media | 0.659319505 | Other |
| 20 | Interstitial cystitis (chronic) | 0.653820624 | Other |
| 21 | Nasal Polyp | 0.651811262 | Respiratory |
| 22 | Carcinoma in situ of cervix uteri | 0.648388781 | Other |
| 23 | Allergic bronchopulmonary aspergillosis | 0.645822918 | Respiratory |
| 24 | Angioneurotic edema, initial encounter | 0.609837713 | Allergy |
| 25 | Chronic tubulo-interstitial nephritis | 0.599334879 | Other |
| 26 | Acute sinusitis | 0.586337514 | Respiratory |
| 27 | Eosinophilia | 0.584140033 | Rheumatology |
| 28 | Allergic rhinitis, unspecified | 0.575895626 | Allergy |
| 29 | Polyarteritis nodosa and related conditions | 0.570982238 | Rheumatology |
| 30 | Hyperimmunoglobulin E [ige] syndrome | 0.557481605 | Other |

FIG. 6B

| | Ranked for Atopic Dermatitis Co-occurrence Feature | ATOPIC_DERM_FEATURE | TA |
|---|---|---|---|
| 1 | Vernal conjunctivitis | 1 | Allergy |
| 2 | Epidermolysis bullosa | 0.985081897 | Dermatology |
| 3 | Eczematous dermatitis of eyelid | 0.948315238 | Dermatology |
| 4 | Allergic dermatitis of eyelid | 0.946629115 | Dermatology |
| 5 | Systemic mastocytosis | 0.931480085 | Other |
| 6 | Hemangioma of skin and subcutaneous tissue | 0.926604621 | Dermatology |
| 7 | Alopecia areata | 0.918583243 | Dermatology |
| 8 | Dyshidrosis [pompholyx] | 0.91545561 | Dermatology |
| 9 | Lichen planus | 0.913353891 | Dermatology |
| 10 | Dermatitis herpetiformis | 0.912361683 | Dermatology |
| 11 | Rosacea | 0.909225547 | Dermatology |
| 12 | Cicatricial alopecia [scarring hair loss] | 0.905192231 | Dermatology |
| 13 | Otosclerosis | 0.904686656 | Other |
| 14 | Severe combined immunodeficiency [scid] with low or normal b-cell numbers | 0.903730167 | Other |
| 15 | Contact dermatitis | 0.902171924 | Dermatology |
| 16 | Melanocytic nevi | 0.893471481 | Dermatology |
| 17 | Granuloma faciale [eosinophilic granuloma of skin] | 0.893101633 | Dermatology |
| 18 | Congenital ichthyosis | 0.88422431 | Dermatology |
| 19 | Localized scleroderma [morphea] | 0.882270949 | Dermatology |
| 20 | Exfoliative dermatitis | 0.879308624 | Dermatology |
| 21 | Other specified dermatitis | 0.873684863 | Dermatology |
| 22 | Nummular dermatitis | 0.873442944 | Dermatology |
| 23 | Eccrine sweat disorders | 0.873267731 | Dermatology |
| 24 | Seborrheic dermatitis | 0.872564945 | Dermatology |
| 25 | Chronic giant papillary conjunctivitis | 0.868152527 | Allergy |
| 26 | Dermatitis, unspecified | 0.86730414 | Dermatology |
| 27 | Scleritis | 0.864621144 | Rheumatology |
| 28 | Solar urticaria | 0.862901447 | Dermatology |
| 29 | Other respiratory conditions due to chemicals, gases, fumes, and vapors | 0.860417485 | Respiratory |
| 30 | Pruritus | 0.859110287 | Dermatology |

FIG. 6C

Ranked for IgE Co-occurrence

| # | Feature | IGE_FEATURE | TA |
|---|---|---|---|
| 1 | Upper respiratory tract hyper-sensitivity reaction, site unspecified | 0.933904208 | Respiratory |
| 2 | Eosinophilis gastritis or gastroenteritis | 0.708874434 | Other |
| 3 | Allergic bronchopulmonary aspergillosis | 0.703403987 | Respiratory |
| 4 | Eosinophilic colitis | 0.68935144 | Other |
| 5 | Polyarteritis nodosa and related conditions | 0.598370952 | Rheumatology |
| 6 | Hyperimmunoglobulin E [ige] syndrome | 0.574693193 | Other |
| 7 | Allergic and dietetic gastroenteritis and colitis | 0.561859385 | Other |
| 8 | Eosinophilia | 0.550967948 | Rheumatology |
| 9 | Stevens-Johnson syndrome | 0.541428937 | Dermatology |
| 10 | Angioneurotic edema, initial encounter | 0.53939303 | Allergy |
| 11 | Other specified systemic involvement of connective tissue | 0.522562307 | Rheumatology |
| 12 | Systemic mastocytosis | 0.520440863 | Other |
| 13 | Pyoderma gangrenosum | 0.519222388 | Dermatology |
| 14 | Severe combined immunodeficiency [scid] with low or normal b-cell numbers | 0.519031831 | Other |
| 15 | Postinfective and reactive anthropathies | 0.517089072 | Rheumatology |
| 16 | Felty's syndrome | 0.508196616 | Rheumatology |
| 17 | Food allergy | 0.499148976 | Allergy |
| 18 | Erythema multiforme | 0.48962171 | Dermatology |
| 19 | Nonsuppurative otitis media | 0.487064117 | Other |
| 20 | Anaphylaxis | 0.48189793 | Allergy |
| 21 | Graft-versus-host disease | 0.471156086 | Rheumatology |
| 22 | Erythema nodosum | 0.478558444 | Dermatology |
| 23 | Adult-onset Still's disease | 0.476041406 | Rheumatology |
| 24 | Other specified disorders involving the immune mechanism, not elsewhere classified | 0.468534299 | Other |
| 25 | Allergic rhinitis | 0.468230373 | Respiratory |
| 26 | Monocytic leukemia | 0.46805967 | Other |
| 27 | Myeloid leukemia | 0.464213847 | Other |
| 28 | Chronic sinusitis | 0.459556621 | Respiratory |
| 29 | Mastoditis and related conditions | 0.451140664 | Other |
| 30 | Extrinsic allergic alveolitis | 0.450501664 | Respiratory |

FIG. 6D

Ranked for Composite Immunology Cluster Score Occurrence

| Feature | IMMUNO_SCORE_FEATURE | Immune | ImmunoScore | TA |
|---|---|---|---|---|
| Upper respiratory tract hyper-sensitivity reaction, site unspecified | 0.574376657 | 0.574377 | 1 | Respiratory |
| Allergic rhinitis | 0.486263226 | 0.644527 | 2 | Allergy |
| Hypertrophy of adenoids | 0.483417089 | 0.614283 | 3 | Other |
| Anaphylaxis | 0.498199572 | 0.568 | 4 | Allergy |
| Nasal Polyp | 0.451905157 | 0.58002 | 5 | Respiratory |
| Eosinophilic esophagitis | 0.476668548 | 0.529558 | 6 | Other |
| Chronic sinusitis | 0.46509598 | 0.523717 | 7 | Respiratory |
| Recurrent and persistent hematuria with other morphological changes | 0.592048867 | 0.422662 | 8 | Other |
| Chronic diseases of tonsils and adenoids | 0.411460552 | 0.526868 | 9 | Other |
| Multiple sclerosis | 0.581383059 | 0.26147 | 10 | Other |
| Other specified disorders of nose and nasal sinuses | 0.383322913 | 0.43337 | 11 | Other |
| Allergic rhinitis, unspecified | 0.361825611 | 0.505788 | 12 | Allergy |
| Nonsuppurative otitis media | 0.365532808 | 0.450616 | 13 | Other |
| Acute sinusitis | 0.320257854 | 0.568892 | 14 | Respiratory |
| Juvenile rheumatoid arthritis | 0.384118127 | 0.334772 | 15 | Rheumatology |
| Allergic bronchopulmonary aspergillosis | 0.389975766 | 0.318916 | 16 | Respiratory |
| Vogt-Koyanagi syndrome | 1 | 0.191662 | 17 | Other |
| Other and unspecified allergy | 0.307194626 | 0.54472 | 18 | Allergy |
| Thyrotoxicosis with diffuse goiter | 0.430592366 | 0.233569 | 19 | Other |
| Pityriasis rosea | 0.303413354 | 0.466931 | 20 | Dermatology |
| Urticaria | 0.310619747 | 0.443451 | 21 | Dermatology |
| Ulcerative colitis | 0.403089254 | 0.237188 | 22 | Other |
| Acute lymphadenitis | 0.297825152 | 0.462151 | 23 | Other |
| Amyotrophic lateral sclerosis | 0.497192749 | 0.156784 | 24 | Other |
| Acne | 0.288946647 | 0.469025 | 25 | Dermatology |
| Malignant neoplasm of breast | 0.420816447 | 0.159188 | 26 | Other |
| Vernal conjunctivitis | 0.259507166 | 0.464618 | 27 | Allergy |
| Autoimmune thyroiditis | 0.280871723 | 0.361903 | 28 | Other |
| Atopic conjunctivitis | 0.234711152 | 0.44732 | 29 | Allergy |
| Chronic rhinitis | 0.520617361 | 0.347822 | 30 | Respiratory |

FIG. 7D

Broader Immunology (combined immuno score and composite rank)
- Upper respiratory tract hyper-sensitivity reaction, site unspecified
- Hypertrophy of adenoids
- Anaphylaxis
- Recurrent and persistent hematuria with other morphological changes
- Chronic diseases of tonsils and adenoids
- Multiple sclerosis
- Other specified disorders of nose and nasal sinuses
- Allergic rhinitis, unspecified
- Nonsuppurative otitis media
- Acute sinusitis
- Juvenile rheumatoid arthritis
- Allergic bronchopulmonary aspergillosis
- Vogt-Koyanagi syndrome
- Other and unspecified allergy
- Thyrotoxicosis with diffuse goiter
- Pityriasis rosea
- Ulcerative colitis
- Acute lymphadenitis
- Amyotrophic lateral sclerosis
- Acne
- Malignant neoplasm of breast
- Vernal conjunctivitis
- Autoimmune thyroiditis
- Chronic nasopharyngitis
- Eosinophilic gastritis or gastroenteritis
- Neuromyelitis optica (Devic)
- Carcinoma in situ of breast
- Malignant neoplasm of prostate
- Allergic and dietetic gastroenteritis and colitis
- Otitis externa

METHODS FOR TREATING DIGITALLY IDENTIFIED IL-4/IL-13-RELATED DISORDERS BY ADMINISTERING AN ANTI-IL4R-ALPHA ANTIBODY

CROSS-REFERENCE TO RELATED APPLICATIONS

This application claims priority and benefit from U.S. Provisional Patent Application No. 62/945,807, filed Dec. 9, 2019, U.S. Provisional Patent Application No. 63/028,919, filed May 22, 2020, European Patent Application No. 20315281.4, filed Nov. 2, 2020, and European Patent Application No. 20315450.5, filed Nov. 13, 2020, the contents and disclosures of which are incorporated herein by reference in their entireties.

REFERENCE TO SEQUENCE LISTING

The instant application contains a Sequence Listing which is hereby incorporated by reference in its entirety. Said file, created on Dec. 1, 2020, is included as a txt file named 37488-0781_Sequence_Listing.txt which is 15.589 kilobytes in size.

TECHNICAL FIELD

The present disclosure relates to treating various disorders with an anti-IL-4R antibody (e.g., an anti-IL-4Rα antibody, e.g., dupilumab).

BACKGROUND

Interleukin-4 (IL-4, also known as B cell stimulating factor or B SF-1) stimulates proliferation of B cells in response to low concentrations of antibodies directed to surface immunoglobulin. IL-4 possesses a broad spectrum of biological activities, including growth stimulation of T cells, mast cells, granulocytes, megakaryocytes and erythrocytes. IL-4 induces the expression of class II major histocompatibility complex molecules in resting B cells, and enhances the secretion of IgE and IgG1 isotypes by stimulated B cells. The biological activities of IL-4 are mediated by specific cell surface receptors for IL-4, i.e., human IL-4 receptor alpha (hIL-4R).

Interleukin-13 (IL-13) as a pleiotropic cytokine acts through the IL-13Ra1/IL-4Rα complex to induce activation responses which contribute to the inflammatory diseases. IL-13 is involved in several stages of B-cell maturation and differentiation; IL-13 up-regulates CD23 and MEW class II expression, and promotes IgE isotype switching of B cells. IL-13 also down-regulates macrophage activity, thereby inhibits the production of pro-inflammatory cytokines and chemokines.

Dupilumab is an anti-IL-4Rα monoclonal antibody that inhibits IL-4 and interleukin-13 (IL-13) signaling. Dupilumab is currently used to treat patients aged 12 years and older with moderate-to-severe atopic dermatitis whose disease is not adequately controlled with topical prescription therapies or when those therapies are not advisable. It is also used as an add-on maintenance treatment in patients with moderate-to-severe asthma and in patients with chronic rhinosinusitis with nasal polyposis. There remains a need to use an anti-IL-4R antibody (e.g., an anti-IL-4Rα antibody, e.g., dupilumab) to treat other disorders.

SUMMARY

The present disclosure is based, at least in part, on the discovery of new disorders treatable with an anti-IL-4Rα antibody, such as dupilumab. Treatable disorders described herein were identified at least initially using a novel computational method capable of analyzing large volumes of patient population data and predicting the therapeutic outcome of treatment using the anti-4Rα antibody.

Therefore, disclosed herein are methods of treating a subject exhibiting at least one symptom of, or determined to be susceptible to, an anti-interleukin-4 receptor alpha (IL-4Rα)-related disorder with an anti-interleukin-4 receptor antibody. In some instances, the methods include administering a therapeutically effective amount of the anti-IL-4Rα antibody to a subject exhibiting at least one symptom of, or determined to be susceptible to, an anti-interleukin-4 receptor alpha (IL-4Rα)-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

In some instances, the methods include (a) identifying a subject for treatment with an anti-IL-4Rα antibody and (b) administering a therapeutically effective amount of the anti-IL-4Rα antibody to the subject, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, identifying the subject for treatment includes (a) selecting a characteristic or a plurality of characteristics in a set of patients; (b) clustering, by a computer system, in accordance with the characteristic or the plurality of characteristics, a subset of patients having the characteristic or the plurality of characteristics, wherein the characteristic or the plurality of characteristics are associated with at least one symptom of, or determined to be susceptible to, the IL-4Rα-related disorder; (c) identifying in the subset of patients clustered in step (b) the IL-4Rα-related disorder based on the symptoms associated with the characteristic or the plurality of characteristics related to the IL-4/IL-13 pathway; and (d) selecting the subject exhibiting at least one symptom of, or determined to be susceptible to, the IL-4Rα-related disorder identified in step (c).

In some instances, the methods include identifying a subject as a candidate for treatment for an anti-interleukin-4 receptor alpha (IL-4Rα)-related disorder with an anti-IL-4Rα antibody comprising (a) selecting a characteristic or a plurality of characteristics related to an IL 4/IL 13 pathway in a set of data representing medical records of a plurality of subjects; (b) clustering, by a computer system, in accordance with the characteristic or the plurality of characteristics related to the IL-4/IL-13 pathway, a subset of subjects from the plurality of subjects, wherein the subset comprises the characteristic or the plurality of characteristics; (c) identifying in the subset clustered in step (b) the IL-4Rα-related disorder based on symptoms associated with the characteristic or the plurality of characteristics related to the IL-4/IL-13 pathway; and (d) selecting the subject having at least one symptom of, or determined to be susceptible to, the IL-4Rα-related disorder identified in step (c) with the proviso that the IL-4Rα related disorder is not selected from the group consisting of atopic dermatitis, asthma, chronic rhinosinusitis with nasal polyposis, eosinophilic esophagitis, peanut allergy, grass allergy, chronic obstructive pulmonary disease (COPD), prurigo nodularis, bullous pemphigoid, chronic spontaneous urticaria (CSU) and allergic bronchopulmonary aspergillosis (ABPA).

In some instances, the methods include identifying a subject as a candidate for treatment for an anti-interleukin-4 receptor alpha (IL-4Rα)-related disorder with an anti-IL-4Rα antibody comprising (a) selecting a characteristic or a plurality of characteristics related to an IL 4/IL 13 pathway in a set of data representing medical records of a plurality of subjects; (b) clustering, by a computer system, in accordance with the characteristic or the plurality of characteristics related to the IL-4/IL-13 pathway, a subset of subjects from the plurality of subjects, wherein the subset comprises the characteristic or the plurality of characteristics; (c) identifying in the subset clustered in step (b) the IL-4Rα-related disorder based on symptoms associated with the characteristic or the plurality of characteristics related to the IL-4/IL-13 pathway; and (d) selecting the subject having at least one symptom of, or determined to be susceptible to, the IL-4Rα-related disorder identified in step (c). In some instances, the method further comprises administering a therapeutically effective amount of the anti-IL-4Rα antibody to the subject, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

In some instances, the methods include identifying a subject as a candidate for treatment for an anti-interleukin-4 receptor alpha (IL-4Rα)-related disorder with an anti-IL-4Rα antibody comprising (a) selecting a characteristic or a plurality of characteristics related to an IL 4/IL 13 pathway in a set of data representing medical records of a plurality of subjects; (b) clustering, by a computer system, in accordance with the characteristic or the plurality of characteristics related to the IL-4/IL-13 pathway, a subset of subjects from the plurality of subjects, wherein the subset comprises the characteristic or the plurality of characteristics; (c) identifying in the subset clustered in step (b) the IL-4Rα-related disorder based on symptoms associated with the characteristic or the plurality of characteristics related to the IL-4/IL-13 pathway; and (d) selecting the subject having at least one symptom of, or determined to be susceptible to, the IL-4Rα-related disorder identified in step (c) with the proviso that the IL-4Rα related disorder is not selected from the group consisting of atopic dermatitis, asthma, chronic rhinosinusitis with nasal polyposis, eosinophilic esophagitis, peanut allergy, grass allergy, chronic obstructive pulmonary disease (COPD), prurigo nodularis, bullous pemphigoid, chronic spontaneous urticaria (CSU) and allergic bronchopulmonary aspergillosis (ABPA). In some instances, the method further comprises administering a therapeutically effective amount of the anti-IL-4Rα antibody to the subject, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

In some instances, disclosed is a method of treating a subject with an anti-interleukin-4 receptor antibody, comprising: (a) selecting a characteristic or a plurality of characteristics in a set of patients; (b) clustering, by a computer system, in accordance with the characteristic or the plurality of characteristics, a subset of patients having the characteristic or the plurality of characteristics, wherein the characteristic or the plurality of characteristics are associated with at least one symptom of, or determined to be susceptible to, an IL-4R-related disorder; and (c) administering a therapeutically effective amount of an anti-IL-4R antibody to the subject exhibiting at least one symptom of, or determined to be susceptible to, the IL-4R-related disorder, wherein the anti-IL-4R antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the anti-IL-4R antibody is an anti-IL-4R-alpha antibody. In some instances, the anti-IL-4R antibody is dupilumab. In some instances, the IL-4R-related disorder is an IL-4R-alpha-related disorder. In some instances, the IL-4Rα-related disorder is a condition listed in Table 9 or Table 10. Also disclosed herein is a method of treating a subject with an anti-interleukin-4 receptor alpha (anti-IL-4Rα) antibody, comprising: (a) selecting a characteristic or a plurality of characteristics in a set of patients; (b) clustering, by a computer system, in accordance with the characteristic or the plurality of characteristics, a subset of patients having the characteristic or the plurality of characteristics, wherein the characteristic or the plurality of characteristics are associated with at least one symptom of, or determined to be susceptible to, an IL-4Rα-related disorder; and (c) administering a therapeutically effective amount of an anti-IL-4Rα antibody to the subject exhibiting at least one symptom of, or determined to be susceptible to, the IL-4Rα-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

Also disclosed herein is a method of treating a subject with an anti-interleukin-4 receptor alpha (anti-IL-4Rα) antibody, wherein the IL-4Rα-related disorder is susceptible to be selected by a machine learning method. In some instances, the method includes (a) selecting a characteristic or a plurality of characteristics related to the IL 4/IL 13 pathway in a set of data representing medical records of a plurality of patients; (b) clustering, by a computer system, in accordance with the characteristic or the plurality of characteristics related to the IL-4/IL-13 pathway, a subset of patients having the characteristic or the plurality of characteristics; (c) identifying in the subset of patients clustered in step (b) the IL-4Rα-related disorder based on the symptoms associated with the characteristic or the plurality of characteristics related to the IL-4/IL-13 pathway; and (d) selecting the IL-4Rα-related disorder identified in step (c) with the proviso that the IL-4Rα related disorder is not selected from the group consisting of atopic dermatitis, asthma, chronic rhinosinusitis with nasal polyposis, eosinophilic esophagitis, peanut allergy, grass allergy, chronic obstructive pulmonary disease (COPD), prurigo nodularis, bullous pemphigoid, chronic spontaneous urticaria (CSU) and allergic bronchopulmonary aspergillosis (ABPA). In some instances, the anti-IL-4Rα antibody comprises a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

In some instances, the anti-interleukin-4 receptor alpha (anti-IL-4Rα) antibody is used for prevention of an IL-4Rα-related disorder. In some instances, the anti-interleukin-4 receptor alpha (anti-IL-4Rα) antibody is used for prevention of an IL-4Rα-related disorder using the methods disclosed herein. In some instances, the anti-interleukin-4 receptor alpha (anti-IL-4Rα) antibody is used for treatment of an IL-4Rα-related disorder. In some instances, the anti-interleukin-4 receptor alpha (anti-IL-4Rα) antibody is used for treatment of an IL-4Rα-related disorder using the methods disclosed herein. In some instances, the IL-4Rα-related disorder is not one of atopic dermatitis, asthma, chronic rhinosinusitis with nasal polyposis, eosinophilic esophagitis, a peanut allergy, a grass allergy, chronic obstructive pulmonary disease (COPD), prurigo nodularis, bullous pemphigoid, chronic spontaneous urticaria (CSU), allergic bronchopulmonary aspergillosis (ABPA), or any combination thereof.

In some instances, the IL-4Rα-related disorder is not atopic dermatitis. In some instances, the IL-4Rα-related disorder is not asthma. In some instances, the IL-4Rα-related disorder is not chronic rhinosinusitis with nasal polyposis. In some instances, the IL-4Rα-related disorder is not eosinophilic esophagitis. In some instances, the IL-4Rα-related disorder is not a peanut allergy. In some instances, the IL-4Rα-related disorder is not a grass allergy. In some instances, the IL-4Rα-related disorder is not chronic obstructive pulmonary disease (COPD). In some instances, the IL-4Rα-related disorder is not prurigo nodularis. In some instances, the IL-4Rα-related disorder is not bullous pemphigoid. In some instances, the IL-4Rα-related disorder is not chronic spontaneous urticaria (CSU). In some instances, the IL-4Rα-related disorder is not allergic bronchopulmonary aspergillosis (ABPA).

In some instances, disclosed is an anti-interleukin-4 receptor alpha (anti-IL-4Rα) antibody for use in the prevention or treatment of a skin-related disorder selected from the group consisting of lichen planus, seborrheic dermatitis, solar urticaria, vitiligo and dyshidrotic eczema, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the prevention or treatment of the skin-related disorder comprises administering a therapeutically effective amount of an anti-IL-4Rα antibody to the subject exhibiting at least one symptom of, or determined to be susceptible to the skin-related disorder.

In some instances, the anti-IL-4Rα antibody comprises a heavy chain variable region (VH) comprising the amino acid sequence of SEQ ID NO:13 and a light chain variable region (VL) comprising the amino acid sequence of SEQ ID NO:14.

In some instances, the skin-related indication is lichen planus. In some instances, the skin-related indication is seborrheic dermatitis. In some instances, the skin-related indication is solar urticaria. In some instances, the skin-related indication is vitiligo. In some instances, the skin-related indication is dyshidrotic eczema. In some instances, the subject is human. In some instances, the administering is intradermal, intramuscular, intraperitoneal, intravenous, subcutaneous, intranasal, or epidural administration. In some instances, the administering is subcutaneous and via a pre-filled syringe, a pre-filled pen or an autoinjector. In some instances, the anti-IL-4Rα antibody is administered over multiple doses. In some instances, the anti-IL-4Rα antibody is administered over two doses. In some instances, the anti-IL-4Rα antibody is administered at a dose of about 0.0001 to about 10 mg/kg of patient body weight. In some instances, the method further comprises administering a second therapeutic agent. In some instances, the second therapeutic agent is a second antibody or antigen binding fragment thereof, a soluble cytokine receptor, an IgE antagonist, an anti-asthma medication, or a checkpoint inhibitor. In some instances, the anti-asthma medication is corticosteroids, non-steroidal agents, beta agonists, leukotriene antagonists, xanthines, fluticasone, salmeterol, or albuterol. In some instances, the checkpoint inhibitor is a PD-1 antagonist, a PD-L1 antagonist, or a CTLA-4 antagonist. In some instances, the anti-IL-4Rα antibody is administered prior, concurrently or subsequent to administering of the second therapeutic agent.

In some instances, disclosed herein is an anti-interleukin-4 receptor alpha (anti-IL-4Rα) antibody for use in the prevention or treatment of an IL-4Rα-related disorder, wherein the IL-4Rα-related disorder is susceptible to be selected by a machine learning method comprising: (a) selecting a characteristic or a plurality of characteristics related to the IL 4/IL 13 pathway in a set of data representing medical records of a plurality of patients; (b) clustering, by a computer system, in accordance with the characteristic or the plurality of characteristics related to the IL-4/IL-13 pathway, a subset of patients having the characteristic or the plurality of characteristics; (c) identifying in the subset of patients clustered in step (b) the IL-4Rα-related disorder based on the symptoms associated with the characteristic or the plurality of characteristics related to the IL-4/IL-13 pathway; and (d) selecting the IL-4Rα-related disorder identified in step (c) with the proviso that the IL-4Rα related disorder is not selected from the group consisting of atopic dermatitis, asthma, chronic rhinosinusitis with nasal polyposis, eosinophilic esophagitis, peanut allergy, grass allergy, chronic obstructive pulmonary disease (COPD), prurigo nodularis, bullous pemphigoid, chronic spontaneous urticaria (CSU) and allergic bronchopulmonary aspergillosis (ABPA); and wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

In some instances, the prevention or treatment of the IL-4Rα-related disorder comprises administering a therapeutically effective amount of an anti-IL-4Rα antibody to the subject exhibiting at least one symptom of, or determined to be susceptible to the IL-4Rα-related disorder. In some instances, the anti-IL-4Rα antibody comprises a heavy chain variable region (VH) comprising the amino acid sequence of SEQ ID NO:13 and a light chain variable region (VL) comprising the amino acid sequence of SEQ ID NO:14. In some instances, the IL-4Rα-related disorder is a skin-related disorder, an allergic reaction, arthritis, a nasal-related disorder, a lung-related disorder, a blood-related disorder, an eye-related disorder, an esophageal-related disorder, a gastrointestinal-related disorder, a kidney-related disorder, a prostate-related disorder, Kawasaki's disease, a thyroid-related disorder, a blood-vessel-related disorder, a pregnancy-related disorder, or a cancer.

In some instances, the skin-related disorder is selected from the group consisting of: dyshidrotic eczema, lichen planus, seborrheic dermatitis, solar urticaria, vitiligo, acne, erythema multiforme, pityriasis rosea, epidermolysis bullosa, dermatitis herpetiformis, allergic contact dermatitis, chronic hand eczema, nummular dermatitis, scleroderma, systemic scleroderma, hypertrophic scarring, infections of the skin, alopecia areata, and Netherton syndrome.

In some instances, the allergic reaction is selected from the group consisting of: hypersensitivity to a dairy product, egg, wheat, soy, corn, fish, shellfish, tree nut, beef, chicken, oat, barley, pork, green beans, apple or pineapple; and hypersensitivity to insect venom, plant-derived material, chemicals, medication, or animal dander.

In some instances, the lung-related disorder is selected from the group consisting of: lung fibrosis, lung cirrhosis, chronic fibrotic lung disease, cystic fibrosis, allergic bronchopulmonary mycosis, bleomycin-induced pneumopathy and fibrosis, pulmonary alveolar proteinosis, adult respiratory distress syndrome, sarcoidosis, tuberculosis, or aspirin-exacerbated respiratory disease.

In some instances, the blood-related disorder is selected from the group consisting of: sickle cell disease, Churg-Strauss syndrome, a combination thereof, autoimmune lymphoproliferative syndrome, lupus (systemic lupus erythematosus), antiphospholipid antibody syndrome (APS), and autoimmune hemolytic anemia.

In some instances, the eye-related disorder is selected from the group consisting of: Sjogren's syndrome, autoimmune uveitis, autoimmune lymphoproliferative syndrome, atopic keratoconjunctivitis (AKC), dry eye, blepharitis, blepharoconjunctivitis, cicatricial pemphigoid, Mooren's corneal ulcer, Vogt-Koyanagi-Harada syndrome, sympathetic opthalmia, phacoanaphylaxis endophthalmitis, and keratoconjunctivitis sicca (KCS).

In some instances, the esophageal-related disorder or gastrointestinal-related disorder is selected from the group consisting of Barrett's esophagus, eosinophilic gastritis, achalasia, gastroesophageal reflux disease (GERD), ulcerative colitis, Whipple's disease, and Behçet's disease or Wegener granulomatosis. In some instances, the kidney-related disorder is selected from the group consisting of: nephrosis, glomerulonephritis, and Goodpasture syndrome. In some instances, the prostate-related disorder is benign prostate hyperplasia (BPH) or chronic prostatitis syndrome.

In some instances, the cancer is cutaneous T-cell lymphomas.

In some instances, the thyroid-related disorder is Hashimoto's disease or Grave's disease.

In some instances, the blood-vessel related disease is vasculitis, polyarteritis nodosa, lupus, or antiphospholipid antibody syndrome (APS).

In some instances, the pregnancy-related disorder is selected from the group consisting of antiphospholipid syndrome, immune thrombocytopenia and pre-eclampsia.

In some instances, the subject is human. In some instances, the administering is intradermal, intramuscular, intraperitoneal, intravenous, subcutaneous, intranasal, or epidural administration. In some instances, the administering is subcutaneous and via a pre-filled syringe, a pre-filled pen or an autoinjector. In some instances, the anti-IL-4Rα antibody is administered over multiple doses. In some instances, the anti-IL-4Rα antibody is administered over two doses. In some instances, the anti-IL-4Rα antibody is administered at a dose of about 0.0001 to about 10 mg/kg of patient body weight. In some instances, the method further comprises administering a second therapeutic agent. In some instances, the second therapeutic agent is a second antibody or antigen binding fragment thereof, a soluble cytokine receptor, an IgE antagonist, an anti-asthma medication, or a checkpoint inhibitor. In some instances, the anti-asthma medication is corticosteroids, non-steroidal agents, beta agonists, leukotriene antagonists, xanthines, fluticasone, salmeterol, or albuterol. In some instances, the checkpoint inhibitor is a PD-1 antagonist, a PD-L1 antagonist, or a CTLA-4 antagonist. In some instances, the anti-IL-4Rα antibody is administered prior, concurrently or subsequent to administering of the second therapeutic agent.

In some instances, the anti-IL-4Rα antibody comprises a heavy chain variable region (VH) comprising the amino acid sequence of SEQ ID NO:13 and a light chain variable region (VL) comprising the amino acid sequence of SEQ ID NO:14.

In some instances, the IL-4Rα-related disorder is an allergic reaction. In some instances, the allergic reaction is a hypersensitivity to a food selected from a dairy product, egg, wheat, soy, corn, fish, shellfish, peanut, tree nut, beef, chicken, oat, barley, pork, green beans, apple and pineapple. In some instances, the allergic reaction is a hypersensitivity to insect venom, plant-derived material, chemicals, medication, or animal dander.

In some instances, the IL-4Rα-related disorder is arthritis.
In some instances, the IL-4Rα-related disorder is asthma.
In some instances, the IL-4Rα-related disorder is a nasal-related disorder. In some instances, the nasal-related disorder is nasal polyposis. In some instances, the nasal-related disorder is sinusitis. In some instances, the nasal-related disorder is rhinitis.

In some instances, the IL-4Rα-related disorder is a lung-related disorder. In some instances, the lung-related disorder is lung fibrosis or lung cirrhosis. In some instances, the lung-related disorder is selected from chronic fibrotic lung disease, cystic fibrosis, allergic bronchopulmonary mycosis, chronic obstructive pulmonary disease, bleomycin-induced pneumopathy and fibrosis, pulmonary alveolar proteinosis, adult respiratory distress syndrome, sarcoidosis, tuberculosis, aspirin-exacerbated respiratory disease, or a combination thereof.

In some instances, the IL-4Rα-related disorder is a blood-related disorder. In some instances, the blood-related disorder is sickle cell disease, Churg-Strauss syndrome, or a combination thereof.

In some instances, the IL-4Rα-related disorder is an eye-related disorder. In some instances, the eye-related disorder is selected from Sjogren's syndrome, autoimmune uveitis, autoimmune lymphoproliferative syndrome, atopic keratoconjunctivis, or a combination thereof.

In some instances, the IL-4Rα-related disorder is an esophageal-related disorder. In some instances, the esophageal-related indication is selected from Barrett's esophagus, eosinophilic esophagitis, eosinophilic gastritis, or a combination thereof.

In some instances, the IL-4Rα-related disorder is a skin-related indication. In some instances, the skin-related disorder is selected from atopic dermatitis, allergic contact dermatitis, dermatitis herpetiformis, dyshidrotic eczema, chronic hand eczema, nummular dermatitis, scleroderma, systemic scleroderma, hypertrophic scarring, urticaria, infections of the skin, alopecia areata, prurigo nodularis, bullous pemphigoid, Netherton syndrome, or a combination thereof.

In some instances, the IL-4Rα-related disorder is a gastrointestinal-related disorder. In some instances, the gastrointestinal-related disorder is ulcerative colitis or Whipple's disease.

In some instances, the IL-4Rα-related disorder is a kidney-related disorder. In some instances, the kidney-related disorder is nephrosis.

In some instances, the IL-4Rα-related disorder is benign prostrate hyperplasia. In some instances, the IL-4Rα-related disorder is Grave's disease. In some instances, the IL-4Rα-related disorder is Kawasaki's disease. In some instances, the IL-4Rα-related disorder is pre-eclampsia.

In some instances, the IL-4Rα-related disorder is a cancer. In some instances, the cancer is cutaneous T-cell lymphomas.

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, a disorder selected from the group consisting of: lung fibrosis, including chronic fibrotic lung disease, cystic fibrosis, interstitial lung disease, nonspecific interstitial pneumonitis, idiopathic pulmonary fibrosis, hypersensitivity pneumonitis, cryptogenic organizing pneumonia (COP), acute interstitial pneumonitis, desquamative interstitial pneumonitis, chronic obstructive pulmonary disease, pulmonary alveolar proteinosis, adult respiratory distress syndrome (ARDS), asbestosis, sarcoidosis, tuberculosis, and aspirin-exacerbated respiratory disease, and wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

In some instances, also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, a blood-related disorder, wherein the anti-IL-4Rα antibody comprises a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the blood-related disorder is sickle cell disease, Churg-Strauss syndrome, autoimmune lymphoproliferative syndrome, lupus (systemic lupus erythematosus), antiphospholipid antibody syndrome (APS), or autoimmune hemolytic anemia.

In some instances, also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, an eye-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the eye-related disorder is, dry eye, blepharitis, blepharoconjunctivitis, cicatricial pemphigoid, Mooren's corneal ulcer, Vogt-Koyanagi-Harada syndrome, sympathetic opthalmia, phacoanaphylaxis endophthalmitis, keratoconjunctivitis sicca (KCS), or atopic keratoconjunctivitis (AKC).

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, an esophageal-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the esophageal-related disorder is, achalasia, or gastroesophageal reflux disease (GERD).

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, a skin-related disorder selected from allergic contact dermatitis, dermatitis herpetiformis, dyshidrotic eczema, chronic hand eczema, nummular dermatitis, scleroderma, systemic scleroderma, dermatomyositis, epidermolysis bullosa, hypertrophic scarring, urticaria, skin infections, alopecia areata, prurigo nodularis, bullous pemphigoid, or Netherton syndrome, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, a gastrointestinal-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the gastrointestinal-related disorder is ulcerative colitis Behçet's disease, Wegener granulomatosis or GERD.

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, a kidney-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the kidney-related disorder is nephrosis, glomerulonephritis, or Goodpasture syndrome.

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, a prostate-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the prostate-related disorder is benign prostate hyperplasia (BPH) or chronic prostatitis syndrome.

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, a thyroid-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the thyroid-related disorder is Hashimoto's disease.

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, a blood-vessel-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the blood-vessel related disease is vasculitis, polyarteritis nodosa, lupus, or antiphospholipid antibody syndrome (APS).

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, a pregnancy-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the pregnancy-related disorder is Antiphospholipid Syndrome or Immune Thrombocytopenia.

Also disclosed herein is a method of treating a subject with an anti-interleukin-4 receptor alpha (anti-IL-4Rα) antibody, comprising administering a therapeutically effective amount of an anti-IL-4Rα antibody to a subject exhibiting at least one symptom of, or determined to be susceptible to, cancer, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the cancer is cutaneous T-cell lymphoma.

In some instances, the subject is human.

In some instances, the administering is intradermal, intramuscular, intraperitoneal, intravenous, subcutaneous, intranasal, or epidural administration. In some instances, the administering is subcutaneous. In some instances, the administering is via a pre-filled syringe. In some instances, the administering is via a pre-filled pen. In some instances, the administering is via an autoinjector. In some instances, the anti-IL-4Rα antibody is administered over multiple doses. In some instances, the anti-IL-4Rα antibody is administered over two doses. In some instances, the anti-IL-4Rα antibody is administered at a dose of about 0.0001 to about 10 mg/kg of patient body weight.

In some instances, the methods disclosed herein further comprise administering a second therapeutic agent. In some instances, the second therapeutic agent is a second antibody or antigen binding fragment thereof, a soluble cytokine receptor, an IgE antagonist, an anti-asthma medication, or a checkpoint inhibitor. In some instances, the anti-asthma medication is corticosteroids, non-steroidal agents, beta agonists, leukotriene antagonists, xanthines, fluticasone, salmeterol, or albuterol. In some instances, the checkpoint inhibitor is a PD-1 antagonist, a PD-L1 antagonist, or a CTLA-4 antagonist. In some instances, the anti-IL-4Rα antibody is administered prior to administering the second therapeutic agent. In some instances, the anti-IL-4Rα antibody is administered concurrently with the administering of the second therapeutic agent. In some instances, the anti-IL-4Rα antibody is administered subsequent to the administering of the second therapeutic agent.

In some instances, disclosed herein are compositions comprising an anti-IL-4Rα antibody for use in the treatment of disease. In some instances, disclosed are compositions comprising an anti-IL-4Rα antibody for use in the treatment of one or more diseases or disorders as disclosed herein.

In some instances, disclosed are compositions comprising an anti-IL-4R antibody (e.g., an anti-IL-4Rα antibody, e.g., dupilumab) for use in the treatment of a lung-related indication. In some instances, the lung-related indication is lung fibrosis, including chronic fibrotic lung disease, cystic fibrosis, interstitial lung disease, nonspecific interstitial pneumonitis, idiopathic pulmonary fibrosis, hypersensitivity pneumonitis, cryptogenic organizing pneumonia (COP), acute interstitial pneumonitis, desquamative interstitial pneumonitis, chronic obstructive pulmonary disease, pulmonary alveolar proteinosis, adult respiratory distress syndrome (ARDS), asbestosis, sarcoidosis, tuberculosis, and aspirin-exacerbated respiratory disease.

In some instances, disclosed are compositions comprising an anti-IL-4R antibody (e.g., an anti-IL-4Rα antibody, e.g., dupilumab) for use in the treatment of blood-related indications. In some instances, the blood-related indication is sickle cell disease, Churg-Strauss syndrome, autoimmune lymphoproliferative syndrome, lupus (systemic lupus erythematosus), antiphospholipid antibody syndrome (APS), or autoimmune hemolytic anemia.

In some instances, disclosed are compositions comprising an anti-IL-4R antibody (e.g., an anti-IL-4Rα antibody, e.g., dupilumab) for use in the treatment of eye-related indications. In some instances, the eye-related indication is Sjogren's syndrome, autoimmune uveitis, or atopic keratoconjunctivitis (AKC).

In some instances, disclosed are compositions comprising an anti-IL-4R antibody (e.g., an anti-IL-4Rα antibody, e.g., dupilumab) for use in the treatment of esophageal-related indications. In some instances, the esophageal-related indication is Barrett's esophagus, eosinophilic esophagitis, or eosinophilic gastritis.

In some instances, disclosed are compositions comprising an anti-IL-4R antibody (e.g., an anti-IL-4Rα antibody, e.g., dupilumab) for use in the treatment of skin-related indications. In some instances, the skin-related indication is atopic dermatitis (AD), allergic contact dermatitis, dermatitis herpetiformis, dyshidrotic eczema, chronic hand eczema, nummular dermatitis, scleroderma, hypertrophic scarring, urticaria, skin infections, alopecia areata, prurigo nodularis, bullous pemphigoid, Netherton syndrome, or another dermatologic condition.

In some instances, disclosed are compositions comprising an anti-IL-4R antibody (e.g., an anti-IL-4Rα antibody, e.g., dupilumab) for use in the treatment of gastrointestinal-related indications. In some instances, the gastrointestinal-related indication is ulcerative colitis or Whipple's disease.

In some instances, disclosed are compositions comprising an anti-IL-4R antibody (e.g., an anti-IL-4Rα antibody, e.g., dupilumab) for use in the treatment of kidney-related indications. In some instances, the kidney-related indication is nephrosis.

In some instances, disclosed are compositions comprising an anti-IL-4R antibody (e.g., an anti-IL-4Rα antibody, e.g., dupilumab) for use in the treatment of benign prostate hyperplasia (BPH). In some instances, disclosed are compositions comprising an anti-IL-4R antibody (e.g., an anti-IL-4Rα antibody, e.g., dupilumab) for use in the treatment of Grave's disease. In some instances, disclosed are compositions comprising an anti-IL-4R antibody (e.g., an anti-IL-4Rα antibody, e.g., dupilumab) for use in the treatment of pre-eclampsia.

In some instances, disclosed are compositions comprising an anti-IL-4R antibody (e.g., an anti-IL-4Rα antibody, e.g., dupilumab) for use in the treatment of cancer. In some instances, the cancer is a cutaneous T-cell lymphoma (CTCL).

In some instances, disclosed are compositions comprising an anti-IL-4R antibody (e.g., an anti-IL-4Rα antibody, e.g., dupilumab) for use in enhancing efficacy of a vaccine.

In some instances, disclosed are compositions comprising an anti-IL-4R antibody (e.g., an anti-IL-4Rα antibody, e.g., dupilumab) for use in the treatment of an allergy. In some instances, disclosed are compositions comprising an anti-IL-4R antibody (e.g., an anti-IL-4Rα antibody, e.g., dupilumab) for use in the treatment of asthma. In some instances, disclosed are compositions comprising an anti-IL-4R antibody (e.g., an anti-IL-4Rα antibody, e.g., dupilumab) for use in the treatment of arthritis.

In some instances, disclosed are compositions comprising an anti-IL-4R antibody (e.g., an anti-IL-4Rα antibody, e.g., dupilumab) for use in the treatment of nasal-related indications. In some instances, the nasal-related indication is nasal polyposis, sinusitis, or rhinitis.

In some instances, disclosed herein are uses of a composition comprising an anti-IL-4Rα in the manufacture of a medicament for the treatment of one or more diseases or disorders as disclosed herein.

In some instances, disclosed are uses of a compositions comprising an anti-IL-4Rα (e.g., dupilumab) in the manufacture of a medicament for the treatment of a lung-related indication. In some instances, the lung-related indication is lung fibrosis, including chronic fibrotic lung disease, cystic fibrosis, interstitial lung disease, nonspecific interstitial pneumonitis, idiopathic pulmonary fibrosis, hypersensitivity pneumonitis, cryptogenic organizing pneumonia (COP), acute interstitial pneumonitis, desquamative interstitial pneumonitis, chronic obstructive pulmonary disease, pulmonary alveolar proteinosis, adult respiratory distress syndrome (ARDS), asbestosis, sarcoidosis, tuberculosis, and aspirin-exacerbated respiratory disease.

In some instances, disclosed are uses of a compositions comprising an anti-IL-4Rα (e.g., dupilumab) in the manufacture of a medicament for the treatment of blood-related indications. In some instances, the blood-related indication is sickle cell disease, Churg-Strauss syndrome, autoimmune lymphoproliferative syndrome, lupus (systemic lupus erythematosus), antiphospholipid antibody syndrome (APS), or autoimmune hemolytic anemia.

In some instances, disclosed are uses of a compositions comprising an anti-IL-4Rα (e.g., dupilumab) in the manufacture of a medicament for the treatment of eye-related indications. In some instances, the eye-related indication is Sjogren's syndrome, autoimmune uveitis, or atopic keratoconjunctivitis (AKC).

In some instances, disclosed are uses of a compositions comprising an anti-IL-4Rα (e.g., dupilumab) in the manufacture of a medicament for the treatment of esophageal-related indications. In some instances, the esophageal-related indication is Barrett's esophagus, eosinophilic esophagitis, or eosinophilic gastritis.

In some instances, disclosed are uses of a compositions comprising an anti-IL-4Rα (e.g., dupilumab) in the manufacture of a medicament for the treatment of skin-related indications. In some instances, the skin-related indication is atopic dermatitis (AD), allergic contact dermatitis, dermatitis herpetiformis, dyshidrotic eczema, chronic hand eczema, nummular dermatitis, scleroderma, systemic scleroderma, hypertrophic scarring, urticaria, skin infections, alopecia areata, prurigo nodularis, bullous pemphigoid, or Netherton syndrome.

In some instances, disclosed are uses of a compositions comprising an anti-IL-4Rα (e.g., dupilumab) in the manufacture of a medicament for the treatment of gastrointestinal-related indications. In some instances, the gastrointestinal-related indication is ulcerative colitis or Whipple's disease.

In some instances, disclosed are uses of a compositions comprising an anti-IL-4Rα (e.g., dupilumab) in the manufacture of a medicament for the treatment of kidney-related indications. In some instances, the kidney-related indication is nephrosis.

In some instances, disclosed are uses of a compositions comprising an anti-IL-4Rα (e.g., dupilumab) in the manufacture of a medicament for the treatment of benign prostate hyperplasia (BPH). In some instances, disclosed are compositions comprising an anti-IL-4R antibody (e.g., an anti-IL-4Rα antibody, e.g., dupilumab) for use in the treatment of Grave's Disease. In some instances, disclosed are compositions comprising an anti-IL-4R antibody (e.g., an anti-IL-4Rα antibody, e.g., dupilumab) for use in the treatment of pre-eclampsia.

In some instances, disclosed are uses of a compositions comprising an anti-IL-4Rα (e.g., dupilumab) in the manufacture of a medicament for the treatment of cancer. In some instances, the cancer is a Cutaneous T-cell lymphoma (CTCL).

In some instances, disclosed are uses of a compositions comprising an anti-IL-4Rα (e.g., dupilumab) in the manufacture of a medicament for the enhancement of efficacy of a vaccine.

In some instances, disclosed are uses of a compositions comprising an anti-IL-4Rα (e.g., dupilumab) in the manufacture of a medicament for the treatment of an allergy. In some instances, disclosed are uses of a compositions comprising an anti-IL-4Rα (e.g., dupilumab) in the manufacture of a medicament for the treatment of asthma. In some instances, disclosed are uses of a compositions comprising an anti-IL-4Rα (e.g., dupilumab) in the manufacture of a medicament for the treatment of arthritis.

In some instances, disclosed are uses of a compositions comprising an anti-IL-4Rα (e.g., dupilumab) in the manufacture of a medicament for the treatment of nasal-related indications. In some instances, the nasal-related indication is nasal polyposis, sinusitis, or rhinitis.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various aspects of the features of this disclosure are described herein. However, it should be understood that such aspects are provided merely by way of example, and numerous variations, changes, and substitutions can occur to those skilled in the art without departing from the scope of this disclosure. It should also be understood that various alternatives to the specific aspects described herein are also within the scope of this disclosure.

BRIEF DESCRIPTION OF DRAWINGS

FIGS. 6A-6D indicates the top 30 indications, based on co-occurrence with at least one of four referential "immunological conditions": asthma, atopic dermatitis, hyperimmunoglobulin E (IgE) syndrome, and a broader composite immunology score.

FIGS. 7A-7D indicates a re-ranking of the top 30 novel indications in each referential group after removal of indications already known to be in clinical trials, including investigator-initiated trials (IITs). The italics indications appear in more than one referential group.

DETAILED DESCRIPTION

Figure 1:
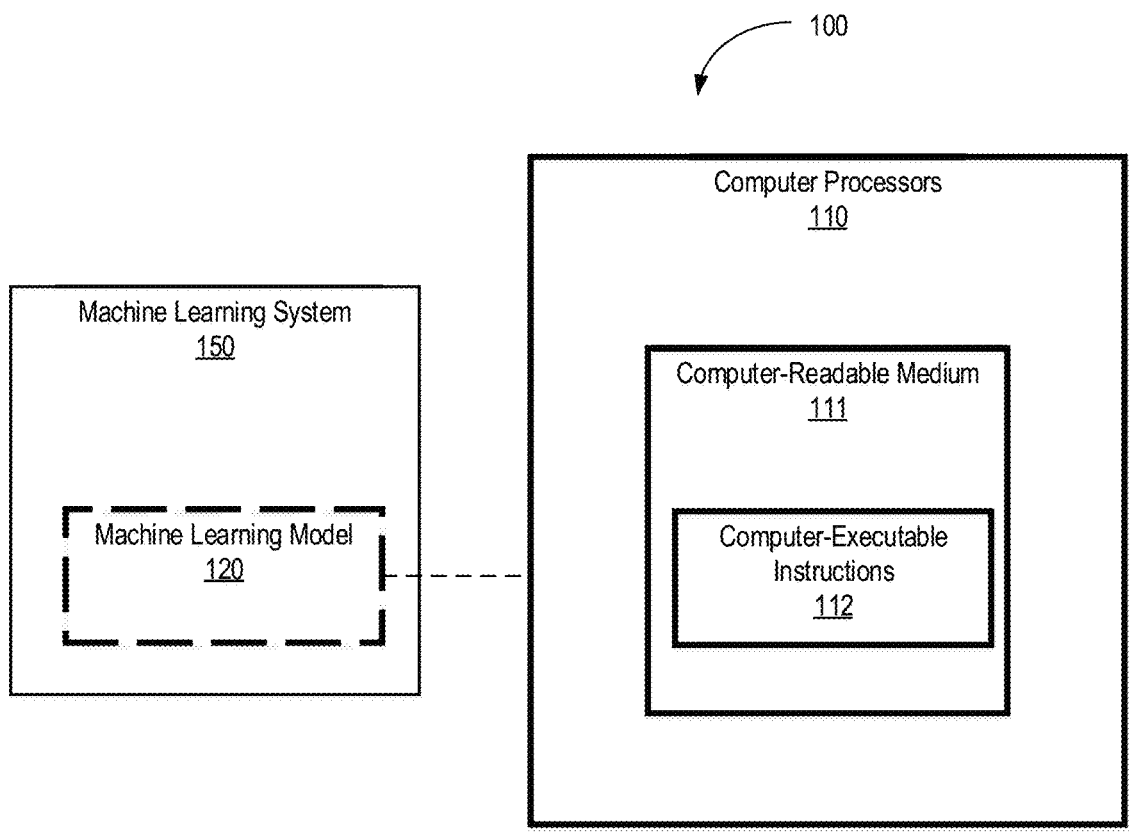
FIG. 1 is a diagram illustrating an example of a data processing system for drug repurposing.

The present disclosure is based, at least in part, on the discovery that dupilumab (i.e., DUPIXENT®) can be used to treat various disorders in addition to those currently approved by the FDA. FDA-approved uses of dupilumab include, e.g., (1) treatment of adult patients with moderate-to-severe atopic dermatitis whose disease is not adequately controlled with topical prescription therapies or when those therapies are not advisable; (2) use with other asthma medicines for the maintenance treatment of moderate-to-severe eosinophilic or oral steroid dependent asthma in people aged 12 years and older whose asthma is not controlled with their current asthma medicines; and (3) use with other medicines to treat chronic rhinosinusitis with nasal polyposis in adults whose disease is not controlled.

The new indications, which are the subject of the present specification, were at least in part identified using computational methods that analyze data obtained from millions of patients and predict therapeutic outcomes for specific drugs. Starting with those predictions, the present inventors have developed treatments for various diseases and disorders described herein using an anti-IL-4R antibody (e.g., an anti-IL-4Rα antibody, e.g., dupilumab).

As used herein, "IL-4" is a pleiotropic cytokine produced by activated T cells that is a ligand for interleukin 4 receptor.

The interleukin 4 receptor (IL-4R) also binds to IL-13, which may contribute to many overlapping functions of the IL-4 and IL-13 cytokines. STATE, a signal transducer and activator of transcription, has been shown to play a central role in mediating the immune regulatory signal of IL-4. Along with IL-13, IL-4 plays important roles in regulating the responses of lymphocytes, myeloid cells, and non-hematopoietic cells. In T-cells, IL-4 induces the differentiation of naïve CD4 T cells into Th2 cells. In B cells, IL-4 drives the immunoglobulin (Ig) class switch to IgG1 and IgE. In macrophages, IL-4 induces alternative macrophage activation.

The term "human IL-4R" (hIL-4R) means a human cytokine receptor that specifically binds interleukin-4 (IL-4). The term "human interleukin-13" (hIL-13) refers to a human cytokine that specifically binds IL-13 receptor, and "hIL-13/hIL-13R1 complex" refers to the complex formed by hIL-13 binding to hIL-13R1 complex, which complex binds hIL-4 receptor to initiate biological activity.

The term "anti-interleukin-4 receptor alpha antibody" (or IL-4R antibody, IL-4Rα antibody, hIL-4R antibody, or hIL-4Rα antibody), as used herein, is intended to refer to an antibody that binds to and inhibits function of IL-4 (or IL-4Rα).

"Dupilumab" (or "DUPIXENT®") is an interleukin-4 (IL-4) receptor alpha antagonist. Dupilumab is a human monoclonal antibody of the immunoglobulin G4 subclass that inhibits IL-4 and interleukin-13 (IL-13) signaling by specifically binding to the IL-4 receptor alpha subunit, which is shared by the IL-4 and IL-13 receptor complexes. Dupilumab inhibits IL-4 signaling via the type 1 receptor and both IL-4 and IL-13 signaling via the type 2 receptor. By blocking the IL-4R alpha subunit, dupilumab inhibits IL-4 and IL-13 cytokine-induced responses, including the release of proinflammatory cytokines, chemokines, and immunoglobulin E.

The term "antibody", as used herein, refers to immunoglobulin molecules including four polypeptide chains, two heavy (H) chains and two light (L) chains inter-connected by disulfide bonds. Each heavy chain includes a heavy chain variable region (HCVR or VH) and a heavy chain constant region. The heavy chain constant region includes three domains, CH1, CH2 and CH3. Each light chain includes a light chain variable region (LCVR or VL) and a light chain constant region. The light chain constant region includes one domain (CL1). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding fragment" of an antibody (alternatively referred to as "antigen-binding portion" or "antibody fragment") refers to a fragment of an antibody that retains an ability to specifically bind to an antigen (e.g., hIL-4R). It has been shown that the antigen-binding function of an antibody can be performed by fragments of a full-length antibody Exemplary antigen-binding fragments include (i) a Fab fragment, a monovalent fragment consisting of the VL, VH, CL1 and CH1 domains; (ii) a F(ab')2 fragment, a bivalent fragment including two F(ab)' fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain; and (vi) a CDR. Furthermore, although the two domains of the Fv fragment, VL and VH, are coded for by separate genes, they can be joined, using recombinant methods, by a synthetic linker that enables them to be made as a single contiguous chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883. Such single chain antibodies are also encompassed within the term "antigen-binding fragment" of an antibody. Other forms of single chain antibodies, such as diabodies, are also encompassed (see e.g., Holliger et al. (1993) Proc. Natl. Acad Sci. USA 90:6444-6448). A more detailed description of antigen-binding fragments useful in the present disclosure is provided below.

A "neutralizing" or "blocking" antibody, refers to an antibody whose binding to hIL-4Rα results in inhibition of the biological activity of hIL-4 and/or hIL-13. This inhibition of the biological activity of hIL-4 and/or IL-13 can be assessed by measuring one or more indicators of hIL-4 and/or hIL-13 biological activity known to the art, such as hIL-4- and/or IL-13-induced cellular activation and hIL-4 binding to hIL-4Rα (see examples below).

A "CDR" or "complementarity determining region" is a region of hypervariability interspersed within regions that are more conserved, termed "framework regions" (FR). In different embodiments of the anti-hIL-4Rα antibody or antigen-binding fragment of the disclosure, the FRs can be identical to the human germline sequences, or can be naturally or artificially modified.

The term "epitope" is an antigenic determinant that interacts with a specific antigen binding site in the variable region of an antibody molecule known as a paratope. A single antigen can have more than one epitope. Epitopes can be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope can include moieties of saccharides, phosphoryl groups, or sulfonyl groups on the antigen.

The terms "substantial identity," "substantially identical," "substantial similarity," "substantially similar" derivatives and variations when referring to a nucleic acid or protein refers to sequences that are at least about 75% identical to the SEQ ID NOs: 1-16, described herein, can be used in the methods and compositions described herein. In some instances, the nucleotide sequences are about 80%, 85%, 90%, 95%, 99% or 100% identical.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software As used herein, the terms "subject" and "patient" are used interchangeably. The subject can be an animal. In some instances, the subject is a mammal such as a non-primate (e.g., cow, pig, horse, cat, dog, rat, etc.) or a primate (e.g., monkey or human). In some instances, the subject is a human. In certain instances, such terms refer to a non-human animal (e.g., a non-human animal such as a pig, horse, cow, cat, or dog).

As used herein, the terms "about" and "approximately," when used to modify a numeric value or numeric range, indicate that deviations of 5% to 10% above and 5% to 10% below the value or range remain within the intended meaning of the recited value or range It is understood that wherever aspects are described herein with the language "comprising," otherwise analogous aspects described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Anti-IL-4Rα Antibodies, Antigen-Binding Fragments, and Compositions

The present disclosure describes, inter alia, the use of anti-IL-4Rα antibodies to treat various disorders. The various disorders were identified as being treatable with anti-IL-4Rα antibodies using the digital process of analyzing patient data described herein. Prior to the present disclosure, these disorders were not known to be treatable with an anti-IL-4Rα such as dupilumab. Accordingly, a brief description of anti-IL-4Rα antibodies and fragments, compositions, and dosages, useful in the presently-described methods is provided below.

I. Antibodies and Fragments

Of particular use in the present disclosure are anti-IL-4Rα antibodies. Skilled practitioners will appreciate that a complete antibody includes four polypeptide chains, two heavy (H) chains and two light (L) chains, inter-connected by disulfide bonds, and in some instances includes multimers thereof (e.g., IgM). In a typical antibody, each heavy chain includes a heavy chain variable region (abbreviated herein as HCVR or VH) and a heavy chain constant region. The heavy chain constant region includes three domains, CH1, CH2 and CH3. Each light chain includes a light chain variable region (abbreviated herein as LCVR or VL) and a light chain constant region. The light chain constant region includes one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-IL-4Rα antibody (or antigen-binding portion thereof) can be identical to the human germline sequences, or can be naturally or artificially modified. An amino acid consensus sequence can be defined based on a side-by-side analysis of two or more CDRs.

An antigen-binding fragment of a full antibody can also be useful in the presently-described methods. An antigen-binding fragment (e.g., of an anti-IL-4Rα antibody) can be, e.g., any naturally occurring, enzymatically obtainable, synthetic, or genetically engineered polypeptide or glycoprotein that specifically binds an antigen to form a complex. Antigen-binding fragments of an antibody can be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA can be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically includes at least one variable domain. The variable domain can be of any size or amino acid composition and generally includes at least one CDR which is adjacent to or in frame with one or more framework sequences. In antigen-binding fragments having a VH domain associated with a VL domain, the VH and VL domains can be situated relative to one another in any suitable arrangement. For example, the variable region can be dimeric and contain VH-VH, VH-VL or VL-VL dimers. Alternatively, the antigen-binding fragment of an antibody can contain a monomeric VH or VL domain.

In certain instances, an antigen-binding fragment of an antibody can include at least one variable domain covalently linked to at least one constant domain. Non-limiting, exemplary configurations of variable and constant domains that can be found within an antigen-binding fragment of an antibody include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains can be either directly linked to one another or can be linked by a full or partial hinge or linker region. A hinge region can consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure can include a homo-dimer or hetero-dimer (or other multimer) of any of the variable and constant domain configurations listed above in non-covalent association with one another and/or with one or more monomeric VH or VL domain (e.g., by disulfide bond(s)).

In some instances, an anti-IL-4Rα antibody can be a multispecific (e.g., bispecific) antibody. A multispecific antibody or antigen-binding fragment of an antibody typically includes at least two different variable domains, wherein each variable domain is capable of specifically binding to a separate antigen or to a different epitope on the same antigen. Any multispecific antibody format can be adapted for use in the context of an antibody or antigen-binding fragment of an antibody of the present disclosure using routine techniques available in the art. For example, the present disclosure includes methods including the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab2 bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J. Am. Chem. Soc. [Epub: Dec. 4, 2012]).

The antibodies used in the methods of the present disclosure can be human antibodies. The term "human antibody," as used herein, is intended to include antibodies having variable and constant regions derived from human germline immunoglobulin sequences. The human antibodies of the disclosure can nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

Antibodies useful in the methods of the present disclosure can be recombinant human antibodies. The term "recombinant human antibody," as used herein, is intended to include human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain instances, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, cannot naturally exist within the human antibody germline repertoire in vivo.

In some instances, antibodies used in the methods of the present disclosure specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present disclosure, includes antibodies that bind IL-4Rα or portion thereof with a Kd of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4Rα can, however, have cross-reactivity to other antigens, such as IL-4Rα molecules from other (non-human) species.

An anti-IL-4Rα antibody that is useful in the presently described methods is an anti-IL-4Rα antibody, or antigen-binding fragment thereof including a heavy chain variable region (HCVR), light chain variable region (LCVR), and/or complementarity determining regions (CDRs), described in U.S. Pat. No. 7,608,693, which is incorporated by reference in its entirety.

In some instances, an anti-IL-4Rα antibody or antigen-binding fragment useful in the presently described methods includes three HCDRs (HCDR1, HCDR2 and HCDR3) and three LCDRs (LCDR1, LCDR2 and LCDR3), wherein the HCDR1 includes the amino acid sequence of SEQ ID NO:1; the HCDR2 includes the amino acid sequence of SEQ ID NO:2; the HCDR3 includes the amino acid sequence of SEQ ID NO:3; the LCDR1 includes the amino acid sequence of SEQ ID NO:4; the LCDR2 includes the amino acid sequence of SEQ ID NO:5; and the LCDR3 includes the amino acid sequence of SEQ ID NO:6. SEQ ID NOs: 1-6 are shown in Table 1.

In some instances, an anti-IL-4Rα antibody or antigen-binding fragment useful in the presently described methods includes three HCDRs (HCDR1, HCDR2 and HCDR3) and three LCDRs (LCDR1, LCDR2 and LCDR3), wherein the HCDR1 includes the amino acid sequence encoded by the nucleotide sequence of SEQ ID NO:7; the HCDR2 includes the amino acid sequence encoded by the nucleotide sequence of SEQ ID NO:8; the HCDR3 includes the amino acid sequence encoded by the nucleotide sequence of SEQ ID NO:9; the LCDR1 includes the amino acid sequence encoded by the nucleotide sequence of SEQ ID NO:10; the LCDR2 includes the amino acid sequence encoded by the nucleotide sequence of SEQ ID NO:11; and the LCDR3 includes the amino acid sequence encoded by the nucleotide sequence of SEQ ID NO:12. SEQ ID NOs: 7-12 are shown in Table 2.

In some instances, an anti-IL-4Rα antibody or antigen-binding fragment useful in the presently described methods includes the heavy chain complementarity determining regions (HCDRs) of a heavy chain variable region (HCVR) of SEQ ID NO:13 and the light chain complementarity determining regions (LCDRs) of a light chain variable region (LCVR) of SEQ ID NO:14. SEQ ID NOs: 13-14 are shown in Table 3.

In some instances, an anti-IL-4Rα antibody or antigen-binding fragment useful in the presently described methods includes the heavy chain complementarity determining regions (HCDRs) of a heavy chain variable region (HCVR) encoded by the nucleotide sequence of SEQ ID NO:15 and the light chain complementarity determining regions (LCDRs) of a light chain variable region (LCVR) encoded by the nucleotide sequence of SEQ ID NO:16. SEQ ID NOs: 15-16 are shown in Table 4.

In some instances, an anti-IL-4Rα antibody or antigen-binding fragment useful in the presently described methods includes the heavy chain sequence of SEQ ID NO:17 and the light chain sequence of SEQ ID NO:18. SEQ ID NOs: 17-18 are shown in Table 5.

One useful anti-IL-4Rα antibody or antigen-binding fragment thereof is, for example, one that specifically binds human interleukin-4 receptor (hIL-4R) including the amino acid sequence of SEQ ID NO: 19. SEQ ID NO: 19 is shown in Table 6. The anti-IL-4Rα antibody or antigen-binding fragment thereof can in some instances specifically bind hIL-4Rα with a KD of about 300 pM or less, as measured by surface plasmon resonance in a monomeric or dimeric assay. The antibody or antigen-binding portion thereof can in some instances exhibit a KD of about 200 pM or less, about 150 or less, about 100 pM or less, or about 50 pM. In some instances, the antibody or antigen-binding fragment blocks hIL-4 activity with an IC50 of about 100 pM or less, as measured by luciferase bioassay. In some instances, the antibody or antigen-binding fragment exhibits an IC50 of about 50 pM or less, about 30 pM or less, or about 25 pM or less, as measured by STAT6 luciferase bioassay. The antibody or antigen-binding fragment can, in some instances, block hIL-13 activity with an IC50 of about 100 pM or less, about 90 pM or less, about 50 pM or less, or about 20 pM or less, as measured by STAT6 luciferase bioassay.

Of particular, use in the presently described methods is the anti-IL-4Rα antibody referred to and known in the art as dupilumab, or a bioequivalent thereof.

TABLE 1

Anti-IL-4Rα antibody (e.g., dupilumab) CDR amino acid sequences.

| SEQ ID NO: | Description | Sequence |
|---|---|---|
| SEQ ID NO:1 | HC CDR1 | GFTFRDYA |
| SEQ ID NO:2 | HC CDR2 | ISGSGGNT |
| SEQ ID NO:3 | HC CDR3 | AKDRLSITIRPRYYGLDV |
| SEQ ID NO:4 | LC CDR1 | QSLLYSIGYNY |
| SEQ ID NO:5 | LC CDR2 | LGS |
| SEQ ID NO:6 | LC CDR3 | MQALQTPYT |

TABLE 2

Anti-IL-4Rα antibody (e.g., dupilumab) CDR nucleotide sequences.

| SEQ ID NO: | Description | Sequence |
|---|---|---|
| SEQ ID NO:7 | HC CDR1 | ggattcacct ttagagacta tgcc |
| SEQ ID NO:8 | HC CDR2 | attagtggtt ccggtggtaa caca |
| SEQ ID NO:9 | HC CDR3 | gcgaaagatc gactctctat aacaattcgc ccacgctatt atggtttgga cgtc |
| SEQ ID NO:10 | LC CDR1 | cagagcctcc tgtatagtat tggatacaac tat |
| SEQ ID NO:11 | LC CDR2 | ttgggttct |
| SEQ ID NO:12 | LC CDR3 | atgcaagctc tacaaactcc gtacact |

TABLE 3

Anti-IL-4Rα antibody (e.g., dupilumab) heavy and light chain variable region amino acid sequences.

| SEQ ID NO: | Description | Sequence |
|---|---|---|
| SEQ ID NO:13 | Heavy chain variable region | EVQLVESGGGLEQPGGSLRLSCAGS GFTFRDYAMTWVRQAPGKGLEWV SSISGSGGNTYYADSVKGRFTISRDN SKNTLYLQMNSLRAEDTAVYYCAK DRLSITIRPRYYGLDVWGQGTTVTV S |
| SEQ ID NO:14 | Light chain variable region | DIVMTQSPLSLPVTPGEPASISCRSSQ SLLYSIGYNYLDWYLQKSGQSPQLLI YLGSNRASGVPDRFSGSGSGTDFTLK ISRVEAEDVGFYYCMQALQTPYTFG QGTKLEIK |

TABLE 4

Anti-IL-4Rα antibody (e.g., dupilumab) heavy and light chain variable region nucleotide sequences.

| SEQ ID NO: | Description | Sequence |
|---|---|---|
| SEQ ID NO: 15 | Heavy chain variable region | gaggtgcagc tggtggagtc tggggggaggc ttggaacagc cggggggtc cctgagactc tcctgtgcag gctctggatt cacctttaga gactatgcca tgacctgggt ccgccaggct ccaggggaagg gactggagtg ggtctcatct attagtggtt ccgtggtaa cacatactac gcagactccg tgaagggccg gttcaccatc tccagagaca attccaagaa cacgctgtat ctgcaaatga acagcctgag agccgaggac acggccgtat attactgtgc gaaagatcga ctctctataa caattcgccc acgctattat ggtttggacg tctggggcca agggaccacg gtcaccgtct cc |
| SEQ ID NO: 16 | Light chain variable region | gacatcgtga tgacccagtc tccactctcc ctgcccgtca cccctggaga gccgcctcc atctcctgca ggtcagtca gagcctcctg tatagtattg gatacaacta ttgggattgg tacctgcaga agtcagggca gtctccacag ctccttatct atttgggttc taatcgggcc tccggggtcc ctgacaggtt cagtggcagt ggatcaggca cagattttac actgaaaatc agcagagtgg aggctgagga tgttgggttt tattactgca tgcaagctct acaaactccg tacacttttg gccaggggac caagctggag atcaaa |

TABLE 5

Anti-IL-4Rα antibody (e.g., dupilumab) heavy and light chain constant amino acid sequences.

| SEQ ID NO: | Description | Sequence |
|---|---|---|
| SEQ ID NO:17 | Heavy Chain | EVQLVESGGGLEQPGGSLRLSCAGSG FTFRDYAMTWVRQAPGKGLEWVSSI SGSGGNTYYADSVKGRFTISRDNSKN TLYLQMNSLRAEDTAVYYCAKDRLS ITIRPRYYGLDVWGQGTTVTVSSAST KGPSVFPLAPCSRSTSESTAALGCLVK DYFPEPVTVSWNSGALTSGVHTFPAV |

TABLE 5-continued

Anti-IL-4Rα antibody (e.g., dupilumab) heavy and light chain constant amino acid sequences.

| SEQ ID NO: | Description | Sequence |
|---|---|---|
| | | LQSSGLYSLSSWTVPSSSLGTKTYTCN VDHKPSNTKVDKRVESKYGPPCPPCP APEFLGGPSVFLFPPKPKDTLMISRTPE VTCVVVDVSQEDPEVQFNWYVDGVE VHNAKTKPREEQFNSTYRVVSVLTVL HQDWLNGKEYKCKVSNKGLPSSIEKT ISKAKGQPREPQVYTLPPSQEEMTKN QVSLTCLVKGFYPSDIAVEWESNGQP ENNYKTTPPVLDSDGSFFLYSRLTVD KSRWQEGNVFSCSVMHEALHNHYTQ KSLSLSLG |
| SEQ ID NO:18 | Light Chain | DIVMTQSPLSLPVTPGEPASISCRSSQSL LYSIGYNYLDWYLQKSGQSPQLLIYLG SNRASGVPDRFSGSGSGTDFTLKISRVE AEDVGFYYCMQALQTPYTFGQGTKLE IKRTVAAPSVFIFPPSDEQLKSGTASVV CLLNNFYPREAKVQWKVDNALQSGNS QESVTEQDSKDSTYSLSSTLTLSKADY EKHKVYACEVTHQGLSSPVTKSFNRG EC |

TABLE 6

Human interleukin-4 receptor.

| SEQ ID NO: | Description | Sequence |
|---|---|---|
| SEQ ID NO: 19 | Human IL-4R | MKVLQEPTCVSDYMSISTCEWKMNGP TNCSTELRLLYQLVFLLSEAHTCIPENN GGAGCVCHLLMDDVVSADNYTLDLW AGQQLLWKGSFKPSEHVKPRAPGNLT VHTNVSDTLLLTWSNPYPPDNYLYNH LTYAVNIWSENDPADFRIYNVTYLEPS LRIAASTLKSGISYRARVRAWAQCYNT TWSEWSPSTKWHNSYREPFEQH |

Other anti-IL-4Rα antibodies that can be used in the context of the methods of the present disclosure include, e.g., the antibody referred to and known in the art as AMG317 (Corren et al., 2010, Am J Respir Crit Care Med., 181(8): 788-796), or any of the anti-IL-4Rα antibodies as set forth in U.S. Pat. Nos. 7,186,809, 7,605,237, 7,608,693, or 8,092,804. Additional anti-IL-4Rα antibodies that can be used herein include 4R34.1.19 as disclosed in Kim et al. (Sci Rep. 2019 May 23; 9(1):7772); CBP-201 (Connect Biopharma); and Medi9314, as disclosed in e.g., NCT02669667.

Anti-IL-4Rα antibodies useful in the presently-described methods can have pH-dependent binding characteristics. For example, an anti-IL-4Rα antibody can exhibit reduced binding to IL-4Rα at acidic pH as compared to neutral pH. Alternatively, an anti-IL-4Rα antibody can exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the KD value of the antibody binding to IL-4Rα at acidic pH to the KD value of the antibody binding to IL-4Rα at neutral pH (or vice versa). For example, an antibody or antigen-binding fragment thereof can be regarded as exhibiting "reduced binding to IL-4Rα at acidic pH as compared to neutral pH" for purposes of the present disclosure if the antibody or antigen-binding fragment thereof exhibits an acidic/neutral KD ratio of about 3.0 or greater. In certain instances, the acidic/neutral KD ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics can be obtained, e.g., by screening a population of antibodies for reduced (or enhanced) binding to a particular antigen at acidic pH as compared to neutral pH. Additionally, modifications of the antigen-binding domain at the amino acid level can yield antibodies with pH-dependent characteristics. For example, by substituting one or more amino acids of an antigen-binding domain (e.g., within a CDR) with a histidine residue, an antibody with reduced antigen-binding at acidic pH relative to neutral pH can be obtained. As used herein, the expression "acidic pH" means a pH of 6.0 or less.

II. Pharmaceutical Compositions

The present disclosure provides methods that include administering an anti-IL-4Rα antibody, such as dupilumab to a subject, wherein the antibody is an ingredient in a pharmaceutical composition. Useful pharmaceutical compositions can be formulated with suitable carriers, excipients, and other agents that provide suitable transfer, delivery, tolerance, and the like. A multitude of appropriate formulations can be found in the formulary Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311. Various delivery systems are known and can be used to administer a pharmaceutical composition, e.g., encapsulation in liposomes, microparticles, and microcapsules (see, e.g., Wu et al., 1987, J. Biol. Chem. 262:4429-4432).

Methods of administration include, but are not limited to, intradermal, intramuscular, intraperitoneal, intravenous, subcutaneous, intranasal, epidural, and oral routes. In some instances, administration is subcutaneous. The composition can be administered by any convenient route, for example by infusion or bolus injection, by absorption through epithelial or mucocutaneous linings (e.g., oral mucosa, rectal and intestinal mucosa, etc.) and can be administered together with other biologically active agents.

A pharmaceutical composition can be delivered subcutaneously or intravenously with a standard needle and syringe. With respect to subcutaneous delivery, a pen delivery device readily has applications in delivering a pharmaceutical composition in the presently described methods. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In some instances, a pump can be used. In some instances, polymeric materials can be used; see, Medical Applications of Controlled Release, Langer and Wise (eds.), 1974, CRC Pres., Boca Raton, Fla. In some instances, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

Injectable preparations are of particular use in the presently described methods. Injectable preparations can include dosage forms for intravenous, subcutaneous, intracutaneous and intramuscular injections, drip infusions, etc. These injectable preparations can be prepared using known methods. For example, injectable preparations can be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which can be used in combination with an appropriate solubilizing agent such as an alcohol (e.g., ethanol), a polyalcohol (e.g., propylene glycol, polyethylene glycol), a nonionic surfactant (e.g., polysorbate 80, HCO-50 (polyoxyethylene (50 mol) adduct of hydrogenated castor oil)}, etc. Useful oily media include, e.g., sesame oil and/or soybean oil, which can be used in combination with a solubilizing agent such as benzyl benzoate and/or benzyl alcohol. In some instances, the pharmaceutical composition is disposed in an appropriate ampoule.

Pharmaceutical compositions for oral or parenteral use described above can be prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions including an anti-IL-4Rα antibody that can be used in the context of the present disclosure are disclosed, e.g., in U.S. Pat. No. 8,945,559, the disclosure of which is incorporated herein by reference in its entirety.

III. Methods of Generating Anti-IL-4Rα Antibodies and Fragments

Methods for generating human antibodies in general include those described in, for example, U.S. Pat. No. 6,596,541, Green et al. (1994) Nature Genetics 7:13-21), U.S. Pat. Nos. 5,545,807; and 6,787,637, each of which is incorporated by reference in its entirety. Methods for generating an anti-IL-4Rα antibody that is particularly useful in the presently-described methods (e.g., method of generating dupilumab) are disclosed in U.S. Pat. No. 7,608,693, which is incorporated by reference in its entirety.

Methods of Identifying Disorders Treatable with Anti-IL-4Rα Antibodies

As discussed above, presently-described new indications that are treatable with an anti-IL-4Rα antibody were, at least in part, identified using computational drug repurposing methods. In some instances, the methods disclosed herein include identifying a disorder that is treatable with an anti-IL-4Rα antibody. In some instances, the methods of identifying a disorder include (a) selecting a characteristic or a plurality of characteristics related to an IL 4/IL 13 pathway in a set of data representing medical records of a plurality of subjects; (b) clustering, by a computer system, in accordance with the characteristic or the plurality of characteristics related to the IL-4/IL-13 pathway, a subset of subjects from the plurality of subjects, wherein the subset comprises the characteristic or the plurality of characteristics; (c) identifying in the subset clustered in step (b) the IL-4Rα-related disorder based on symptoms associated with the characteristic or the plurality of characteristics related to the IL-4/IL-13 pathway; and (d) selecting the subject having at least one symptom of, or determined to be susceptible to, an anti-interleukin-4 receptor alpha (IL-4Rα)-related disorder identified in step (c). In some instances, the IL-4Rα related disorder is not selected from the group consisting of atopic dermatitis, asthma, chronic rhinosinusitis with nasal polyposis, eosinophilic esophagitis, peanut allergy, grass allergy, chronic obstructive pulmonary disease (COPD), prurigo nodularis, bullous pemphigoid, chronic spontaneous urticaria (CSU) and allergic bronchopulmonary aspergillosis (ABPA). In some instances, the method further comprises administering a therapeutically effective amount of the anti-IL-4Rα antibody to the subject, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

A general description of the drug repurposing methods used for indications described herein is provided below.

I. Background

Drug repurposing can be used to find new clinical indications (e.g., a reason to use a drug) for clinically approved drugs. Guided by relevant clinical questions, powerful advanced analytics techniques can mine clinically relevant information hidden in large amounts of data, which can then assist clinical decision making.

Computational drug repurposing methods can use similarity measures (chemical similarity, molecular activity similarity, gene expression similarity, or side effect similarity), molecular docking, or shared molecular pathology to detect new drug-disease relationships. Drug repurposing approaches can be classified as network-based, text mining (literature search), and semantic approaches.

Data processing systems and methods generally described in this specification can be used to identify potential indications that have not been previously identified using conventional techniques.

In the following description, for the purposes of explanation, numerous specific details are set forth in order to provide a thorough understanding of the present disclosure. It will be apparent, however, that the present disclosure may be practiced without these specific details. In other instances, well-known structures and devices are shown in block diagram form in order to avoid unnecessarily obscuring the present disclosure.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all implementations or that the features represented by such element may not be included in or combined with other elements in some implementations.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described hereafter that can each be used independently of one another or with any combination of other features. However, any individual feature may not address any of the problems discussed above or might only address one of the problems discussed above. Some of the problems discussed above might not be fully addressed by any of the features described in this specification. Although headings are provided, data related to a particular heading, but not found in the section having that heading, may also be found elsewhere in this description.

II. Example Data Processing Systems and Methods

FIG. 1 shows an example of a data processing system 100. In some implementations, the data processing system 100 is configured to process data that can represent medical records of a plurality of patients to identify new indications of a drug (the drug for repurposing). The system 100 includes computer processors 110. The computer processors 110 include computer-readable memory 111 and computer readable instructions 112. The system 100 also includes a machine learning system 150. The machine learning system 150 includes a machine learning model 120. The machine learning model 120 can be separate from or integrated with the computer processors 110.

The computer-readable medium 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable medium 111 includes code-segment having executable instructions.

In some implementations, the computer processors 110 include a general purpose processor. In some implementations, the computer processors 110 include a central processing unit (CPU). In some implementations, the computer processors 110 include at least one application specific integrated circuit (ASIC). The computer processors 110 can also include general purpose programmable microprocessors, graphic processing units, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code such as the computer-executable instructions 112 and configured to execute executable logic that includes the machine learning model 120.

The computer processors 110 are configured to receive data representing medical records of a plurality of patients. For example, the computer processors 110 can receive data from a database that includes electronic medical records (EMRs) data for approximately 94 million patients (or more) identifiable by a key identifier (ID) that allows matching of patients across different data tables. In some implementations, the data indicates diagnosis, lab test, procedures, medications, patient events, insurance, biomarkers, measurements, clinical status, lifestyle parameters, microbiology, prescriptions, and so forth. In some implementations, the data includes natural language process driven data. The data can be received through any of various techniques, such as wireless communications, optical fiber communications, USB, CD-ROM, and so forth.

The machine learning system 150 is capable of applying machine learning techniques to train the machine learning model 120. As part of the training of the machine learning model 120, the machine learning system 150 can form a training set of input data by identifying a positive training set of input data items that have been determined to have the property in question, and, in some implementations, can form a negative training set of input data items that lack the property in question.

The machine learning system 150 extracts feature values from the input data of the training set, the features being variables deemed potentially relevant to whether or not the input data items have the associated property or properties. An ordered list of the features for the input data is herein referred to as the feature vector for the input data. In some implementations, the machine learning system 150 applies dimensionality reduction to reduce the amount of data in the feature vectors for the input data to a smaller, more representative set of data. For example, the machine learning system 150 can apply Multiple Correspondence Analysis (MCA), linear discriminant analysis (LDA), principle component analysis (PCA), and so forth.

In some implementations, the machine learning system 150 uses unsupervised machine learning to train the machine learning model 120. Typically, unsupervised machine learning techniques make inferences from datasets using input vectors without referring to known, or labelled, outcomes. In some implementations, the machine learning system 150 can perform clustering to divide data points into a number of groups such that the data points in the same group are more similar to other data points in the same group and dissimilar to data points in other groups. In some implementations, clustering includes performing K-means clustering, in which a one-level unnested partitioning of data points is created by iteratively partitioning the data set. That is, if K is the desired number of clusters, in each iteration, the data set is partitioned into K disjoint clusters. The processes can be continued until a specified clustering criterion function value is optimized. In some implementations, the machine learning system 150 is configured to perform bisecting K-means clustering. Bisecting k-means clustering typically involves splitting one cluster into two subclusters at each bisecting step (e.g., by using k-means) until k clusters are obtained. Bisecting K-means clustering may be more beneficial when compared to K-means clustering, as bisecting K-means clustering can reduce computation time when K is a relatively large value, can produce clusters of similar size, and can produce clusters with smaller entropy.

The computer processors 110 are configured to execute the computer-executable instructions 112 to perform one or more operations. In some implementations, the one or more operations include receiving data representing medical records of a plurality of patients. For example, the computer processors 110 can receive data from a database that includes electronic medical records (EMRs) for approximately 94 million patients (or more) identifiable by a key identifier (ID) that allows matching of patients across different data tables. In some implementations, the data indicates diagnosis, lab test, procedures, medications, patient events, insurance, biomarkers, measurements, clinical status, lifestyle parameters, microbiology, prescriptions, and so forth. In some implementations, the data includes natural language process driven data. The data can be received through any of various techniques, such as wireless communications, optical fiber communications, USB, CD-ROM, and so forth.

In some implementations, the one or more operations include selecting, based on the medical records, a set of patients. Selection of the set of patients includes determining at least one target signaling pathway associated with a drug for repurposing. For example, if the drug is dupilumab, the computer processors 110 can determine that the drug modulates the interleukin-4 (IL-4) and interleukin-13 (IL-13) signaling pathway based on known functions of the drug. Selecting the set of patients also includes determining one or more indicators based on one or more factors corresponding to a diagnosis linked to the target signaling pathway. For example, factors such as pathway mechanisms, related clinical conditions, therapeutic analogues, data and epidemiology, and pharmaceutical life-cycle management alignment can be used to search through sources that include medical databases and medical evidence software to identify diseases linked to the determined signaling pathway. These diseases can be categorized based on the strength of the link to the determined signaling pathway. The categories can include a focused group, a medium group, and a broad group. For example, returning to the IL-4/IL-13 example, a focused group of diseases can include diseases that have a direct relationship with the IL-4/IL-13 mechanism of action on the Th2 pathway, a medium group of diseases can include diseases that have an indirect relationship with the IL-4/IL-13 mechanism of action on the Th2 pathway, and a broad group of diseases can include diseases associated with a broader inflammatory response. Moving from the focus group to the broad group can increase the number of indicators to be considered when selecting the set of patients, and can reduce the likelihood of molecule impact. Accordingly, in some implementations, only the focused group, or the focused and medium group, are used to select the set of patients. In some implementations, only patients with at least one diagnosis, medication, lab test, and/or procedure associated with the determined signaling pathway are selected for inclusion into the set of patients. A detailed example of factors and indicators is provided later with reference to Table 7.

In some implementations, the one or more operations include determining a plurality of patient characteristics (sometimes referred to as features in this specification) of the set of patients, in which each patient of the set of patients exhibits at least one of the plurality of patient characteristics. Determining the plurality of patient characteristics can include analyzing the initially received data to identify broad patient characteristics to capture all or a substantial portion of the received data. For example, the broad patient characteristics can correspond to diagnoses (e.g., immuno-conditions, diabetes), prescriptions (e.g., immuno-drugs, other drug classes), procedures (e.g., human leukocyte antigen typing), and laboratory results (e.g., IgE abnormal high/low). In some implementations, determining the plurality of patient characteristics includes receiving user input (e.g., through a user interface in communication with the computer processors 110). For example, a user can input patient characteristics based on clinical input, demographics, medication, comorbidities, procedures, and laboratory tests data specific to immunology. Bespoke characteristic classes may also be added to increase data completeness, representativeness, and to collect more information on diseases and drug response. In some implementations, determining the plurality of patient characteristics includes validating the plurality of patient characteristics. Validating can include determining whether the patient characteristics of the initially received data are mapped correctly to the selected set of patients by calculating the percentage of selected patients with at least one of each characteristic family (e.g., the percentage of patients with a prescription record) and comparing this percentage to the percentage of patients of the initially received data with at least one of each characteristic family. The two numbers being closer in value indicates that the mapping has been done correctly. Validating can include determining whether the patient characteristics have been mapped to the correct patient by identifying a number of patients that are included in both the initially received data and the selected set of patients to verify identical mapping of patient characteristics between the patients of the initially received data and the selected set of patients.

In some implementations, the one or more operations include grouping, in accordance with the plurality of patient characteristics (e.g., as defined by features related to the determined signaling pathway), the set of patients to generate a plurality of distinct groups in which each of the distinct groups include at least one patient of the set of patients. For example, the one or more computer processors 110 can execute the machine learning model 120 to perform a clustering technique, such as the bisecting k-means clustering technique described above. The clustering can result in a plurality of clusters (e.g., distinct groups) of patients in which patients in one cluster are more similar to each other than patients in other clusters with respect to their corresponding patient characteristics. In some implementations, the generated clusters may show correlations among patient characteristics, even if they weren't present in the same patient. Clinical inputs can be received and used in various stages of the clustering process to ensure the clinical relevance of the resulting clusters. For example, disease experts' clinical inputs can facilitate the creation of clinically relevant cohorts, in the inclusion and grouping of clinically relevant features, and in validating and assessing the clusters. Patient characteristics can be identified as being distinctive in clusters if they occurred more frequently than in the general population (e.g., overall in the selected set of patients).

In some implementations, Multiple Correspondence Analysis (MCA) is used to reduce the dimensions of the patient characteristics. Bisecting K-means can facilitate an appropriate and effective separation of patients with sufficiently "tight" but stable clusters, and allow a large number of clusters that exhibited immuno-relatedness to be used for scoring the patient characteristics, which is explained later in more detail. The resulting clusters can be presented (e.g., through a user interface) to users (e.g., clinical experts) for validation and assessment. This can reduce the risk of non-interpretability of the clusters and to ensure the absence of overlapping features between the different clusters.

In some implementations, the one or more operations include selecting, based on one or more group selection criteria, a set of distinct groups of the plurality of distinct groups. In some implementations, selecting the set of distinct groups includes ranking the groups and selecting a number of the most highly ranked groups (e.g., the top 60 ranked groups). The groups can be ranked based on immunology enrichment, stability, purity, and size. In some implementations, one or more measures (sometimes referred to as feature scores in this specification) are calculated for each patient characteristic to rank the clusters. The one or more measures can include, for example, distinctiveness (sometimes referred to as "lift score" in this specification), the number of patients within a cluster that present the patient characteristic, and an immunology score. The distinctiveness score measure how distinctive a patient characteristic is within a cluster versus the rest of the population (e.g., if males represent 50% of the population and 75% of the cluster, then the "lift score" can be equal to 1.5). In some implementations, only patient characteristics with a lift score that exceeds a threshold lift score (e.g., 1) and appearing in a percentage of patients that exceed a threshold percentage of patients (e.g., 10%) are considered to define clusters and correspond to a theme of the clusters. Patient characteristics that are considered to define a cluster may be referred to as potentially relevant patient characteristics in this specification. The patient characteristics (e.g., either the patient characteristics considered to define clusters or all of the patient characteristics) can then be given an immunology score, which scores the patient characteristics according to its type (e.g., disease, drug, laboratory test, procedure, and so forth) and immunology relevance. The patient characteristic scores within each cluster can then be aggregated (e.g., summed) and normalized. Clusters meeting a threshold cluster score (e.g., 50%) can then be considered as immunology-specific.

Selecting the set of distinct groups can include assessing one or more of the stability, purity, and the number of patients within each cluster. Stability can be assessed using one or more of the following methods: (1) reproducing the clusters on different sizes of data; (2) changing the initializing seeds of the clusters; (3) changing the number of clusters produced and (4) applying a training-test method. For each cluster in the training set, stability can be defined as the maximum proportion of patients that are also grouped together in the test set. Purity can be measured by the intra-cluster variance of MCA components of patients within a cluster, which can result in homogenous and dense clusters. In some implementations, a cluster is selected if it exceeds a threshold stability percentage (e.g., 50%) and exceeds a threshold purity percentage (e.g., the cluster is in the highest 20% of purity among all clusters).

In some implementations, the one or more operations include identifying one or more relevant patient characteristics (e.g., indications) by analyzing each distinct group of the set of distinct groups. Identifying one or more relevant patient characteristics can include ranking the patient characteristics presented by each selected cluster (e.g., all of the patient characteristics or the patient characteristics considered to define a cluster). The ranking can be based on the frequency of co-occurrence with each a number of established (reference) characteristics (referential) of the drug for repurposing (e.g., if the drug is Dupilumab, the reference characteristics may include asthma, atopic dermatitis, IgE allergy, and a composite immunology score). The co-occurrence can be measured by calculating the proportion of patient-weighted clusters that contain both the patient characteristic and the referential. In some implementations, one or more patient characteristics judged by subject-matter experts as relevant to the core cluster theme (e.g., as indicated by user input received through a user interface) can also be considered for evaluation, regardless of the number of patients in which these features appeared (might be <10%).

Identifying one or more patient characteristics can include assessing clinical and commercial feasibility of the patient characteristics. For example, patient characteristics that show a distinct clinical diagnosis can be identified. Commercial assessment can be based on data indicating forecast sales and competitor assets were available, a determined link to the targeted signal pathway (whether found or not in publications), worldwide prevalence of the patient characteristic, and the disability-adjusted life year (DALY) of the patient characteristic (e.g., per 100,000 life years). As a result, in some implementations, the one or more operations generally output new indications for the drug for repurposing.

While this specification here generally describes a patient as a human patient, implementations are not so limited. For example, a patient can refer to a non-human animal.

Figure 2:
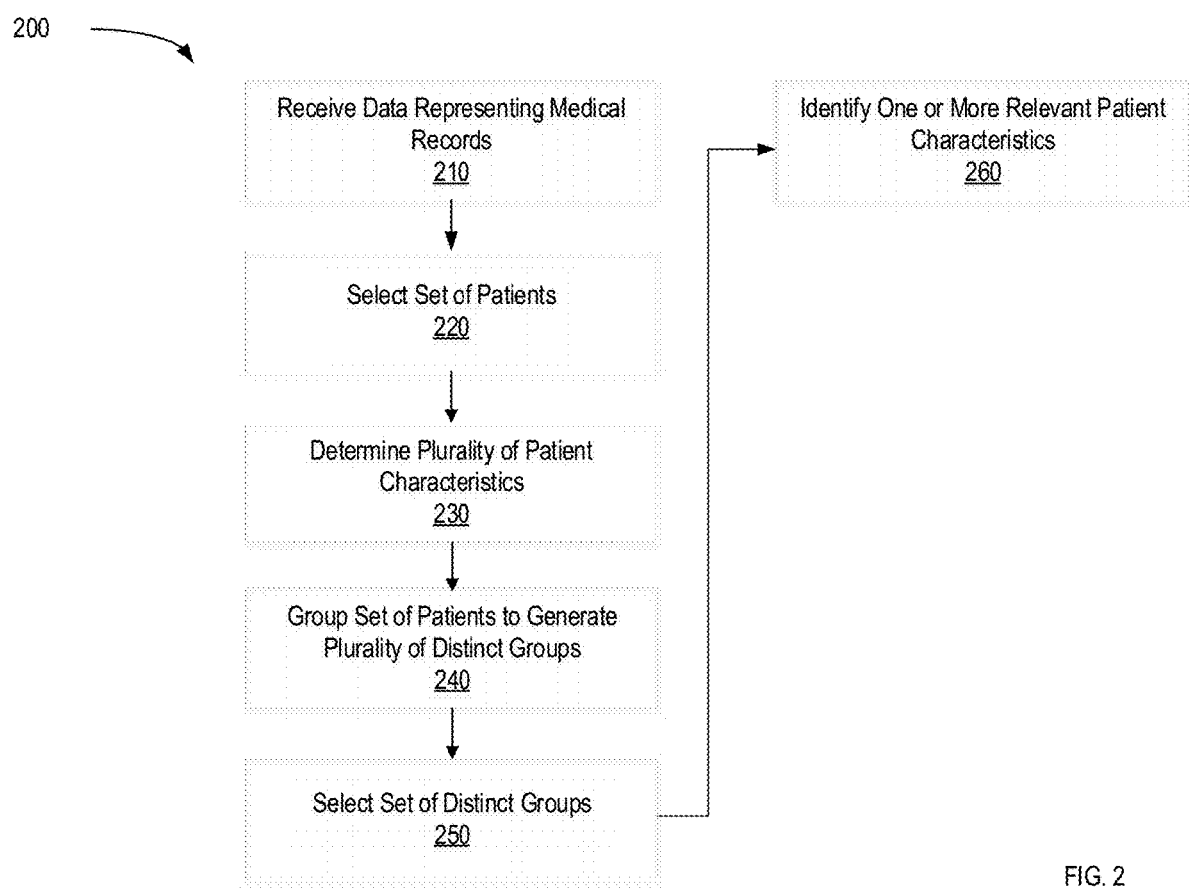
FIG. 2 is a flow chart illustrating an example method for repurposing drugs.

FIG. 2 is a flow chart illustrating an example method 200 for repurposing drugs. The method 200 can be performed by the data processing system 100 described previously with reference to FIG. 1. The method 200 includes receiving data representing medical records (block 210), selecting a set of patients (block 220), determining a plurality of patient characteristics (block 230), grouping the set of patients to generate a plurality of distinct groups (block 240), selecting a set of distinct groups (block 250), and identifying one or more relevant patient characteristics (block 260).

At block 210, data representing medical records of a plurality of patients is received. The data can be received from, for example, a database that includes EMRs for approximately 94 million patients (or more) identifiable by a key ID that allows matching of patients across different data tables. In some implementations, the data indicates diagnosis, lab test, procedures, medications, patient events, insurance, biomarkers, measurements, clinical status, lifestyle parameters, microbiology, prescriptions, and so forth. In some implementations, the data includes natural language process driven data. The data can be received through any of various techniques, such as wireless communications, optical fiber communications, USB, CD-ROM, and so forth.

At block 220, at least one target signaling pathway associated with the drug for repurposing is determined. For example, if the drug is dupilumab, it can be determined that the drug modulates the IL-4 and IL-13 signaling pathway based on known functions of the drug. In some implementations, one or more indicators are determined based on one or more factors corresponding to a diagnosis linked to the target signaling pathway. For example, factors such as pathway mechanisms, related clinical conditions, therapeutic analogues, data and epidemiology, and pharmaceutical life-cycle management alignment can be used to search through sources that include medical databases and medical evidence software to identify diseases linked to the determined signaling pathway. These diseases can be categorized based on the strength of the link to the determined signaling pathway. The categories can include a focused group, a medium group, and a broad group. For example, returning to the IL-4/IL-13 example, a focused group of diseases can include diseases that have a direct relationship with the IL-4/IL-13 mechanism of action on the Th2 pathway, a medium lens group of diseases can include diseases that have indirect relationship with the IL-4/IL-13 mechanism of action on the Th2 pathway, and a broad group of diseases can include diseases associated with a broader inflammatory response. Moving from the focus group to the broad group can increase the number of indicators to be considered when selecting the set of patients, and can reduce the likelihood of molecule impact. Accordingly, in some implementations, only the focused group, or the focused and medium group, are used to select the set of patients. In some implementations, only patients with at least one diagnosis, medication, lab test, and/or procedure associated with the determined signaling pathway are selected for inclusion into the set of patients.

At block 230, a plurality of patient characteristics of the set of patients is determined, in which each patient of the set of patients exhibits at least one of the plurality of patient characteristics. Determining the plurality of patient characteristics can include analyzing the initially received data to identify broad patient characteristics to capture all or a substantial portion of the received data. For example, the broad patient characteristics can correspond to diagnoses (e.g., immuno-conditions, diabetes), prescriptions (e.g., immuno-drugs, other drug classes), procedures (e.g., human leukocyte antigen typing), and laboratory results (e.g., IgE abnormal high/low). In some implementations, determining the plurality of patient characteristics includes receiving user input (e.g., through a user interface). For example, a user can input patient characteristics based on clinical input and demographics, medication, comorbidities, procedures and laboratory tests data specific to immunology. Bespoke characteristic classes may also be added to increase data completeness, representativeness, and to collect more information on diseases and drug response. In some implementations, determining the plurality of patient characteristics includes validating the plurality of patient characteristics. Validating can include determining whether the patient characteristics of the initially received data are mapped correctly to the selected set of patients by calculating the percentage of selected patients with at least one of each characteristic family (e.g., the percentage of patients with a prescription record) and comparing this percentage to the percentage of patients of the initially received data with at least one of each characteristic family. The two numbers being closer in value indicates that the mapping has been done correctly. Validating can include determining whether the patient characteristics have been mapped to the correct patient by identifying a number of patients that are included in both the initially received data and the selected set of patients to verify identical mapping of patient characteristics between the patients of the initially received data and the selected set of patients.

At block 240, the set of patients are grouped in accordance with the plurality of patient characteristics (e.g., as defined by features related to the determined signaling pathway) to generate a plurality of distinct groups in which each of the distinct groups include at least one patient of the set of patients. For example, clustering techniques, such as the bisecting k-means clustering technique described above, can be performed on the set of patients using the plurality of patient characteristics. The clustering can result in a plurality of clusters (e.g., distinct groups) of patients in which patients in one cluster are more similar to each other than patients in other clusters with respect to their corresponding patient characteristics. In some implementations, the generated clusters may show correlations among patient characteristics, even if they weren't present in the same patient. Clinical inputs can be received and used in various stages of the clustering process to ensure the clinical relevance of the resulting clusters. For example, disease experts' clinical inputs can facilitate the creation of clinically relevant cohorts, in the inclusion and grouping of clinically relevant features, and in validating and assessing the clusters. Patient characteristics can be identified as being distinctive in clusters if they occurred more frequently than in the general population (e.g., overall in the selected set of patients).

In some implementations, Multiple Correspondence Analysis (MCA) is used to reduce the dimensions of the patient characteristics. Bisecting K-means can facilitate an appropriate and effective separation of patients with sufficiently "tight" but stable clusters, and allow a large number of clusters that exhibited immuno-relatedness to be used for scoring the patient characteristics, which is explained later in more detail. The resulting clusters can be presented (e.g., through a user interface) to users (e.g., clinical experts) for validation and assessment. This can reduce the risk of non-interpretability of the clusters and to ensure the absence of overlapping features between the different clusters.

At block 250, a set of distinct groups of the plurality of distinct groups is selected based on or more group selection criteria. In some implementations, selecting the set of distinct groups includes ranking the groups and selecting a number of the most highly ranked groups (e.g., the top 60 ranked groups). The groups can be ranked based on immunology enrichment, stability, purity, and size. In some implementations, one or more measures are calculated for each patient characteristic to rank the clusters. The one or more measures can include, for example, distinctiveness (sometimes referred to as "lift score" in this specification), the number of patients within a cluster that present the patient characteristic, and an immunology score. The distinctiveness score measure how distinctive a patient characteristic is within a cluster versus the rest of the population (e.g., if males represent 50% of the population and 75% of the cluster, then the "lift score" can be equal to 1.5). In some implementations, only patient characteristics with a lift score that exceeds a threshold lift score (e.g., 1) and appearing in a percentage of patients that exceed a threshold percentage of patients (e.g., 10%) are considered to define clusters and correspond to a theme of the clusters. Patient characteristics that are considered to define a cluster may be referred to as potentially relevant patient characteristics in this specification. The patient characteristics (e.g., either the considered patient characteristics for defining clusters or all of the patient characteristics) can then be given an immunology score, which scores the patient characteristics according to its type (e.g., disease, drug, laboratory test, procedure, and so forth) and immunology relevance. The patient characteristic scores within each cluster can then be aggregated (e.g., summed) and normalized. Clusters meeting a threshold cluster score (e.g., 50%) can then be considered as immunology-specific.

Selecting the set of distinct groups can include assessing one or more of the stability, purity, and the number of patients within each cluster. Stability can be assessed using one or more of the following methods: (1) reproducing the clusters on different sizes of data; (2) changing the initializing seeds of the clusters; (3) changing the number of clusters produced and (4) applying a training-test method. For each cluster in the training set, stability can be defined as the maximum proportion of patients that are also grouped together in the test set. Purity can be measured by the intra-cluster variance of MCA components of patients within a cluster, which can result in homogenous and dense clusters. In some implementations, a cluster is selected if it exceeds a threshold stability percentage (e.g., 50%) and exceeds a threshold purity percentage (e.g., the cluster is in the highest 20% of purity among all clusters).

At block 260, one or more relevant patient characteristics are identified by analyzing each distinct group of the set of distinct groups. Identifying one or more relevant patient characteristics can include ranking the patient characteristics presented by each selected cluster (e.g., all of the patient characteristics or the patient characteristics considered to define a cluster). The ranking can be based on the frequency of co-occurrence with each a number of established (reference) characteristics (referential) of the drug for repurposing (e.g., if the drug is Dupilumab, the reference characteristics may include asthma, atopic dermatitis, IgE allergy, and a composite immunology score). The co-occurrence can be measured by calculating the proportion of patient-weighted clusters that contain both the patient characteristic and the referential. In some implementations, one or more patient characteristics judged by subject-matter experts as relevant to the core cluster theme (e.g., as indicated by user input received through a user interface) can also be considered for evaluation, regardless of the number of patients in which these features appeared (might be <10%).

Identifying one or more patient characteristics can include assessing clinical and commercial feasibility of the patient characteristics. For example, patient characteristics that show a distinct clinical diagnosis can be identified. Commercial assessment can be based on data indicating forecast sales and competitor assets were available, a determined link to the targeted signal pathway (whether found or not in publications), worldwide prevalence of the patient characteristic, and the disability-adjusted life year (DALY) of the patient characteristic (e.g., per 100,000 life years).

Figure 5:
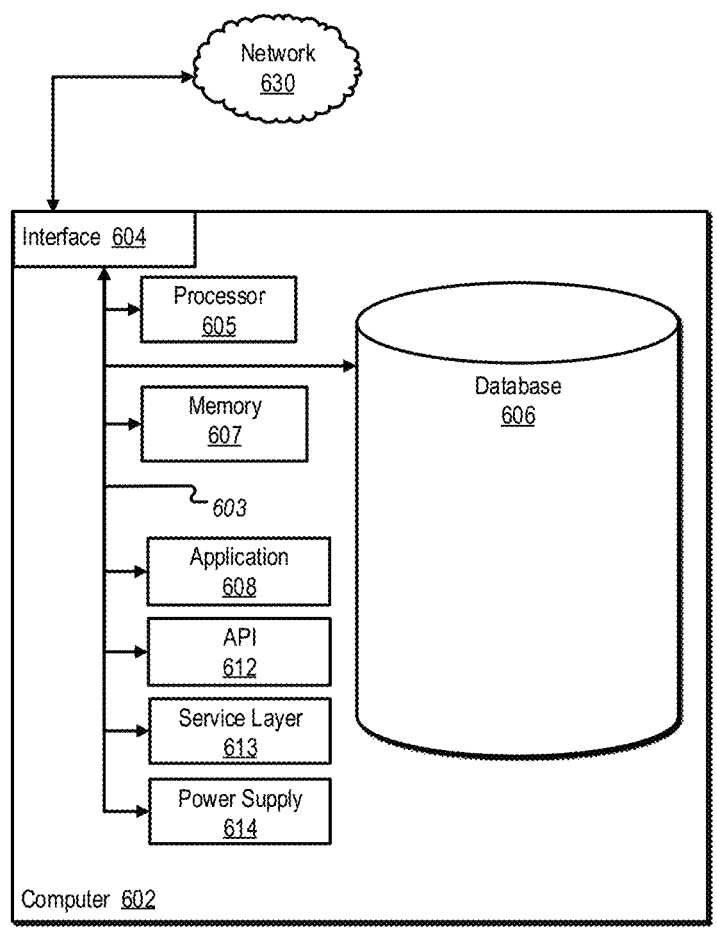
FIG. 5 is a block diagram of an example computer system used to provide computational functionalities associated with described algorithms, methods, functions, processes, flows, and procedures described in the present disclosure.
Figure 7A:
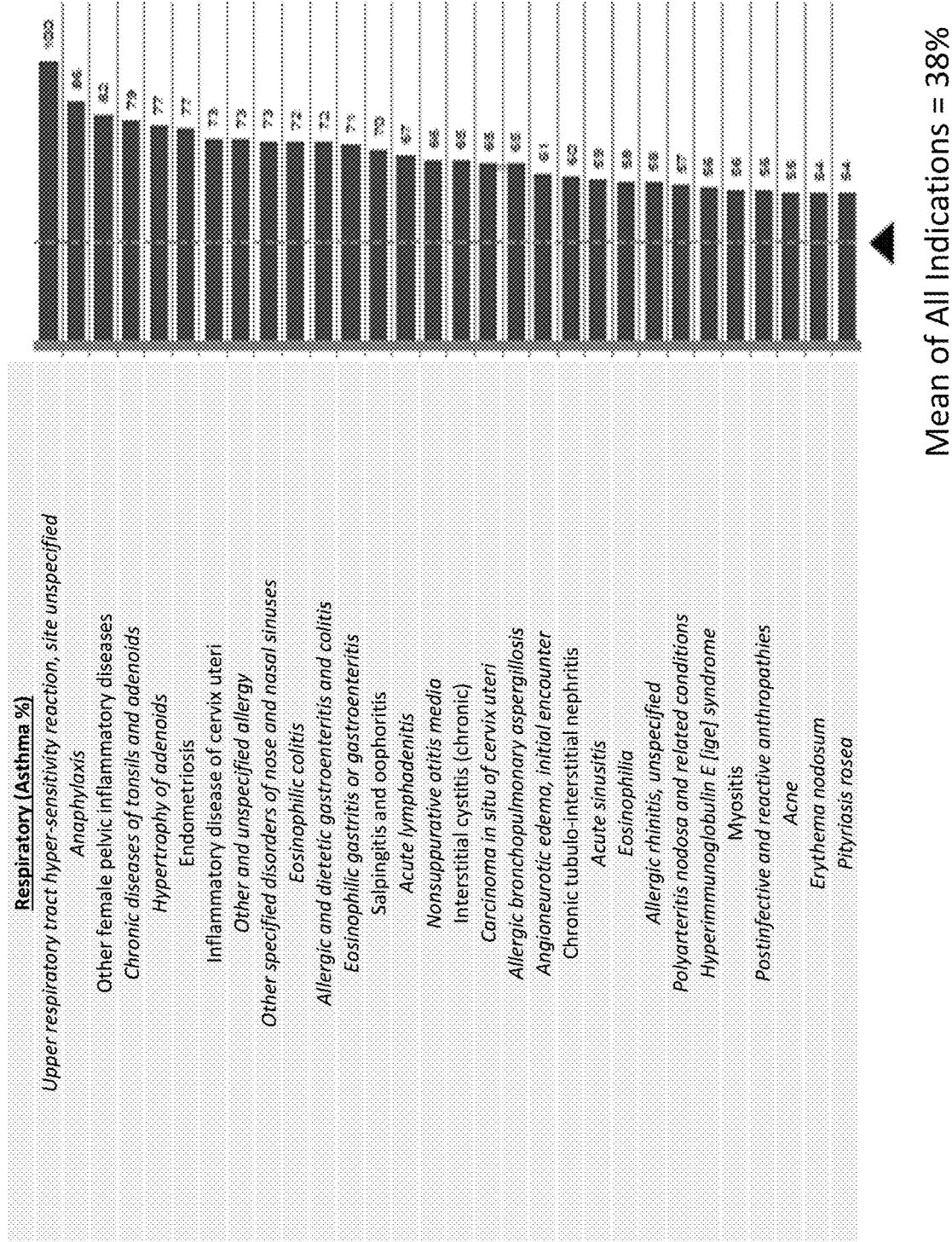
Figure 7B:
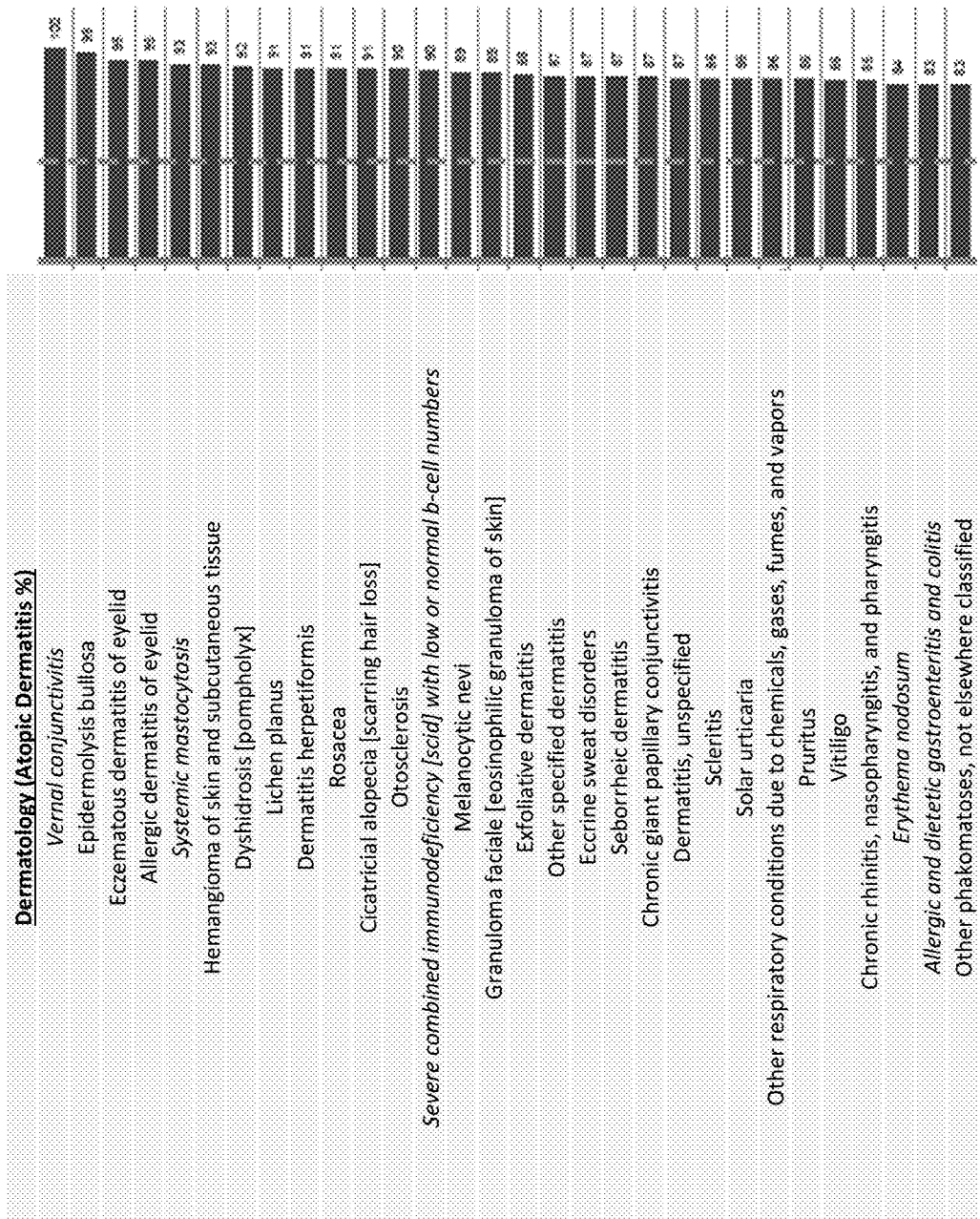
Figure 7C:
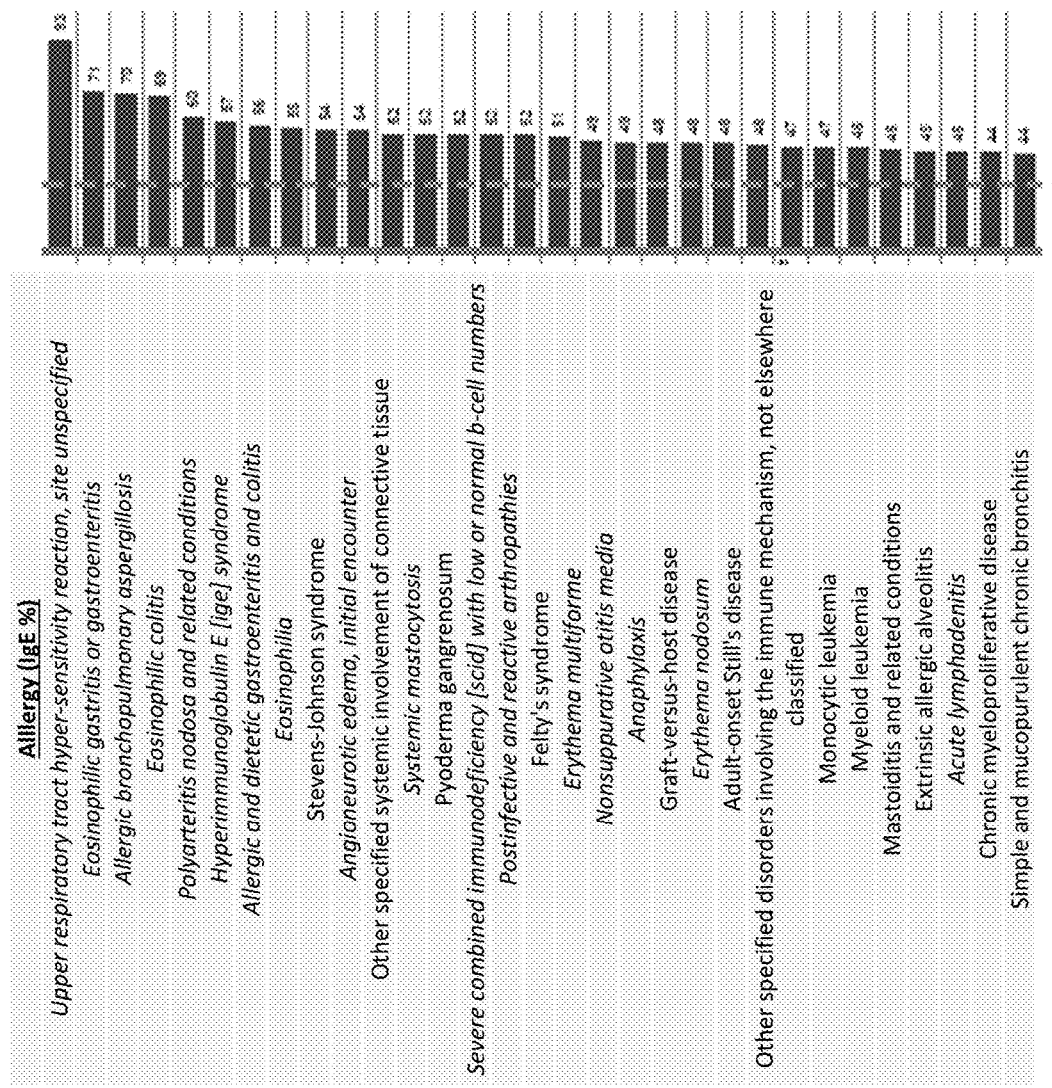

FIG. 5 is a block diagram of an example computer system 600 used to provide computational functionalities associated with described algorithms, methods, functions, processes, flows, and procedures described in the present disclosure (such as the method 200 described previously with reference to FIG. 2), according to some implementations of the present disclosure. The illustrated computer 602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 602 can include input devices such as keypads, keyboards, and touch screens that can accept user information. Also, the computer 602 can include output devices that can convey information associated with the operation of the computer 602. The information can include digital data, visual data, audio information, or a combination of information. The information can be presented in a graphical user interface (UI) (or GUI).

The computer 602 can serve in a role as a client, a network component, a server, a database, a persistency, or components of a computer system for performing the subject matter described in the present disclosure. The illustrated computer 602 is communicably coupled with a network 630. In some implementations, one or more components of the computer 602 can be configured to operate within different environments, including cloud-computing-based environments, local environments, global environments, and combinations of environments.

At a high level, the computer 602 is an electronic computing device operable to receive, transmit, process, store, and manage data and information associated with the described subject matter. According to some implementations, the computer 602 can also include, or be communicably coupled with, an application server, an email server, a web server, a caching server, a streaming data server, or a combination of servers.

The computer 602 can receive requests over network 630 from a client application (for example, executing on another computer 602). The computer 602 can respond to the received requests by processing the received requests using software applications. Requests can also be sent to the computer 602 from internal users (for example, from a command console), external (or third) parties, automated applications, entities, individuals, systems, and computers.

Each of the components of the computer 602 can communicate using a system bus 603. In some implementations, any or all of the components of the computer 602, including hardware or software components, can interface with each other or the interface 604 (or a combination of both), over the system bus 603. Interfaces can use an application programming interface (API) 612, a service layer 613, or a combination of the API 612 and service layer 613. The API 612 can include specifications for routines, data structures, and object classes. The API 612 can be either computer-language independent or dependent. The API 612 can refer to a complete interface, a single function, or a set of APIs.

The service layer 613 can provide software services to the computer 602 and other components (whether illustrated or not) that are communicably coupled to the computer 602. The functionality of the computer 602 can be accessible for all service consumers using this service layer. Software services, such as those provided by the service layer 613, can provide reusable, defined functionalities through a defined interface. For example, the interface can be software written in JAVA, C++, or a language providing data in extensible markup language (XML) format. While illustrated as an integrated component of the computer 602, in alternative implementations, the API 612 or the service layer 613 can be stand-alone components in relation to other components of the computer 602 and other components communicably coupled to the computer 602. Moreover, any or all parts of the API 612 or the service layer 613 can be implemented as child or sub-modules of another software module, enterprise application, or hardware module without departing from the scope of the present disclosure.

The computer 602 includes an interface 604. Although illustrated as a single interface 604 in FIG. 5, two or more interfaces 604 can be used according to particular needs, desires, or particular implementations of the computer 602 and the described functionality. The interface 604 can be used by the computer 602 for communicating with other systems that are connected to the network 630 (whether illustrated or not) in a distributed environment. Generally, the interface 604 can include, or be implemented using, logic encoded in software or hardware (or a combination of software and hardware) operable to communicate with the network 630. More specifically, the interface 604 can include software supporting one or more communication protocols associated with communications. As such, the network 630 or the interface's hardware can be operable to communicate physical signals within and outside of the illustrated computer 602.

The computer 602 includes a processor 605. Although illustrated as a single processor 605 in FIG. 5, two or more processors 605 can be used according to particular needs, desires, or particular implementations of the computer 602 and the described functionality. Generally, the processor 605 can execute instructions and can manipulate data to perform the operations of the computer 602, including operations using algorithms, methods, functions, processes, flows, and procedures as described in the present disclosure.

The computer 602 also includes a database 606 that can hold data for the computer 602 and other components connected to the network 630 (whether illustrated or not). For example, database 606 can be an in-memory, conventional, or a database storing data consistent with the present disclosure. In some implementations, database 606 can be a combination of two or more different database types (for example, hybrid in-memory and conventional databases) according to particular needs, desires, or particular implementations of the computer 602 and the described functionality. Although illustrated as a single database 606 in FIG. 5, two or more databases (of the same, different, or combination of types) can be used according to particular needs, desires, or particular implementations of the computer 602 and the described functionality. While database 606 is illustrated as an internal component of the computer 602, in alternative implementations, database 606 can be external to the computer 602.

The computer 602 also includes a memory 607 that can hold data for the computer 602 or a combination of components connected to the network 630 (whether illustrated or not). Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 5, two or more memories 607 (of the same, different, or combination of types) can be used according to particular needs, desires, or particular implementations of the computer 602 and the described functionality. While memory 607 is illustrated as an internal component of the computer 602, in alternative implementations, memory 607 can be external to the computer 602.

The application 608 can be an algorithmic software engine providing functionality according to particular needs, desires, or particular implementations of the computer 602 and the described functionality. For example, application 608 can serve as one or more components, modules, or applications. Further, although illustrated as a single application 608, the application 608 can be implemented as multiple applications 608 on the computer 602. In addition, although illustrated as internal to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion and management circuits, including recharging, standby, and power management functionalities. In some implementations, the power-supply 614 can include a power plug to allow the computer 602 to be plugged into a wall socket or a power source to, for example, power the computer 602 or recharge a rechargeable battery.

There can be any number of computers 602 associated with, or external to, a computer system containing computer 602, with each computer 602 communicating over network 630. Further, the terms "client," "user," and other appropriate terminology can be used interchangeably, as appropriate, without departing from the scope of the present disclosure. Moreover, the present disclosure contemplates that many users can use one computer 602 and one user can use multiple computers 602.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component (for example, as a data server), or that includes a middleware component (for example, an application server). Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

Administration of Anti-IL-4Rα Antibodies and Fragments

The present disclosure provides methods of treating specific disorders with therapeutic compositions including an anti-IL-4R antibody (e.g., an anti-IL-4Rα antibody, e.g., dupilumab) or fragment thereof. The present disclosure also provides an anti-IL-4R antibody (e.g., an anti-IL-4Rα antibody, e.g., dupilumab) or fragment thereof for use in methods of treating specific disorders with therapeutic compositions.

The methods used herein are useful for treating a subject in need thereof. As used herein, the terms "subject," "patient," and the like are used interchangeably.

In some embodiments, disclosed herein are methods of treating a subject exhibiting at least one symptom of, or determined to be susceptible to, an anti-interleukin-4 receptor alpha (IL-4Rα)-related disorder with an anti-interleukin-4 receptor antibody. In some instances, the methods include administering a therapeutically effective amount of the anti-IL-4Rα antibody to a subject exhibiting at least one symptom of, or determined to be susceptible to, an anti-interleukin-4 receptor alpha (IL-4Rα)-related disorder, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

In some instances, the methods include (a) identifying a subject for treatment with an anti-IL-4Rα antibody and (b) administering a therapeutically effective amount of the anti-IL-4Rα antibody to the subject, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, identifying the subject for treatment includes (a) selecting a characteristic or a plurality of characteristics in a set of patients; (b) clustering, by a computer system, in accordance with the characteristic or the plurality of characteristics, a subset of patients having the characteristic or the plurality of characteristics, wherein the characteristic or the plurality of characteristics are associated with at least one symptom of, or determined to be susceptible to, the IL-4Rα-related disorder; (c) identifying in the subset of patients clustered in step (b) the IL-4Rα-related disorder based on the symptoms associated with the characteristic or the plurality of characteristics related to the IL-4/IL-13 pathway; and (d) selecting the subject exhibiting at least one symptom of, or determined to be susceptible to, an anti-interleukin-4 receptor alpha (IL-4Rα)-related disorder identified in step (c).

In some instances, the methods include identifying a subject as a candidate for treatment for an anti-interleukin-4 receptor alpha (IL-4Rα)-related disorder with an anti-IL-4Rα antibody comprising (a) selecting a characteristic or a plurality of characteristics related to an IL 4/IL 13 pathway in a set of data representing medical records of a plurality of subjects; (b) clustering, by a computer system, in accordance with the characteristic or the plurality of characteristics related to the IL-4/IL-13 pathway, a subset of subjects from the plurality of subjects, wherein the subset comprises the characteristic or the plurality of characteristics; (c) identifying in the subset clustered in step (b) the IL-4Rα-related disorder based on symptoms associated with the characteristic or the plurality of characteristics related to the IL-4/IL-13 pathway; and (d) selecting the subject having at least one symptom of, or determined to be susceptible to, an anti-interleukin-4 receptor alpha (IL-4Rα)-related disorder identified in step (c) with the proviso that the IL-4Rα related disorder is not selected from the group consisting of atopic dermatitis, asthma, chronic rhinosinusitis with nasal polyposis, eosinophilic esophagitis, peanut allergy, grass allergy, chronic obstructive pulmonary disease (COPD), prurigo nodularis, bullous pemphigoid, chronic spontaneous urticaria (CSU) and allergic bronchopulmonary aspergillosis (ABPA).

In some instances, the methods include identifying a subject as a candidate for treatment for an anti-interleukin-4 receptor alpha (IL-4Rα)-related disorder with an anti-IL-4Rα antibody comprising (a) selecting a characteristic or a plurality of characteristics related to an IL 4/IL 13 pathway in a set of data representing medical records of a plurality of subjects; (b) clustering, by a computer system, in accordance with the characteristic or the plurality of characteristics related to the IL-4/IL-13 pathway, a subset of subjects from the plurality of subjects, wherein the subset comprises the characteristic or the plurality of characteristics; (c) identifying in the subset clustered in step (b) the IL-4Rα-related disorder based on symptoms associated with the characteristic or the plurality of characteristics related to the IL-4/IL-13 pathway; and (d) selecting the subject having at least one symptom of, or determined to be susceptible to, an anti-interleukin-4 receptor alpha (IL-4Rα)-related disorder identified in step (c). In some instances, the method further comprises administering a therapeutically effective amount of the anti-IL-4Rα antibody to the subject, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

In some instances, the methods include identifying a subject as a candidate for treatment for an anti-interleukin-4 receptor alpha (IL-4Rα)-related disorder with an anti-IL-4Rα antibody comprising (a) selecting a characteristic or a plurality of characteristics related to an IL 4/IL 13 pathway in a set of data representing medical records of a plurality of subjects; (b) clustering, by a computer system, in accordance with the characteristic or the plurality of characteristics related to the IL-4/IL-13 pathway, a subset of subjects from the plurality of subjects, wherein the subset comprises the characteristic or the plurality of characteristics; (c) identifying in the subset clustered in step (b) the IL-4Rα-related disorder based on symptoms associated with the characteristic or the plurality of characteristics related to the IL-4/IL-13 pathway; and (d) selecting the subject having at least one symptom of, or determined to be susceptible to, an anti-interleukin-4 receptor alpha (IL-4Rα)-related disorder identified in step (c) with the proviso that the IL-4Rα related disorder is not selected from the group consisting of atopic dermatitis, asthma, chronic rhinosinusitis with nasal polyposis, eosinophilic esophagitis, peanut allergy, grass allergy, chronic obstructive pulmonary disease (COPD), prurigo nodularis, bullous pemphigoid, chronic spontaneous urticaria (CSU) and allergic bronchopulmonary aspergillosis (ABPA). In some instances, the method further comprises administering a therapeutically effective amount of the anti-IL-4Rα antibody to the subject, wherein the anti-IL-4Rα antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT).

In some instances, disclosed is a method of treating a subject with an anti-interleukin-4 receptor antibody, comprising: (a) selecting a characteristic or a plurality of characteristics in a set of patients; (b) clustering, by a computer system, in accordance with the characteristic or the plurality of characteristics, a subset of patients having the characteristic or the plurality of characteristics, wherein the characteristic or the plurality of characteristics are associated with at least one symptom of, or determined to be susceptible to, an IL-4R-related disorder; and (c) administering a therapeutically effective amount of an anti-IL-4R antibody to the subject exhibiting at least one symptom of, or determined to be susceptible to, the IL-4R-related disorder, wherein the anti-IL-4R antibody comprises: a variable heavy chain CDR1 of SEQ ID NO:1 (GFTFRDYA); a variable heavy chain CDR2 of SEQ ID NO:2 (ISGSGGNT); a variable heavy chain CDR3 of SEQ ID NO:3 (AKDRLSITIRPRYYGLDV); a variable light chain CDR1 of SEQ ID NO:4 (QSLLYSIGYNY); a variable light chain CDR2 of SEQ ID NO:5 (LGS); and a variable light chain CDR3 of SEQ ID NO:6 (MQALQTPYT). In some instances, the anti-IL-4R antibody is an anti-IL-4R-alpha antibody. In some instances, the anti-IL-4R antibody is dupilumab. In some instances, the IL-4R-related disorder is an IL-4R-alpha-related disorder. In some instances, the IL-4Rα-related disorder is a condition listed in Table 9 or Table 10.

I. Administration

Therapeutic compositions can be administered with suitable carriers, excipients, and other agents that are incorporated into formulations to provide improved transfer, delivery, tolerance, and the like. A multitude of appropriate formulations can be found in the formulary: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311, which is incorporated by reference in its entirety.

II. Dosage

The amount of anti-IL-4Rα antibody (e.g., dupilumab) administered to a subject according to the methods of the present disclosure is, generally, a therapeutically effective amount. A "therapeutically effective amount" or "therapeutically effective dosage" of an IL-4Rα antibody is any amount of the antibody that, when used alone or in combination with another therapeutic agent, promotes disease regression evidenced by a decrease in severity of disease symptoms, an increase in frequency and duration of disease symptom-free periods, or a prevention of impairment or disability due to the disease affliction.

In some instances, the amount of anti-IL-4Rα antibody (e.g., dupilumab) administered to a subject according to the methods of the present disclosure is a prophylactically effective amount. A "prophylactically effective amount" refers to an amount effective, at dosages and for periods of time necessary, to achieve the desired prophylactic result. In some aspects, since a prophylactic dose is used in subjects prior to or at an earlier stage of disease, the prophylactically effective amount is less than the therapeutically effective amount.

The dose can vary depending upon the age and the size of a subject to be administered, target disease, conditions, route of administration, and the like. When anti-IL-4Rα antibody (e.g., dupilumab) is used for treating various conditions and diseases associated with IL-4Rα in an adult patient, it is often advantageous to intravenously administer the antibody at a single dose of about 0.01 to about 20 mg/kg body weight. In some instances, the single dose is about 0.02 to about 7, about 0.03 to about 5, or about 0.05 to about 3 mg/kg body weight. Depending on the severity of the condition, the frequency and the duration of the treatment can be adjusted.

In the case of an anti-IL-4R antibody (e.g., an anti-IL-4Rα antibody, e.g., dupilumab), a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4Rα antibody. In certain embodiments, 300 mg of an anti-IL-4Rα antibody is administered.

The amount of an anti-IL-4R antibody (e.g., an anti-IL-4Rα antibody, e.g., dupilumab) contained within the individual doses can be expressed in terms of milligrams of antibody per kilogram of patient body weight (i.e., mg/kg). For example, the anti-IL-4Rα antibody (e.g., dupilumab) can be administered to a patient at a dose of about 0.0001 to about 10 mg/kg of patient body weight (e.g., about 0.001 mg/kg, about 0.01 mg/kg, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, or about 10.0 mg/kg).

In some instances, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4R antagonist may be administered to a subject at a loading dose of about 200 mg, 400 mg, or about 600 mg followed by one or more maintenance doses of about 75 mg to about 300 mg. In one embodiment, the initial dose and the one or more secondary doses each include 50 mg to 600 mg of the IL-4R antagonist, e.g., 100 mg, 150 mg, 200 mg, 250 mg, 300 mg, 400 mg, 500 mg, or 600 mg of the IL-4R antagonist. In some embodiments, the initial dose and the one or more secondary doses each contain the same amount of the IL-4R antagonist. In other embodiments, the initial dose comprises a first amount of the IL-4R antagonist, and the one or more secondary doses each comprise a second amount of the IL-4R antagonist. For example, the first amount of the IL-4R antagonist can be 1.5×, 2×, 2.5×, 3×, 3.5×, 4× or 5× or more than the second amount of the IL-4R antagonist. In one exemplary embodiment, for a subject having a body weight that is <30 kg (e.g., ≥15 kg to <30 kg), an IL-4R antagonist is administered to a subject at a loading dose of about 200 mg followed by one or more maintenance doses of about 100 mg, or at a loading dose of about 600 mg followed by one or more maintenance doses of about 300 mg. In another exemplary embodiment, for a subject having a body weight that is ≥30 kg (e.g., ≥30 kg to <60 kg), an IL-4R antagonist may be administered to a subject at a loading dose of about 400 mg followed by one or more maintenance doses of about 200 mg, or at a loading dose of about 600 mg followed by one or more maintenance doses of about 300 mg. In yet another exemplary embodiment, for a subject having a body weight that is ≥60 kg, an IL-4R antagonist may be administered to a subject at a loading dose of about 600 mg followed by one or more maintenance doses of about 300 mg.

In some instances, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R antagonist which is administered to a patient prior to the administration of the very next dose in the sequence with no intervening doses.

In some instances, administration is one initial dose of 600 mg (two 300 mg injections in different injection sites), followed by 300 mg given every other week. In some instances, administration is via a pre-filled syringe. In some instances, administration is via a pre-filled pen. In some instances, administration is via an autoinjector. In some aspects, administration is via injection of 300 mg diluted in a 2 mL solution in a single-dose pre-filled syringe with needle shield. In some aspects, administration is one initial dose of 400 mg (two 200 mg injections in different injection sites), followed by 200 mg given every other week. In some aspects, administration is via injection of 200 mg diluted in a 2 mL solution in a single-dose pre-filled syringe with needle shield. In some aspects, administration is via injection of 300 mg diluted in a 2 mL solution in a single-dose pre-filled syringe.

III. Delivery

Various delivery systems are known and can be used to administer a pharmaceutical composition, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of administration include, but are not limited to, intradermal, intramuscular, intraperitoneal, intravenous, subcutaneous, intranasal, epidural, and oral routes. The composition can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local.

IV. Combination Therapies

Also provided are combination therapies in which the anti-IL-4Rα antibody (e.g., dupilumab) or antibody fragment is administered in combination with a second therapeutic agent. Co-administration and combination therapy are not limited to simultaneous administration, but include treatment regimens in which an anti-IL-4Rα antibody or antibody fragment is administered at least once during a course of treatment that involves administering at least one other therapeutic agent to the patient. A second therapeutic agent can be another IL-4 antagonist, such as another antibody/antibody fragment, or a soluble cytokine receptor, an IgE antagonist, an anti-asthma medication (corticosteroids, non-steroidal agents, beta agonists, leukotriene antagonists, xanthines, fluticasone, salmeterol, albuterol), or a checkpoint inhibitor, which can be delivered by inhalation or other appropriate means. In some instances, the anti-IL-4Rα antibody or antibody fragment of the disclosure (e.g., dupilumab) can be administered with an IL-1 antagonist, such as rilonacept, or an IL-13 antagonist. The second agent can include one or more leukotriene receptor antagonists to treat disorders such as allergic inflammatory diseases, e.g., asthma and allergies. Examples of leukotriene receptor antagonists include but are not limited to montelukast, pranlukast, and zafirlukast. The second agent can be a checkpoint inhibitor. In some instances, the checkpoint inhibitor interferes with PD-1, interferes with PD-L1, is an anti-PD-1 antibody or is a PD-1 antagonist (e.g., a human antibody, a humanized antibody, or a chimeric antibody). In some embodiments, the anti-PD-1 antibody is MDX-1106 (also known as nivolumab, MDX-1106-04, ONO-4538, BMS-936558, and Opdivo®), Merck 3475 (pembrolizumab, MK). -3475, Rambrolizumab, Keytruda®, also known as SCH-900475), and CT-011 (also known as Pidilizumab, hBAT, and hBAT-1). In some instances, the checkpoint inhibitor is a CTLA-4 antagonist such as Yervoy® (ipilimumab).

In some instances, the second agent can include a cytokine inhibitor such as one or more of a TNF (etanercept, ENBREL™), IL-9, IL-5 or IL-17 antagonist.

Indications Treatable with Anti-IL-4Rα Antibodies and Fragments Lung-Related Indications Lung Disorders Methods for treating IL-4-induced pulmonary disorders are provided herein. Such disorders include, but are not limited to, lung fibrosis, including chronic fibrotic lung disease, cystic fibrosis, interstitial lung disease, nonspecific interstitial pneumonitis, idiopathic pulmonary fibrosis, hypersensitivity pneumonitis, cryptogenic organizing pneumonia (COP), acute interstitial pneumonitis, desquamative interstitial pneumonitis, chronic obstructive pulmonary disease, pulmonary alveolar proteinosis, adult respiratory distress syndrome (ARDS), asbestosis, sarcoidosis, tuberculosis, and aspirin-exacerbated respiratory disease, other conditions characterized by IL-4-induced fibroblast proliferation or collagen accumulation in the lungs, pulmonary conditions in which a TH2-type immune response plays a role, conditions characterized by decreased barrier function in the lung (e.g., resulting from IL-4-induced damage to the epithelium), or conditions in which IL-4 plays a role in an inflammatory response.

Cystic fibrosis is characterized by the overproduction of mucus and development of chronic infections. Inhibiting IL-4 and the Th2 response reduces mucus production and helps control infections such as allergic bronchopulmonary aspergillosis (ABPA).

Allergic bronchopulmonary mycosis occurs primarily in patients with cystic fibrosis or asthma, where a Th2 immune response is dominant. Inhibiting IL-4 and the Th2 response helps clear and control these infections.

Chronic obstructive pulmonary disease is associated with mucus hypersecretion and fibrosis. Inhibiting IL-4 and the Th2 response reduces the production of mucus and the development of fibrosis thereby improving respiratory function and delaying disease progression.

Bleomycin-induced pneumopathy and fibrosis, and radiation-induced pulmonary fibrosis are disorders characterized by fibrosis of the lung, which is manifested by the influx of Th2, CD4+ cells and macrophages, which produce IL-4 which in turn mediates the development of fibrosis. Inhibiting IL-4 and the Th2 response reduces or prevents the development of these disorders.

Pulmonary alveolar proteinosis is characterized by the disruption of surfactant clearance. IL-4 increases surfactant product. Use of an anti-IL-4R antibody (e.g., an anti-IL-4Rα antibody, e.g., dupilumab) can decrease surfactant production and decrease the need for whole lung lavage.

Adult respiratory distress syndrome (ARDS) can be attributable to a number of factors, one of which is exposure to toxic chemicals. One patient population susceptible to ARDS is critically ill patients who go on ventilators. ARDS is a frequent complication in such patients. An anti-IL-4R antibody (e.g., an anti-IL-4Rα antibody, e.g., dupilumab) can alleviate ARDS by reducing inflammation and adhesion molecules, although methods for treating such patients in accordance with the present disclosure are not limited by a particular mechanism of action. An anti-IL-4R antibody (e.g., an anti-IL-4Rα antibody, e.g., dupilumab) can be used to prevent or treat ARDS.

Sarcoidosis is characterized by granulomatous lesions. An anti-IL-4R antibody (e.g., an anti-IL-4Rα antibody, e.g., dupilumab) can be used to treat sarcoidosis, particularly pulmonary sarcoidosis.

Conditions in which IL-4-induced barrier disruption plays a role (e.g., conditions characterized by decreased epithelial barrier function in the lung) can be treated with an anti-IL-4R antibody (e.g., an anti-IL-4Rα antibody, e.g., dupilumab). Damage to the epithelial barrier in the lungs can be induced by IL-4 directly or indirectly. The epithelium in the lung functions as a selective barrier that prevents contents of the lung lumen from entering the submucosa. A damaged or "leaky" barrier allows antigens to cross the barrier, which in turn elicits an immune response that can cause further damage to lung tissue. Such an immune response can include recruitment of eosinophils or mast cells, for example. An anti-IL-4R antibody (e.g., an anti-IL-4Rα antibody, e.g., dupilumab) can be administered to inhibit such undesirable stimulation of an immune response.

An anti-IL-4R antibody (e.g., an anti-IL-4Rα antibody, e.g., dupilumab) can be administered to promote healing of lung epithelium, thus restoring barrier function. An anti-IL-4R antibody (e.g., an anti-IL-4Rα antibody, e.g., dupilumab) can be administered to promote healing of lung epithelium in asthmatics, for example. Alternatively or in addition to treatment after onset of a disorder, the antibody can be administered for prophylactic purposes, to prevent IL-4-induced damage to lung epithelium.

Disclosed herein are methods of treating a subject having a pulmonary disorder described herein by administering an anti-IL-4R antibody (e.g., an anti-IL-4Rα antibody, e.g., dupilumab). Also disclosed herein are methods of alleviating, ameliorating, or preventing reactions associated with pulmonary disorders described herein by administering an anti-IL-4R antibody (e.g., an anti-IL-4Rα antibody, e.g., dupilumab) to the subject.

Tuberculosis

A TH2-type immune response is implicated in playing a role in causing tissue damage (e.g., necrosis of lung tissue) in tuberculosis (TB) patients. Elevated levels of IL-4 are associated with TB. IL-4 production can be particularly elevated in cavitary tuberculosis (i.e., in TB patients who have developed pulmonary cavities, which can be detected/visualized by such techniques as radiographs of the chest).

An anti-IL-4R antibody (e.g., an anti-IL-4Rα antibody, e.g., dupilumab) can benefit TB patients (especially those with cavitary TB) by suppressing a TH2-type immune response, or by binding (and inactivating) excess secreted IL-4. Methods for treating such patients in accordance with the present disclosure are not limited by a particular mechanism of action, however. Anti-IL-4Rα antibodies (e.g., dupilumab) can advantageously be administered in an amount that restores the desired balance between the TH1 and TH2 components of the immune response, and reduces IL-4-induced tissue damage in a patient.

Disclosed herein are methods of treating a subject having TB by administering an anti-IL-4R antibody (e.g., an anti-IL-4Rα antibody, e.g., dupilumab). Also disclosed herein are methods of alleviating, ameliorating, or preventing reactions associated with TB by administering an anti-IL-4R antibody (e.g., an anti-IL-4Rα antibody, e.g., dupilumab).

Aspirin-Exacerbated Respiratory Disease

Aspirin-exacerbated respiratory disease (AERD), also known as Samter's Triad, is a chronic medical condition that consists of three clinical features: asthma, sinus disease with recurrent nasal polyps, and sensitivity to aspirin and other non-steroidal anti-inflammatory drugs (NSAIDs) that inhibit an enzyme called cyclooxygenase-1. This sensitivity usually manifests as respiratory reactions that occur upon ingesting or inhaling an NSAID, though the exact cause of the reactions is not known. Approximately 9% of all adults with asthma and 30% of patients with asthma and nasal polyps have AERD. In general, AERD develops quite suddenly in adulthood, usually between the ages of 20 and 50, and there is no clearly understood trigger that causes the disease.

Subjects with AERD usually have asthma, nasal congestion and recurrent nasal polyps, and their symptoms often do not respond to conventional treatments. Many have experienced chronic sinus infections and a loss of sense of smell is common.

The characteristic feature of AERD is that patients develop reactions to aspirin and other NSAIDs. These reactions classically involve both upper respiratory symptoms (increased nasal congestion, frontal headache or sinus pain, and sneezing) as well as lower respiratory symptoms (cough, wheezing, chest tightness), but they can also induce skin flushing, rash, abdominal pain and occasionally vomiting.

Disclosed herein are methods of treating a subject having AERD by administering an anti-IL-4R antibody (e.g., an anti-IL-4Rα antibody, e.g., dupilumab) to the subject. Also disclosed herein are methods of alleviating, ameliorating, or preventing reactions associated with AERD by administering an anti-IL-4R antibody (e.g., an anti-IL-4Rα antibody, e.g., dupilumab) to the patient.

Allergic Bronchopulmonary Aspergillosis

Allergic Bronchopulmonary Aspergillosis (ABPA) is an allergic or hypersensitive reaction to a fungus known as *Aspergillus fumigatus*, which is commonly found in soil. In some instances, a subject having ABPA presents with inflammation of the airway. A subject having ABPA often presents with one or more of a cough with brownish flecks or bloody mucous, a fever, wheezing, general coughing, shortness of breath, pleuritic chest pain, and general weakness or malaise. In some instances, a subject having ABPA also has asthma. In some instances, a subject having ABPA also has cystic fibrosis. In some instances, a subject having ABPA also suffers from allergic conditions such as atopic dermatitis (eczema), urticaria (hives), allergic rhinitis (hay fever) and sinusitis.

Disclosed herein are methods of treating a subject having ABPA by administering an anti-IL-4R antibody (e.g., an anti-IL-4Rα antibody, e.g., dupilumab) to the subject. Also disclosed herein are methods of alleviating, ameliorating, or preventing reactions associated with ABPA by administering an anti-IL-4R antibody (e.g., an anti-IL-4Rα antibody, e.g., dupilumab) to the patient.

Extrinsic Allergic Alveolitis

Extrinsic allergic alveolitis (or hypersensitivity pneumonitis) is a lung disorder resulting from repeated inhalation of organic dust, usually in a specific occupational setting. In the acute form, respiratory symptoms and fever begin several hours after exposure to the dust. Symptoms of extrinsic allergic alveolitis include breathing difficulty, wheezing, and dry coughs that appear to shake the entire body. In some instances, a subject having extrinsic allergic alveolitis presents with chills, sweating, aching, discomfort and/or fatigue may accompany lung symptoms. In some aspects, extrinsic allergic alveolitis is acute. In some instances, extrinsic allergic alveolitis is chronic. In the case of chronic extrinsic allergic alveolitis, in some instances, a subject can have symptoms of fever, crackling sounds during breathing (rales), breathing difficulty, bluish appearance of the skin (cyanosis), and expectoration of blood.

Disclosed herein are methods of treating a subject having extrinsic allergic alveolitis by administering an anti-IL-4R antibody (e.g., an anti-IL-4Rα antibody, e.g., dupilumab) to the subject. Also disclosed herein are methods of alleviating, ameliorating, or preventing reactions associated with extrinsic allergic alveolitis by administering an anti-IL-4R antibody (e.g., an anti-IL-4Rα antibody, e.g., dupilumab) to the patient.

Upper Respiratory Tract Hyper-Sensitivity Reaction, Site Unspecified and Other Respiratory Conditions Due to Environmental Exposure Upper respiratory tract hyper-sensitivity reaction, site unspecified or not otherwise specified (NOS) (also known as upper respiratory allergies; hypersensitivity NOS; hypersensitivity reaction; allergy NOS; and the like) includes respiratory tract and food hypersensitivity. In some instances, Upper respiratory tract hyper-sensitivity reaction includes symptoms of nasal congestion, rhinorrhea, sneezing, itching of the nose and throat, coughing, or wheezing. In some instances, upper respiratory tract hyper-sensitivity reaction, site unspecified results from an inhalant allergy. In some instances, upper respiratory tract hyper-sensitivity reaction, site unspecified results from a food allergy. In some instances, a subject as disclosed herein has an upper respiratory tract hyper-sensitivity reaction, site unspecified or not otherwise specified (NOS).

In some instances, a subject disclosed herein is a subject who experiences respiratory sensitivity upon exposure to environmental conditions. For example, in some instances, a subject is exposed to one or more chemicals, one or more gases, one or more fumes, one or more vapors; or a combination thereof.

Disclosed herein are methods of treating a subject having upper respiratory tract hyper-sensitivity reaction, site unspecified or not otherwise specified (NOS) by administering an anti-IL-4R antibody (e.g., an anti-IL-4Rα antibody, e.g., dupilumab) to the subject. Also disclosed herein are methods of alleviating, ameliorating, or preventing reactions associated with upper respiratory tract hyper-sensitivity reaction, site unspecified or not otherwise specified (NOS) by administering an anti-IL-4R antibody (e.g., an anti-IL-4Rα antibody, e.g., dupilumab) to the patient.

Also disclosed herein are methods of treating a subject exposed one or more chemicals, one or more gases, one or more fumes, one or more vapors; or a combination thereof, by administering an anti-IL-4R antibody (e.g., an anti-IL-4Rα antibody, e.g., dupilumab) to the subject. Also disclosed herein are methods of alleviating, ameliorating, or preventing reactions associated with exposure to one or more chemicals, one or more gases, one or more fumes, one or more vapors, or a combination thereof, by administering an anti-IL-4R antibody (e.g., an anti-IL-4Rα antibody, e.g., dupilumab) to the patient.

Pharyngitis

Pharyngitis (e.g., a sore throat) is caused by swelling in the back of the pharynx between the tonsils and larynx. In some instances, pharyngitis is caused by one or more viruses. For example, in some instances, a virus that causes pharyngitis can include one or more influenza viruses, an enterovirus such as a coxsackie virus (e.g., in the setting of hand, foot, and mouth disease), or an Epstein-Barr virus (EBV) (e.g., in the setting of mononucleosis). In some instances, pharyngitis is caused by bacteria. For example, in some instances, a subject having pharyngitis is infected by a species of *Neisseria* (e.g., *gonorrhoeae*); a species of *Chlamydia* (e.g., *trachomatis*) or a species of *Streptococcus* (e.g., a group A *Streptococcus*; e.g., pharyngitis).

Disclosed herein are methods of treating a subject having pharyngitis by administering an anti-IL-4R antibody (e.g., an anti-IL-4Rα antibody, e.g., dupilumab) to the subject. Also disclosed herein are methods of alleviating, ameliorating, or preventing reactions associated with pharyngitis by administering an anti-IL-4R antibody (e.g., an anti-IL-4Rα antibody, e.g., dupilumab) to the patient.

Nasopharyngitis and Chronic Nasopharyngitis

In some instances, a subject as disclosed herein has a clinical diagnosis of pharyngitis, and in particular nasopharyngitis (also called the common cold). In some instances, nasopharyngitis is acute (e.g., common cold). In some instances, nasopharyngitis is not acute. Symptoms associated with nasopharyngitis include one or more of a runny or stuffy nose; sneezing; coughing; sore or scratchy throat; watery or itchy eyes; headache; tiredness; and body aches. In some instances, nasopharyngitis is viral. In some instances, nasopharyngitis is bacterial. In some instances, nasopharyngitis is chronic. In some instances, nasopharyngitis becomes chronic when one or more symptoms of nasopharyngitis lasts for at least 4 weeks, at least 5 weeks, at least 6 weeks, at least 7 weeks at least 8 weeks, or longer.

Disclosed herein are methods of treating a subject having nasopharyngitis by administering an anti-IL-4R antibody (e.g., an anti-IL-4Rα antibody, e.g., dupilumab) to the subject. Also disclosed herein are methods of alleviating, ameliorating, or preventing reactions associated with nasopharyngitis by administering an anti-IL-4R antibody (e.g., an anti-IL-4Rα antibody, e.g., dupilumab) to the patient.

Also disclosed herein are methods of treating a subject having chronic nasopharyngitis by administering an anti-IL-4R antibody (e.g., an anti-IL-4Rα antibody, e.g., dupilumab) to the subject. Also disclosed herein are methods of alleviating, ameliorating, or preventing reactions associated with chronic nasopharyngitis by administering an anti-IL-4R antibody (e.g., an anti-IL-4Rα antibody, e.g., dupilumab) to the patient.

Bronchitis, Including Simple Chronic Bronchitis and Mucopurulent Chronic Bronchitis Bronchitis is an inflammation of the bronchial tubes. In some instances, a subject disclosed herein has bronchitis. In some instances, bronchitis is acute. In some instances, bronchitis is chronic. Compared to a normal subject, a subject having chronic bronchitis presents with increased mucus, increased coughing and increased difficulty when breathing. A subject having chronic bronchitis (e.g., simple chronic bronchitis) presents with symptoms of bronchitis for at least 1 month, at least 2 months, at least 3 months, at least 4 months, at least 5 months, at least 6 months, or more.

In some instances, a subject having mucopurulent chronic bronchitis can also present with bronchiectasis, which is a chronic condition where the walls of the bronchi are thickened from inflammation and infection. In some instances, a subject having mucopurulent chronic bronchitis can also present with persistent or recurrent purulent sputum production.

Disclosed herein are methods of treating a subject having simple chronic bronchitis by administering an anti-IL-4R antibody (e.g., an anti-IL-4Rα antibody, e.g., dupilumab) to the subject. Also disclosed herein are methods of alleviating, ameliorating, or preventing reactions associated with simple chronic bronchitis by administering an anti-IL-4R antibody (e.g., an anti-IL-4Rα antibody, e.g., dupilumab) to the patient.

Disclosed herein are methods of treating a subject having mucopurulent chronic bronchitis by administering an anti-IL-4R antibody (e.g., an anti-IL-4Rα antibody, e.g., dupilumab) to the subject. Also disclosed herein are methods of alleviating, ameliorating, or preventing reactions associated with mucopurulent chronic bronchitis by administering an anti-IL-4R antibody (e.g., an anti-IL-4Rα antibody, e.g., dupilumab) to the patient.

Ear-, Nose- and Throat-Related Indications

In some instances, disclosed are methods of treating ear-, nose- and throat-related indications, including chronic diseases of tonsils and adenoids, hypertrophy of adenoids, otosclerosis, mastoiditis and related conditions, or otitis externa.

Chronic Diseases of Tonsils and Adenoids

Disclosed herein are subjects having one or more chronic diseases of the tonsils. Disclosed herein are subjects having one or more chronic diseases of the adenoids.

The tonsils are the two masses of tissue on either side of the back of the throat. Small depressions are often found on the surface of the tonsils, called crypts. These crypts may appear deep and contain stones called tonsilliths. The adenoids are located high in the throat behind the nose and soft palate (the roof of the mouth). Unlike tonsils, the adenoids are not easily visible through the mouth.

In some instances, chronic diseases of the tonsils include tonsillitis, which is an infection of the tonsils. Symptoms of tonsillitis include one or more of swelling of the tonsils; a white or yellow coating on the tonsils; a slight change in the voice due to swelling; sore throat sometimes accompanied by ear pain; uncomfortable or painful swallowing; swollen lymph nodes in the neck; fever; or bad breath.

In some instances, chronic diseases of the adenoids include hypertrophy or inflammation of the adenoids. Symptoms include nasal obstruction, sleep disturbances, and middle ear effusions with hearing loss.

Disclosed herein are methods of treating a subject having one or more chronic diseases of tonsils and adenoids by administering an anti-IL-4R antibody (e.g., an anti-IL-4Rα antibody, e.g., dupilumab) to the subject. Also disclosed herein are methods of alleviating, ameliorating, or preventing reactions associated with one or more chronic diseases of tonsils and adenoids by administering an anti-IL-4R antibody (e.g., an anti-IL-4Rα antibody, e.g., dupilumab) to the patient.

Disclosed herein are methods of treating a subject having one or more chronic diseases of the tonsils by administering an anti-IL-4R antibody (e.g., an anti-IL-4Rα antibody, e.g., dupilumab) to the subject. Also disclosed herein are methods of alleviating, ameliorating, or preventing reactions associated with one or more chronic diseases of the tonsils by administering an anti-IL-4R antibody (e.g., an anti-IL-4Rα antibody, e.g., dupilumab) to the patient.

Disclosed herein are methods of treating a subject having one or more chronic diseases of the adenoids by administering an anti-IL-4R antibody (e.g., an anti-IL-4Rα antibody, e.g., dupilumab) to the subject. Also disclosed herein are methods of alleviating, ameliorating, or preventing reactions associated with one or more chronic diseases of the adenoids by administering an anti-IL-4R antibody (e.g., an anti-IL-4Rα antibody, e.g., dupilumab) to the patient.

Adenoid Hypertrophy

Hypertrophy of adenoids is the unusual growth of the adenoid. In some instances, most subjects are children. In some instances, the adenoid continues to become larger and block the passage behind the nose. In some instances, this can result in snoring, breathing through the mouth, and/or a hyponasal sound to the speech. In some instances, adenoid hypertrophy results in otitis media because of blockage of the eustachian tube.

Disclosed herein are methods of treating a subject having hypertrophy of adenoids by administering an anti-IL-4R antibody (e.g., an anti-IL-4Rα antibody, e.g., dupilumab) to the subject. Also disclosed herein are methods of alleviating, ameliorating, or preventing reactions associated with hypertrophy of adenoids by administering an anti-IL-4R antibody (e.g., an anti-IL-4Rα antibody, e.g., dupilumab) to the patient.

Otosclerosis

Otosclerosis is the abnormal growth of bone of the middle ear. This bone prevents structures within the ear from working properly and causes hearing loss. For some people with otosclerosis, the hearing loss may become severe. The condition is caused by abnormal bone remodeling in the middle ear. Bone remodeling is a lifelong process in which bone tissue renews itself by replacing old tissue with new. In otosclerosis, abnormal remodeling disrupts the ability of sound to travel from the middle ear to the inner ear. Otosclerosis is most often caused when one of the bones in the middle ear, the stapes, becomes stuck in place. When this bone is unable to vibrate, sound is unable to travel through the ear and hearing becomes impaired.

Disclosed herein are methods of treating a subject having otosclerosis by administering an anti-IL-4R antibody (e.g., an anti-IL-4Rα antibody, e.g., dupilumab) to the subject. Also disclosed herein are methods of alleviating, ameliorating, or preventing reactions associated with otosclerosis by administering an anti-IL-4R antibody (e.g., an anti-IL-4Rα antibody, e.g., dupilumab) to the patient.

Mastoiditis

Mastoiditis is a bacterial infection in the mastoid process. Mastoiditis usually occurs when untreated or inadequately treated acute otitis media spreads from the middle ear into the mastoid process. In some instances, mastoiditis is acute. In some instances, mastoiditis is chronic. Symptoms of mastoiditis include swelling behind the ear, pus coming out of the ear, throbbing pain, and difficulty hearing. In some instances, swelling behind the ear can be intermittent.

Disclosed herein are methods of treating a subject having mastoiditis by administering an anti-IL-4R antibody (e.g., an anti-IL-4Rα antibody, e.g., dupilumab) to the subject. Also disclosed herein are methods of alleviating, ameliorating, or preventing reactions associated with mastoiditis by administering an anti-IL-4R antibody (e.g., an anti-IL-4Rα antibody, e.g., dupilumab) to the patient.

Otitis Externa

Otitis externa is a condition that causes inflammation of the external ear canal, which is the tube between the outer ear and eardrum. In some instances, otitis externa is acute. In some instances, otitis externa is caused by an infection by a bacteria (e.g., *Pseudomonas*). Symptoms include pain, discharge, and hearing loss if the ear canal has swollen shut; manipulation of the auricle causes pain.

Disclosed herein are methods of treating a subject having otitis externa by administering an anti-IL-4R antibody (e.g., an anti-IL-4Rα antibody, e.g., dupilumab) to the subject. Also disclosed herein are methods of alleviating, ameliorating, or preventing reactions associated with otitis externa by administering an anti-IL-4R antibody (e.g., an anti-IL-4Rα antibody, e.g., dupilumab) to the patient.

Hematology-, Rheumatologic-, and Immuno-Related Indications

In some instances, disclosed are methods of treating blood-related indications, including sickle cell disease, Churg-Strauss syndrome, autoimmune lymphoproliferative syndrome, lupus (systemic lupus erythematosus), antiphospholipid antibody syndrome (APS), or autoimmune hemolytic anemia.

Sickle Cell Disease

Sickle cell disease patients typically experience intermittent periods of acute exacerbation called crises, with the crises being categorized as anemic or vaso-occlusive. Anti-IL-4Rα antibodies (e.g., dupilumab) find use in treating or preventing sickle cell crisis, especially in patients with elevated IL-4 levels or in whom the immune response has shifted toward a TH2-type response. Sickle cell disease (especially sickle cell crisis) has been associated with increased susceptibility to infectious diseases, including bacterial infections. Administering anti-IL-4Rα antibodies (e.g., dupilumab) to sickle cell disease patients can help the patient mount an immune response against infectious diseases.

Disclosed herein are methods of treating a subject having sickle cell disease by administering an anti-IL-4R antibody (e.g., an anti-IL-4Rα antibody, e.g., dupilumab). Also disclosed herein are methods of alleviating, ameliorating, or preventing reactions associated with sickle cell disease by administering an anti-IL-4R antibody (e.g., an anti-IL-4Rα antibody, e.g., dupilumab).

Churg-Strauss Syndrome

Churg-Strauss syndrome, a disease also known as allergic granulomatous angiitis or eosinophilic granulomatosis with polyangiitis, is characterized by inflammation of the blood vessels in persons with a history of asthma or allergy, and by eosinophilia. Anti-IL-4Rα antibodies (e.g., dupilumab) can be administered to alleviate inflammation in patients with this syndrome. The use of anti-IL-4Rα antibodies to suppress a TH2-type immune response, and to combat eosinophilia, would benefit the patients.

Disclosed herein are methods of treating a subject having Churg-Strauss syndrome by administering an anti-IL-4R antibody (e.g., an anti-IL-4Rα antibody, e.g., dupilumab). Also disclosed herein are methods of alleviating, ameliorating, or preventing reactions associated with Churg-Strauss syndrome by administering an anti-IL-4R antibody (e.g., an anti-IL-4Rα antibody, e.g., dupilumab).

Autoimmune Lymphoproliferative Syndrome

Manifestations of autoimmune lymphoproliferative syndrome include lymphoproliferation and autoantibody production. Patients with the syndrome reportedly have an inherited deficiency in apoptosis. An anti-IL-4R antibody (e.g., an anti-IL-4Rα antibody, e.g., dupilumab) can benefit patients with this syndrome by suppressing a TH2-type immune response, or by binding (and inactivating) excess IL-4 at sites of inflammation. Methods for treating such patients in accordance with the present disclosure are not limited by a particular mechanism of action, however.

Disclosed herein are methods of treating a subject having autoimmune lymphoproliferative syndrome by administering an anti-IL-4R antibody (e.g., an anti-IL-4Rα antibody, e.g., dupilumab). Also disclosed herein are methods of alleviating, ameliorating, or preventing reactions associated with autoimmune lymphoproliferative syndrome by administering an anti-IL-4R antibody (e.g., an anti-IL-4Rα antibody, e.g., dupilumab) to a subject.

Lupus (Systemic Lupus Erythematosus),

Systemic Lupus Erythematosus (or "lupus") is an autoimmune disease, characterized by the production of unusual autoantibodies in the blood. These autoantibodies bind to their respective antigens, forming immune complexes which circulate and eventually deposit in tissues. This immune complex deposition causes chronic inflammation and tissue damage.

Disclosed herein are methods of treating a subject having autoimmune lupus (systemic lupus erythematosus) by administering an anti-IL-4R antibody (e.g., an anti-IL-4Rα antibody, e.g., dupilumab). Also disclosed herein are methods of alleviating, ameliorating, or preventing reactions associated with lupus (systemic lupus erythematosus) by administering an anti-IL-4R antibody (e.g., an anti-IL-4Rα antibody, e.g., dupilumab) to a subject.

Antiphospholipid Antibody Syndrome (APS)

Antiphospholipid Antibody Syndrome (APS) is an autoimmune disease present mostly in young women. Those with APS make abnormal proteins called antiphospholipid autoantibodies in the blood. This causes blood to flow improperly and can lead to dangerous clotting in arteries and veins, problems for a developing fetus and pregnancy miscarriage. People with this disorder may otherwise be healthy, or they also may suffer from an underlying disease, most frequently lupus.

Disclosed herein are methods of treating a subject having antiphospholipid antibody syndrome (APS) by administering an anti-IL-4R antibody (e.g., an anti-IL-4Rα antibody, e.g., dupilumab). Also disclosed herein are methods of alleviating, ameliorating, or preventing reactions associated with APS by administering an anti-IL-4R antibody (e.g., an anti-IL-4Rα antibody, e.g., dupilumab) to a subject.

Autoimmune Hemolytic Anemia

Excessive IL-4 secretion, and a deficiency in TH1-type cytokines, are implicated in contributing to the pathogenesis of autoimmune hemolytic anemia. Anti-IL-4Rα antibody (e.g., dupilumab) can be administered to reduce autoantibody production, and to restore a more normal balance between the TH1 and TH2 components of the immune response.

Disclosed herein are methods of treating a subject having autoimmune hemolytic anemia which include administering an anti-IL-4R antibody (e.g., an anti-IL-4Rα antibody, e.g., dupilumab). Also disclosed are methods of alleviating, ameliorating, or preventing reactions associated with autoimmune hemolytic anemia, which include administering an anti-IL-4R antibody (e.g., an anti-IL-4Rα antibody, e.g., dupilumab).

Eosinophilia

Eosinophilia is a disease or disorder characterized by excess of eosinophils. In some instances, eosinophilia occurs in blood. In some instances, eosinophilia occurs in one or more tissues. In some instances, absolute eosinophil counts in peripheral blood exceeding 450 to 550 cells/µL are considered elevated. In some instances, percentages generally above 5% of the differential are regarded as elevated eosinophils. In some instances, eosinophilia occurs because of an allergic reaction. In some instances, eosinophilia occurs because of a parasitic infection. In some instances, eosinophilia is mild. In some instances, eosinophilia is moderate. In some instances, eosinophilia is severe. In some instances, organ damage occurs. Organ damage typically occurs because of tissue inflammation and reaction to the cytokines and chemokines released by the eosinophils as well as to immune cells that are recruited to the tissues. Although any organ may be involved, in some instances, the heart, lungs, spleen, skin, and nervous system are typically affected.

Disclosed herein are methods of treating a subject having eosinophilia which include administering an anti-IL-4R antibody (e.g., an anti-IL-4Rα antibody, e.g., dupilumab). Also disclosed are methods of alleviating, ameliorating, or preventing reactions associated with eosinophilia, which include administering an anti-IL-4R antibody (e.g., an anti-IL-4Rα antibody, e.g., dupilumab).

Systemic Mastocytosis

Systemic mastocytosis is a disorder where mast cells are abnormally increased in multiple organs including the bone marrow. Mast cells are immune cells that produce a variety of mediators, such as histamine, that are important in the body's allergic responses. Symptoms of systemic mastocytosis include facial flushing, itching, anemia and bleeding disorders; gastrointestinal symptoms such as abdominal pain, diarrhea, nausea, and/or vomiting; anaphylactoid reactions; and enlarged liver (hepatomegaly), spleen (splenomegaly), and lymph nodes (lymphadenopathy). Other symptoms include feeling lightheaded or losing consciousness. Common triggers include alcohol, temperature changes, spicy foods, and certain medications. In some instances, subjects with systemic mastocytosis have somatic mutations in the KIT gene.

Disclosed herein are methods of treating a subject having systemic mastocytosis by administering an anti-IL-4R antibody (e.g., an anti-IL-4Rα antibody, e.g., dupilumab) to the subject. Also disclosed herein are methods of alleviating, ameliorating, or preventing reactions associated with systemic mastocytosis by administering an anti-IL-4R antibody (e.g., an anti-IL-4Rα antibody, e.g., dupilumab) to the patient.

Graft-Versus-Host Disease

Graft versus host disease (GvHD) is a condition that might occur after an allogeneic transplant. In GvHD, the donated bone marrow or peripheral blood stem cells view the recipient's body as foreign, and the donated cells/bone marrow attack the body. In some instances, GvHD is acute graft versus host disease (aGvHD). In some instances, GvHD is chronic graft versus host disease (cGvHD). Several factors are thought to increase the development of acute GvHD (aGvHD), including donor/recipient HLA (human leukocyte antigen) mismatch. A subject having aGvHD may present with one or more of skin rash or reddened areas on the skin; yellow discoloration of the skin and/or eyes; and abnormal liver function tests; nausea, vomiting, diarrhea, or abdominal cramping; and increased dryness/irritation of the eyes.

A subject having aGvHD may present with one or more of rash, raised, or discolored areas, skin thickening or tightening; abdominal swelling, yellow discoloration of the skin and/or eyes, and abnormal blood test results; dry eyes or vision changes; dry mouth, white patches inside the mouth, pain or sensitivity to spicy foods; shortness of breath or changes seen on your chest X-ray; difficulty swallowing, pain with swallowing, or weight loss; and fatigue, muscle weakness, or pain.

Disclosed herein are methods of treating a subject having GvHD by administering an anti-IL-4R antibody (e.g., an anti-IL-4Rα antibody, e.g., dupilumab) to the subject. Also disclosed herein are methods of alleviating, ameliorating, or preventing reactions associated with GvHD by administering an anti-IL-4R antibody (e.g., an anti-IL-4Rα antibody, e.g., dupilumab) to the patient.

Myositis

Myositis is a general name for inflammation of the muscles. Myositis includes dermatomyositis; inclusion body myositis; juvenile myositis; and polymyositis. In some instances, myositis include chronic, progressive inflammation of the muscles. Symptoms of myositis may include one or more of trouble standing up; difficulty climbing stairs or lifting arms; tired feeling after standing or walking; trouble swallowing or breathing; or muscle pain and soreness that does not resolve after a few weeks.

Disclosed herein are methods of treating a subject having myositis by administering an anti-IL-4R antibody (e.g., an anti-IL-4Rα antibody, e.g., dupilumab) to the subject. Also disclosed herein are methods of alleviating, ameliorating, or preventing reactions associated with myositis by administering an anti-IL-4R antibody (e.g., an anti-IL-4Rα antibody, e.g., dupilumab) to the patient.

Felty's Syndrome

Felty's syndrome (or Felty syndrome) is rare autoimmune disease characterized by the rheumatoid arthritis, enlargement of the spleen, and decreased neutrophils (i.e., neutropenia). Additional symptoms of Felty's syndrome include one or more of fatigue, fever, weight loss, discoloration of patches of skin, mild hepatomegaly (enlarged liver), lymphadenopathy (swelling of lymph nodes), Sjögren syndrome, vasculitis, and lower-extremity ulcers. The exact cause is unknown, but several risk factors have been proposed, including autoimmunity.

Disclosed herein are methods of treating a subject having Felty's syndrome by administering an anti-IL-4R antibody (e.g., an anti-IL-4Rα antibody, e.g., dupilumab) to the subject. Also disclosed herein are methods of alleviating, ameliorating, or preventing reactions associated with Felty's syndrome by administering an anti-IL-4R antibody (e.g., an anti-IL-4Rα antibody, e.g., dupilumab) to the patient.

Adult-Onset Still's Disease

Adult-onset Still's disease (AOSD) is a form of Still's disease, a rare systemic auto-inflammatory disease characterized by symptoms including one or more of fevers, joint pain, sore throat, muscle pain, and a distinctive salmon-colored bumpy rash. In some instances, subject have just one episode of adult Still's disease. In some instances, the condition persists or recurs. Inflammation caused by AOSD can destroy affected joints, particularly the wrists.

Disclosed herein are methods of treating a subject having AOSD by administering an anti-IL-4R antibody (e.g., an anti-IL-4Rα antibody, e.g., dupilumab) to the subject. Also disclosed herein are methods of alleviating, ameliorating, or preventing reactions associated with AOSD by administering an anti-IL-4R antibody (e.g., an anti-IL-4Rα antibody, e.g., dupilumab) to the patient.

Juvenile Rheumatoid Arthritis

Juvenile rheumatoid arthritis (JRA; also called juvenile idiopathic arthritis; JIA) is a form of arthritis in children. Subjects having JRA present with arthritis, inflammation, and joint stiffness. In some instances, the subject having JRA is between 6 weeks of age and 16 years old. In some instances, JRA affects bone development in a growing child. In some instances, a subject has systemic onset JRA, which affects one or more joints; often presents with a high fever and a skin rash; often leads to inflammation of internal organs, including the heart, liver, spleen, and lymph nodes. In some instances, a subject has oligoarticular JRA, which affects 1 to 4 joints in the first 6 months of disease. In some instances, a subject has polyarticular JRA, which affects 5 or more joints in the first 6 months of disease. In some instances, a subject has enthesitis-related JRA, which presents with arthritis and enthesitis. In some instances, a subject has psoriatic arthritis, which present with arthritis and psoriasis.

Disclosed herein are methods of treating a subject having juvenile rheumatoid arthritis by administering an anti-IL-4R antibody (e.g., an anti-IL-4Rα antibody, e.g., dupilumab) to the subject. Also disclosed herein are methods of alleviating, ameliorating, or preventing reactions associated with juvenile rheumatoid arthritis by administering an anti-IL-4R antibody (e.g., an anti-IL-4Rα antibody, e.g., dupilumab) to the patient.

Hyper-IgE (Hyperimmunoglobulinemia E) Syndromes

Hyper-IgE (hyperimmunoglobulinemia E) Syndromes are a group of a hereditary immunodeficiency disorders characterized by recurring boils, sinus and lung infections, and a severe rash that appear during infancy. Hyper-IgE (hyperimmunoglobulinemia E) Syndromes are very rare immunodeficiency syndromes with multisystem involvement, including immune system, skeleton, connective tissue, and dentition. Hyper-IgE (hyperimmunoglobulinemia E) Syndromes are characterized by the classic triad of high serum levels of immunoglobulin E (IgE), recurrent staphylococcal cold skin abscess, and recurrent pneumonia with pneumatocele formation. Most cases of Hyper-IgE (hyperimmunoglobulinemia E) Syndromes are sporadic although can be inherited as autosomal dominant and autosomal recessive traits. A fundamental immunologic defect in Hyper-IgE (hyperimmunoglobulinemia E) Syndromes is not clearly elucidated but abnormal neutrophil chemotaxis due to decreased production or secretion of interferon γ has a main role in the immunopathogenesis of syndrome, also distorted Th1/Th2 cytokine profile toward a Th2 bias contributes to the impaired cellular immunity and a specific pattern of infection susceptibility as well as atopic-allergic constitution of syndrome.

Disclosed herein are methods of treating a subject having Hyper-IgE (hyperimmunoglobulinemia E) Syndromes by administering an anti-IL-4R antibody (e.g., an anti-IL-4Rα antibody, e.g., dupilumab) to the subject. Also disclosed herein are methods of alleviating, ameliorating, or preventing reactions associated with Hyper-IgE (hyperimmunoglobulinemia E) Syndromes by administering an anti-IL-4R antibody (e.g., an anti-IL-4Rα antibody, e.g., dupilumab) to the patient.

Severe Combined Immunodeficiency (SCID)

Severe combined immunodeficiency (SCID) is a group of rare disorders caused by mutations in different genes involved in the development and function of infection-fighting immune cells. Infants with SCID appear healthy at birth but are highly susceptible to severe infections. The condition is fatal, usually within the first year or two of life, unless infants receive immune-restoring treatments, such as transplants of blood-forming stem cells, gene therapy, or enzyme therapy. More than 80 percent of SCID infants do not have a family history of the condition. However, development of a newborn screening test has made it possible to detect SCID before symptoms appear, helping ensure that affected infants receive life-saving treatments. Subjects with SCID have trouble producing white cells and are less able to stave off infections, making them susceptible to infections by bacteria, viruses, and fungi. In some instances, SCID is X-linked. In some instances, SCID is ADA-deficient SCID.

Disclosed herein are methods of treating a subject having SCID by administering an anti-IL-4R antibody (e.g., an anti-IL-4Rα antibody, e.g., dupilumab) to the subject. Also disclosed herein are methods of alleviating, ameliorating, or preventing reactions associated with SCID by administering an anti-IL-4R antibody (e.g., an anti-IL-4Rα antibody, e.g., dupilumab) to the patient.

Eye-Related Indications

In some instances, disclosed are methods of treating eye-related indications, including dry eye, blepharitis, blepharoconjunctivitis, cicatricial pemphigoid, Mooren's corneal ulcer, Vogt-Koyanagi-Harada syndrome, sympathetic opthalmia, phacoanaphylaxis endophthalmitis, keratoconjunctivitis sicca (KCS), or atopic keratoconjunctivitis (AKC).

Sjogren's Syndrome

The autoimmune disease known as Sjogren's syndrome or sicca syndrome typically combines dry eyes and dry mouth with a disorder of the connective tissues, such as rheumatoid arthritis, lupus, scleroderma, or polymyositis. The vast majority of patients are middle age (or older) females. Sjogren's syndrome is an inflammatory disease of glands (e.g., lacrimal and salivary glands) and other tissues of the body. The syndrome typically is associated with autoantibody production.

Anti-IL-4Rα antibodies (e.g., dupilumab) can be administered to reduce the inflammatory response (such as inflammation of glands, including lacrimal glands) in such patients. Anti-IL-4Rα antibodies (e.g., dupilumab) can benefit Sjogren's syndrome patients by suppressing a TH2-type immune response, or by binding (and inactivating) excess IL-4 at inflammatory lesions. Methods for treating patients in accordance with the present disclosure are not limited by a particular mechanism of action, however.

Disclosed herein are methods of treating a subject having Sjogren's syndrome by administering an anti-IL-4R antibody (e.g., an anti-IL-4Rα antibody, e.g., dupilumab). Also disclosed herein are methods of alleviating, ameliorating, or preventing reactions associated with Sjogren's syndrome by administering an anti-IL-4R antibody (e.g., an anti-IL-4Rα antibody, e.g., dupilumab).

Autoimmune Uveitis

Autoimmune uveitis, or uveitis, involves inflammation of the uvea (generally considered to include the iris, ciliary body, and choroid, considered together). Excess IL-4 secretion is implicated as playing a role in pathogenesis of this sight-threatening inflammatory eye disease. In accordance with the present disclosure, an anti-IL-4R antibody (e.g., an anti-IL-4Rα antibody, e.g., dupilumab) is administered to a uveitis patient to reduce disease severity. In one embodiment, an anti-IL-4R antibody (e.g., an anti-IL-4Rα antibody, e.g., dupilumab) is administered to an individual who has autoimmune uveoretinitis.

Disclosed herein are methods of treating a subject having autoimmune uveitis by administering an anti-IL-4R antibody (e.g., an anti-IL-4Rα antibody, e.g., dupilumab). Also disclosed herein are methods of alleviating, ameliorating, or preventing reactions associated with autoimmune uveitis by administering an anti-IL-4R antibody (e.g., an anti-IL-4Rα antibody, e.g., dupilumab).

Giant Papillary Conjunctivitis

Giant papillary conjunctivitis (GPC) is an allergic reaction of the eye that occurs when one or several small round bumps (papillae) develop on the underside of the eyelid. In some instances, GPC is chronic GPC. Symptoms of GPC include bumps that begin to form on the underside of an upper eyelid; itching; feeling like there's a foreign object in an eye; eye redness; forming excess mucus; swelling; and blurry vision. In some instances, GPC is chronic.

Disclosed herein are methods of treating a subject having GPC by administering an anti-IL-4R antibody (e.g., an anti-IL-4Rα antibody, e.g., dupilumab). Also disclosed herein are methods of alleviating, ameliorating, or preventing reactions associated with GPC by administering an anti-IL-4R antibody (e.g., an anti-IL-4Rα antibody, e.g., dupilumab).

Disclosed herein are methods of treating a subject having chronic GPC by administering an anti-IL-4R antibody (e.g., an anti-IL-4Rα antibody, e.g., dupilumab). Also disclosed herein are methods of alleviating, ameliorating, or preventing reactions associated with chronic GPC by administering an anti-IL-4R antibody (e.g., an anti-IL-4Rα antibody, e.g., dupilumab).

Primary GPC includes atopic keratoconjunctivitis (AKC) and vernal keratoconjunctivitis (VKC). Secondary GPC is caused by an irritation in the eye (e.g., by a contact lens or a suture).

Atopic Keratoconjunctivitis

Atopic keratoconjunctivitis (AKC; also called atopic conjunctivitis) is the result of a condition called "atopy." Atopy is a genetic condition where the immune system produces higher than normal antibodies in response to a given allergen. Although AKC is a perennial (year round) disease, symptoms can worsen in the winter. Unlike atopic dermatitis, which is generally seen early in childhood, atopic keratoconjunctivitis appears during late adolescence and early adulthood. Men are more commonly affected than women.

With AKC, the conjunctiva lining the eyelids is usually red and swollen. The lower eyelid generally is affected more than the upper eyelid. This is a differentiating symptom from vernal keratoconjunctivitis where the upper eyelid is most often affected. If left untreated, AKC can progress to ulceration, scarring, cataract, keratoconus, and corneal vascularization. Symptoms of AKC include sensitivity to light, itching, burning, tearing, and red and hardened eyelids.

Disclosed herein are methods of treating a subject having AKC which include administering an anti-IL-4R antibody (e.g., an anti-IL-4Rα antibody, e.g., dupilumab). Also disclosed are methods of alleviating, ameliorating, or preventing reactions associated with AKC, which include administering an anti-IL-4R antibody (e.g., an anti-IL-4Rα antibody, e.g., dupilumab) to a subject.

Vernal Conjunctivitis

Vernal conjunctivitis is inflammation of the outer lining of the eyes. In some instances, vernal conjunctivitis is chronic. In some instances, vernal conjunctivitis presents because of an allergic reaction. In some instances, vernal conjunctivitis presents with asthma. In some instances, the manifestation of vernal conjunctivitis is seasonal. Vernal conjunctivitis presents with upregulation of an IgE-mediated pathway. Subjects having vernal conjunctivitis present with symptoms of intense itching, lacrimation, mucous secretions, and severe photophobia.

Disclosed herein are methods of treating a subject having vernal conjunctivitis which include administering an anti-IL-4R antibody (e.g., an anti-IL-4Rα antibody, e.g., dupilumab). Also disclosed are methods of alleviating, ameliorating, or preventing reactions associated with vernal conjunctivitis, which include administering an anti-IL-4R antibody (e.g., an anti-IL-4Rα antibody, e.g., dupilumab) to a subject.

Eczematous Dermatitis of the Eyelid

Eczematous dermatitis of the eyelid a common condition that causes the skin on or around the eyelid to become dry, itchy, and irritated. In some instances, eczematous dermatitis of the eyelid is caused by an allergy. In some instances, eczematous dermatitis of the eyelid is caused by an irritation. In some instances, eczematous dermatitis causes an innate inflammatory reaction due to injury to the skin (e.g., eyelid). In some instances, subject having eczematous dermatitis have symptoms of itching, stinging or burning, and the lids are red and scaly. In some instances, the eyelids swell. In some instances, the eyelids become thickened with increased skin markings.

Disclosed herein are methods of treating a subject having eczematous dermatitis of the eyelid which include administering an anti-IL-4R antibody (e.g., an anti-IL-4Rα antibody, e.g., dupilumab). Also disclosed are methods of alleviating, ameliorating, or preventing reactions associated with eczematous dermatitis of the eyelid, which include administering an anti-IL-4R antibody (e.g., an anti-IL-4Rα antibody, e.g., dupilumab) to a subject.

Scleritis

Scleritis is an inflammation of the sclera, which is the white outer wall of the eye that forms the white of an eye. Scleritis often causes red or pink eye, tears, pain and sensitivity of the eye, and blurred vision. Left untreated, scleritis is a vision-threatening condition that can lead to permanent visual impairment. In some instances, a subject having scleritis presents with one or more of systemic lupus erythematosus, arthritis, other types of inflammatory arthritis (ankylosing spondylitis, reactive arthritis, gouty arthritis, psoriatic arthritis, relapsing polychondritis), polyarteritis nodosa, mixed connective tissue disease, progressive systemic sclerosis (scleroderma), granulomatous polyangiitis, polymyositis, Sjögren's syndrome, giant cell arteritis, inflammatory bowel disease, and allergic angiitis.

Disclosed herein are methods of treating a subject having scleritis which include administering an anti-IL-4R antibody (e.g., an anti-IL-4Rα antibody, e.g., dupilumab). Also disclosed are methods of alleviating, ameliorating, or preventing reactions associated with scleritis, which include administering an anti-IL-4R antibody (e.g., an anti-IL-4Rα antibody, e.g., dupilumab) to a subject.

Esophageal Indications

In some instances, disclosed are methods of treating esophageal-related indications, including Barrett's esophagus, eosinophilic esophagitis, achalasia, or gastroesophageal reflux disease (GERD).

Barrett's Esophagus

Barrett's esophagus is a condition characterized by alteration (subsequent to irritation) of the cells in the epithelial tissue that lines the lower portion of the esophagus. Frequent reflux of the stomach contents into the esophagus, over time, can lead to Barrett's esophagus. Patients with Barrett's esophagus are at risk for developing esophageal cancer (e.g., adenocarcinoma). While not wishing to be bound by a particular mechanism of action, administration of an anti-IL-4R antibody (e.g., an anti-IL-4Rα antibody, e.g., dupilumab) can benefit a patient with Barrett's esophagus by suppressing a TH2-type immune response.

Disclosed herein are methods of treating a subject having Barrett's esophagus which include administering an anti-IL-4R antibody (e.g., an anti-IL-4Rα antibody, e.g., dupilumab). Also disclosed are methods of alleviating, ameliorating, or preventing reactions associated with Barrett's esophagus, which include administering an anti-IL-4R antibody (e.g., an anti-IL-4Rα antibody, e.g., dupilumab). Also disclosed herein are treatments wherein an anti-IL-4R antibody (e.g., an anti-IL-4Rα antibody, e.g., dupilumab) is administered to a patient with esophagitis, to inhibit progression to Barrett's esophagus.

Eosinophilic Esophagitis

Esophageal stricture (narrowing of the esophagus) results from injury to the esophageal lining and leads to, inter alia, difficulty in swallowing (dysphagia), regurgitation of food or liquid, heartburn and unintended weight loss. Treatment of esophageal stricture is very important as it reduces quality of life due to dysphagia, weight loss, and nutritional imbalance. Esophageal stricture can be caused due to chronic ulceration or chronic inflammation, as a complication due to chemotherapy, radiotherapy, esophageal cancer or endoscopic surgery, peptic ulcers or gastroesophageal reflux. Esophageal stricture is also caused by eosinophilic esophagitis.

"Eosinophilic Esophagitis" (EoE), as used herein, means an inflammatory disease characterized by abnormal eosinophilic inflammation within the esophagus and esophageal dysfunction. EoE is found to be associated with food allergy in many patients. Some patients can also have concomitant asthma or an atopic disease such as atopic dermatitis, or allergic rhinitis. The primary symptoms of EoE include, but are not limited to, chest and abdominal pain, dysphagia, heartburn, food refusal, vomiting and food impaction. The clinical pathology of EoE is characterized by presence of ridges or trachea-like rings in the esophageal wall and eosinophilic infiltration in the esophageal mucosa. EoE is presently diagnosed by endoscopy of the esophagus followed by microscopic and biochemical analysis of the esophageal mucosal lining. EoE can be classified as allergic or non-allergic depending upon the status of the subject. The present disclosure includes methods to treat both allergic and non-allergic forms of EoE by administering an anti-IL-4R antibody (e.g., an anti-IL-4Rα antibody, e.g., dupilumab).

As used herein, the term "active EoE" refers to the EoE disease in a patient wherein the patient has ≥15 eosinophils/high powered field (hpf) in an esophageal biopsy even after 8 weeks of treatment with proton pump inhibitors (PPIs). The term also refers to the EoE disease in patients that exhibit frequent dysphagia, e.g., the patient has 2, 3, 4, 5, or more episodes of dysphagia per week. The term "active EoE" includes mild EoE as well as moderate-to-severe EoE. The term "moderate-to-severe" refers to EoE disease in patients that in addition to eosinophilia (e.g., ≥15 eosinophils/hpf in the esophageal mucosa) and frequent episodes of dysphagia, have SDI score≥2 and/or EEsAI score≥30, have duration of EoE for at least 2 years, and/or are non-responsive or resistant to prior therapy (including PPIs or esophageal dilation).

Disclosed herein are methods of treating a subject having at least one symptom or indication of EoE which include administering an anti-IL-4R antibody (e.g., an anti-IL-4Rα antibody, e.g., dupilumab). Also disclosed are methods of alleviating, ameliorating, or preventing reactions associated with at least one symptom or indication of EoE, which include administering an anti-IL-4R antibody (e.g., an anti-IL-4Rα antibody, e.g., dupilumab). EoE is further disclosed in U.S. Pat. No. 9,290,574 B2 and US-2019-0040126-A1, which is incorporated by reference in its entirety.

Disclosed herein are methods of treating a subject having EoE which include administering an anti-IL-4R antibody (e.g., an anti-IL-4Rα antibody, e.g., dupilumab). Also disclosed are methods of alleviating, ameliorating, or preventing reactions associated with EoE, which include administering an anti-IL-4R antibody (e.g., an anti-IL-4Rα antibody, e.g., dupilumab).

Eosinophilic Gastritis

Eosinophilic gastritis is a rare disease in which a type of white blood cell, the eosinophil, causes injury and inflammation to the stomach. Symptoms associated with eosinophilic gastritis include vomiting, nausea, difficulty feeding and/or gaining weight, poor growth, abdominal pain, anemia (low blood counts), and fatigue.

Eosinophilic gastroenteritis is a chronic condition. Mild and sporadic symptoms can be managed with reassurance and observation, whereas disabling gastrointestinal (GI) symptom flare-ups can often be controlled with oral corticosteroids. When the disease manifests in infancy and specific food sensitization can be identified, the likelihood of disease remission by late childhood is high. Gastrointestinal obstruction is the most common complication.

Disclosed herein are methods of treating a subject having at least one symptom or indication of eosinophilic gastritis which include administering an anti-IL-4R antibody (e.g., an anti-IL-4Rα antibody, e.g., dupilumab). Also disclosed are methods of alleviating, ameliorating, or preventing reactions associated with at least one symptom or indication of eosinophilic gastritis, which include administering an anti-IL-4R antibody (e.g., an anti-IL-4Rα antibody, e.g., dupilumab).

Disclosed herein are methods of treating a subject having eosinophilic gastritis which include administering an anti-IL-4R antibody (e.g., an anti-IL-4Rα antibody, e.g., dupilumab). Also disclosed are methods of alleviating, ameliorating, or preventing reactions associated with eosinophilic gastritis, which include administering an anti-IL-4R antibody (e.g., an anti-IL-4Rα antibody, e.g., dupilumab).

Skin-Related Indications

In some instances, disclosed are methods of treating skin-related indications, including allergic contact dermatitis, dermatitis herpetiformis, dyshidrotic eczema, chronic hand eczema, nummular dermatitis, scleroderma, systemic scleroderma, dermatomyositis, epidermolysis bullosa, hypertrophic scarring, urticaria, skin infections, alopecia areata, prurigo nodularis, bullous pemphigoid, or Netherton syndrome.

Allergic Contact Dermatitis (ACD)

Allergic contact dermatitis (ACD) is a red, itchy rash caused by direct contact with a substance (e.g., a chemical or chemicals) or an allergic reaction to it. ACD can manifest as mild to severe, acute and short lived, or chronic. Although the rash is not contagious or life-threatening, it can be very uncomfortable. Many substances can cause such reactions, including soaps, cosmetics, fragrances, jewelry and plants. In some instances, allergic contact dermatitis (ACD) presents as an adverse event associated with implantable medical devices that contain allergenic materials such as nickel. In some instances, ACD is caused by seasonally-exposed substances. In some instances, ACD results from contact with one or more of poison ivy, poison oak, or poison sumac. In some instances, the subject has been previously exposed and has become sensitized to the seasonally-exposed substance after exposure to a toxic agent.

In some instances, the allergic contact dermatitis is chronic allergic contact dermatitis (CACD). In some instances, CACD results from adverse event associated with implantable medical devices over time. Chronic inflammation from metal joint replacements may cause complications at the implant site, which mostly present as chronic joint pain, swelling, loosening, and joint failure. In some instances, CACD results from complications from a surgical wound. In some instances, CACD results from a subject's sun-exposed skin. In some instances, the subject having ACD or CACD develops skin cancer. See e.g., Demehri et al., *J Clin Invest*. 2014 Nov. 3; 124(11): 5037-5041, which is incorporated by reference in its entirety.

Disclosed herein are methods of treating a subject having allergic contact dermatitis which include administering an anti-IL-4R antibody (e.g., an anti-IL-4Rα antibody, e.g., dupilumab). Also disclosed are methods of alleviating, ameliorating, or preventing reactions associated with allergic contact dermatitis, which include administering an anti-IL-4R antibody (e.g., an anti-IL-4Rα antibody, e.g., dupilumab).

Disclosed herein are methods of treating a subject having chronic allergic contact dermatitis which include administering an anti-IL-4R antibody (e.g., an anti-IL-4Rα antibody, e.g., dupilumab). Also disclosed are methods of alleviating, ameliorating, or preventing reactions associated with chronic allergic contact dermatitis, which include administering an anti-IL-4R antibody (e.g., an anti-IL-4Rα antibody, e.g., dupilumab).

Dermatitis

Dermatitis is a condition that has many causes and occurs in many forms. It usually involves itchy, dry skin or a rash on swollen, reddened skin. Or it may cause the skin to blister, ooze, crust, or flake off. In some instances, dermatitis is unspecified dermatitis. In some instances, dermatitis is specified dermatitis.

Disclosed herein are methods of treating a subject having unspecified dermatitis by administering an anti-IL-4R antibody (e.g., an anti-IL-4Rα antibody, e.g., dupilumab) to the subject. Also disclosed herein are methods of alleviating, ameliorating, or preventing reactions associated with unspecified dermatitis by administering an anti-IL-4R antibody (e.g., an anti-IL-4Rα antibody, e.g., dupilumab) to the patient.

Disclosed herein are methods of treating a subject having a specified dermatitis by administering an anti-IL-4R antibody (e.g., an anti-IL-4Rα antibody, e.g., dupilumab) to the subject. Also disclosed herein are methods of alleviating, ameliorating, or preventing reactions associated with a specified dermatitis by administering an anti-IL-4R antibody (e.g., an anti-IL-4Rα antibody, e.g., dupilumab) to the patient.

Dermatitis Herpetiformis Dermatitis herpetiformis, also known as Duhring's disease, is a chronic skin condition characterized by blistering skin lesions, cutaneous IgA deposits, and itching. Patients have an immunobullous skin disorder with an associated gluten sensitive enteropathy, which is mediated by a Th2 immune response. An anti-IL-4R antibody (e.g., an anti-IL-4Rα antibody, e.g., dupilumab) is administered in accordance with the present disclosure, to inhibit IL-4 and the Th2 response, thus promoting healing of current lesions and reducing or preventing the formation of blisters on the extensor body surfaces.

Disclosed herein are methods of treating a subject having dermatitis herpetiformis which include administering an anti-IL-4R antibody (e.g., an anti-IL-4Rα antibody, e.g., dupilumab) to a subject. Also disclosed are methods of alleviating, ameliorating, or preventing reactions associated with dermatitis herpetiformis, which include administering an anti-IL-4R antibody (e.g., an anti-IL-4Rα antibody, e.g., dupilumab) to a subject.

Nummular Dermatitis

Nummular eczema (also known as discoid eczema and nummular dermatitis) is a form of eczema that can occur at any age. The cause of nummular eczema (nummular dermatitis) is unknown, but it does not seem to run in families.

Known triggers for nummular eczema include damage to the skin such as through an insect bite, scrapes and scratches, chemical "burns;" a reaction to inflammation (as with atopic dermatitis and/or statis dermatitis) elsewhere on the body; dry skin especially in the winter; metals like nickel; poor blood flow or swelling in the lower legs; and medications like topical antibiotic creams, isotretinoin and interferon.

Disclosed herein are methods of treating a subject having nummular dermatitis which include administering an anti-IL-4R antibody (e.g., an anti-IL-4Rα antibody, e.g., dupilumab). Also disclosed are methods of alleviating, ameliorating, or preventing reactions associated with nummular dermatitis, which include administering an anti-IL-4R antibody (e.g., an anti-IL-4Rα antibody, e.g., dupilumab).

Eczematous Dermatitis and Allergic Dermatitis of the Eyelid

Eczematous dermatitis of the eyelid is a condition that causes the skin on or around the eyelid to become dry, itchy, and irritated. Allergic dermatitis of eyelid is an inflammatory reaction involving the eyelid skin that is caused by contact with a trigger substance (e.g., an allergy-causing substance). It may be due to allergy (allergic contact dermatitis) or irritation (irritant contact dermatitis). In some instances, dermatitis occurs on the upper eyelid. In some instances, dermatitis occurs on the lower eyelid. In some instances, dermatitis occurs on the upper eyelid and lower eyelid.

Disclosed herein are methods of treating a subject having eczematous dermatitis of the eyelid by administering an anti-IL-4R antibody (e.g., an anti-IL-4Rα antibody, e.g., dupilumab) to the subject. Also disclosed herein are methods of alleviating, ameliorating, or preventing reactions associated with eczematous dermatitis of the eyelid by administering an anti-IL-4R antibody (e.g., an anti-IL-4Rα antibody, e.g., dupilumab) to the patient.

Also disclosed herein are methods of treating a subject having allergic dermatitis of the eyelid by administering an anti-IL-4R antibody (e.g., an anti-IL-4Rα antibody, e.g., dupilumab) to the subject. Also disclosed herein are methods of alleviating, ameliorating, or preventing reactions associated with allergic dermatitis of the eyelid by administering an anti-IL-4R antibody (e.g., an anti-IL-4Rα antibody, e.g., dupilumab) to the patient.

Exfoliative Dermatitis

Exfoliative dermatitis is widespread erythema and scaling of the skin caused by preexisting skin disorders, drugs, cancer, or unknown causes. Symptoms and signs are pruritus, diffuse erythema, and epidermal sloughing. Exfoliative dermatitis is characterized by redness and scaling of the skin that begins in patches and spreads. The skin begins to slough off. This leads to problems with temperature regulation, protein and fluid loss, as well as an increased metabolic rate.

Disclosed herein are methods of treating a subject having exfoliative dermatitis by administering an anti-IL-4R antibody (e.g., an anti-IL-4Rα antibody, e.g., dupilumab) to the subject. Also disclosed herein are methods of alleviating, ameliorating, or preventing reactions associated with exfoliative dermatitis by administering an anti-IL-4R antibody (e.g., an anti-IL-4Rα antibody, e.g., dupilumab) to the patient.

Seborrheic Dermatitis

Seborrheic dermatitis is a skin disease that causes an itchy rash with flaky scales. It causes redness on light skin and light patches on darker skin. It's also called dandruff, cradle cap, seborrhea, seborrheic eczema, and seborrheic psoriasis. In some instances, seborrheic dermatitis is considered a chronic form of eczema. Seborrheic dermatitis appears on the body where there are a lot of sebaceous glands like the upper back, nose and scalp. People of any age can develop seborrheic dermatitis including infants (known as "cradle cap"). However, it most commonly affects adults between the ages of 30-60 and infants under 3 months.

Disclosed herein are methods of treating a subject having seborrheic dermatitis by administering an anti-IL-4R antibody (e.g., an anti-IL-4Rα antibody, e.g., dupilumab) to the subject. Also disclosed herein are methods of alleviating, ameliorating, or preventing reactions associated with seborrheic dermatitis by administering an anti-IL-4R antibody (e.g., an anti-IL-4Rα antibody, e.g., dupilumab) to the patient.

Epidermolysis Bullosa

Disclosed herein are subjects having epidermolysis bullosa. Epidermolysis bullosa is a group of rare diseases that cause fragile, blistering skin. In some instances, blisters appear in response to minor injury, even from heat, rubbing, scratching or adhesive tape. In severe cases, the blisters may occur inside the body, such as the lining of the mouth or the stomach. Symptoms of epidermolysis bullosa include one or more of fragile skin that blisters easily, especially on the hands and feet; nails that are thick or don't form; blisters inside the mouth and throat; thickened skin on the palms and soles of the feet; scarring alopecia; atrophic skin scarring; milia; tooth decay; dysphagia; or itchy, painful skin. In some instances, epidermolysis bullosa occurs in infancy or early childhood. In some instances, signs and symptoms present during adolescence or early adulthood.

Disclosed herein are methods of treating a subject having epidermolysis bullosa by administering an anti-IL-4R antibody (e.g., an anti-IL-4Rα antibody, e.g., dupilumab) to the subject. Also disclosed herein are methods of alleviating, ameliorating, or preventing reactions associated with epidermolysis bullosa by administering an anti-IL-4R antibody (e.g., an anti-IL-4Rα antibody, e.g., dupilumab) to the patient.

Dyshidrosis and Dyshidrotic Eczema

Dyshidrosis or dyshidrotic eczema is a distinct entity, often considered on the spectrum of atopic dermatitis, that primarily effects the palms and soles. It is often associated with considerable morbidity yet is frequently challenging to treat. Because of the association with seasonal allergies, the dyshidrotic eczema blisters are known to erupt more frequently during the spring allergy season. The blisters can last up to three weeks before they begin to dry and can sometimes be large and painful. As the blisters dry, they can turn into skin cracks or cause the skin to feel thick and spongy. Dyshidrotic eczema is also called cheiropompholyx, dyshidrosis, foot-and-hand eczema, pompholyx, or vesicular eczema, or palmoplantar eczema. In some instances, dyshidrosis is dyshidrosis pompholyx. Dyshidrosis pompholyx is a chronic dermatitis characterized by itchy blisters on the palms and sides of the fingers and sometimes on the soles of the feet.

Disclosed herein are methods of treating a subject having dyshidrosis or dyshidrotic eczema which include administering an anti-IL-4R antibody (e.g., an anti-IL-4Rα antibody, e.g., dupilumab). Also disclosed are methods of alleviating, ameliorating, or preventing reactions associated with dyshidrotic eczema, which include administering an anti-IL-4R antibody (e.g., an anti-IL-4Rα antibody, e.g., dupilumab).

Chronic Hand Eczema

Chronic hand eczema is a frequent chronic inflammatory skin disease which can have significant physical, psychological and social impact on daily activities. In chronic hand eczema, there is a close relationship between atopic dermatitis (that involves about 70% of patients), sensitization to environmental antigens and irritant triggering factors. Previously, the only systemic treatment labelled in chronic hand eczema, alitretinoin, is associated with moderate efficacy, high dropout due to adverse events and it requires strict contraception measures in women of child-bearing potential.

Disclosed herein are methods of treating a subject having chronic hand eczema which include administering an anti-IL-4R antibody (e.g., an anti-IL-4Rα antibody, e.g., dupilumab). Also disclosed are methods of alleviating, ameliorating, or preventing reactions associated with chronic hand eczema, which include administering an anti-IL-4R antibody (e.g., an anti-IL-4Rα antibody, e.g., dupilumab).

Scleroderma

Anti-IL-4Rα antibodies (e.g., dupilumab) can be administered to scleroderma patients in accordance with the disclosure. These can reduce IL-4-induced collagen synthesis by fibroblasts in the patients. The anti-IL-4Rα antibodies (e.g., dupilumab) can be employed in preventing or reducing fibrosis in skin and lung tissues, as well as other tissues in which fibrosis occurs in scleroderma patients, suppressing collagen synthesis in such tissues, and in treating scleroderma-related pulmonary disease.

Scleroderma can be localized scleroderma. Localized scleroderma is an autoimmune disease in which the immune system causes inflammation in the skin. The inflammation can trigger connective tissue cells to produce too much collagen, a fibrous protein that is a major part of many tissues. Excess collagen can lead to fibrosis, which is like scarring.

Localized scleroderma can be morphea scleroderma. Morphea scleroderma is an autoimmune disease that causes a skin condition that includes patches of reddish skin that thicken into firm, oval-shaped areas. Patches most often occur on the abdomen, stomach, and back, and sometimes on the face, arms and legs.

Disclosed herein are methods of treating a subject having scleroderma which include administering an anti-IL-4R antibody (e.g., an anti-IL-4Rα antibody, e.g., dupilumab). Also disclosed are methods of alleviating, ameliorating, or preventing reactions associated with scleroderma, which include administering an anti-IL-4R antibody (e.g., an anti-IL-4Rα antibody, e.g., dupilumab).

Limited Scleroderma

Limited scleroderma, also known as CREST syndrome, is one subtype of scleroderma. In some instances, the skin changes associated with limited scleroderma typically occur only in the lower arms and legs, below the elbows and knees, and sometimes affect the face and neck. In some instances, limited scleroderma can also affect the digestive tract, heart, lungs or kidneys. In some instances, symptoms of limited scleroderma include, but are not limited to, tight, hardened skin; Raynaud's phenomena; red spots or lines on skin; bumps under the skin; and swallowing difficulties.

Disclosed herein are methods of treating a subject having limited scleroderma which include administering an anti-IL-4R antibody (e.g., an anti-IL-4Rα antibody, e.g., dupilumab). Also disclosed are methods of alleviating, ameliorating, or preventing reactions associated with limited scleroderma, which include administering an anti-IL-4R antibody (e.g., an anti-IL-4Rα antibody, e.g., dupilumab).

Systemic Sclerosis

Systemic sclerosis, including diffuse systemic sclerosis, is a rare chronic disease of unknown cause characterized by diffuse fibrosis and vascular abnormalities in the skin, joints, and internal organs (especially the esophagus, lower gastrointestinal tract, lungs, heart, and kidneys). In some instances, systemic sclerosis includes limited systemic sclerosis, generalized systemic sclerosis with diffuse skin involvement, and systemic sclerosis sine scleroderma. Limited systemic sclerosis (CREST syndrome—calcinosis cutis, Raynaud phenomenon, esophageal dysmotility, sclerodactyly, telangiectasias), patients develop skin tightening over the face and distal to the elbows and knees and may also have gastroesophageal reflux disease. This type is characterized by slow progression and is often complicated by pulmonary hypertension. In generalized systemic sclerosis with diffuse skin involvement, patients have Raynaud phenomenon and gastrointestinal (GI) complications. This type typically evolves rapidly. Interstitial lung disease and scleroderma renal crisis are the major complications. In systemic sclerosis sine scleroderma, patients have systemic sclerosis-related antibodies and visceral manifestations of the disease but no skin tightening.

Disclosed herein are methods of treating a subject having systemic sclerosis which include administering an anti-IL-4R antibody (e.g., an anti-IL-4Rα antibody, e.g., dupilumab). Also disclosed are methods of alleviating, ameliorating, or preventing reactions associated with systemic sclerosis, which include administering an anti-IL-4R antibody (e.g., an anti-IL-4Rα antibody, e.g., dupilumab).

Disclosed herein are methods of treating a subject having diffuse systemic sclerosis which include administering an anti-IL-4R antibody (e.g., an anti-IL-4Rα antibody, e.g., dupilumab). Also disclosed are methods of alleviating, ameliorating, or preventing reactions associated with systemic sclerosis, which include administering an anti-IL-4R antibody (e.g., an anti-IL-4Rα antibody, e.g., dupilumab).

Hypertrophic Scarring

Anti-IL-4Rα antibodies (e.g., dupilumab) can be administered to patients who have, or are susceptible to developing, hypertrophic scarring. For example, an anti-IL-4R antibody (e.g., an anti-IL-4Rα antibody, e.g., dupilumab) can be administered to a burn patient. An immune response to burns and other injury is believed to play a role in the pathogenesis of hypertrophic scarring. Increased production of TH2-type cytokines, including IL-4, and reduced levels of certain TH1-type cytokines have been reported in burn patients who have hypertrophic scarring. The use of an anti-IL-4R antibody (e.g., an anti-IL-4Rα antibody, e.g., dupilumab) can benefit patients having (or at risk for developing) hypertrophic scarring, by suppressing a TH2-type immune response.

Disclosed herein are methods of treating a subject having hypertrophic scarring which include administering an anti-IL-4R antibody (e.g., an anti-IL-4Rα antibody, e.g., dupilumab). Also disclosed are methods of alleviating, ameliorating, or preventing reactions associated with hypertrophic scarring, which include administering an anti-IL-4R antibody (e.g., an anti-IL-4Rα antibody, e.g., dupilumab).

Urticaria

Urticaria (e.g., hives), especially chronic forms thereof such as chronic idiopathic urticaria (CIU), can be treated with an anti-IL-4R antibody (e.g., an anti-IL-4Rα antibody, e.g., dupilumab) in accordance with the present disclosure. CIU patients have higher serum levels of IL-4 than controls, and can have a predominantly TH2-type cytokine profile. Mast cells and Th2-type T cells are implicated as primary effector cells in chronic urticaria. IL-4 stimulates mast cell proliferation. Mast cell degranulation leads to histamine release, subsequent erythema, eosinophilia, redness of skin, and itching. In some aspects, an anti-IL-4R antibody (e.g., an anti-IL-4Rα antibody, e.g., dupilumab) is administered to inhibit IL-4 and reduce the TH2-type response, thereby helping to control a patient's urticaria.

Disclosed herein are methods of treating a subject having chronic spontaneous urticaria (CSU) which include administering an anti-IL-4R antibody (e.g., an anti-IL-4Rα antibody, e.g., dupilumab). Also disclosed are methods of alleviating, ameliorating, or preventing reactions associated with chronic spontaneous urticaria (CSU), which include administering an anti-IL-4R antibody (e.g., an anti-IL-4Rα antibody, e.g., dupilumab). In some aspects, a patient with CSU has the presence of itch and hives for more than 6 consecutive weeks at any time prior to enrollment despite current use of H1 antihistamine; has a urticaria activity score UAS7 score (range 0-42) equal or more than 16, and/or has be diagnosed with CSU for at least six months.

Disclosed herein are methods of treating a subject having cholinergic urticaria (CholU) which include administering an anti-IL-4R antibody (e.g., an anti-IL-4Rα antibody, e.g., dupilumab). Also disclosed are methods of alleviating, ameliorating, or preventing reactions associated with cholinergic urticaria (CholU), which include administering an anti-IL-4R antibody (e.g., an anti-IL-4Rα antibody, e.g., dupilumab). CholU is a type of physical urticaria (or hives) that appears when a person is sweating or their core body temperature increases. CholU is one of the physical urticaria characterized by small and pruritic weals which follow sweating events, including elevation of body temperature, physical exercise, intake of spicy foods, and emotional strains.

Disclosed herein are methods of treating a subject having CholU and is symptomatic despite H1-antihistamine treatment which include administering an anti-IL-4R antibody (e.g., an anti-IL-4Rα antibody, e.g., dupilumab). Also disclosed are methods of alleviating, ameliorating, or preventing reactions associated with CholU and is symptomatic despite H1-antihistamine treatment, which include administering an anti-IL-4R antibody (e.g., an anti-IL-4Rα antibody, e.g., dupilumab). In some aspects, an anti-IL-4R antibody (e.g., an anti-IL-4Rα antibody, e.g., dupilumab) is administered a subject having cholinergic urticaria (CholU) and is symptomatic despite H1-antihistamine treatment.

Disclosed herein are methods of treating a subject having urticaria which include administering an anti-IL-4R antibody (e.g., an anti-IL-4Rα antibody, e.g., dupilumab). Also disclosed are methods of alleviating, ameliorating, or preventing reactions associated with urticaria, which include administering an anti-IL-4R antibody (e.g., an anti-IL-4Rα antibody, e.g., dupilumab).

Chronic Inducible Urticaria (CIndU)

Disclosed herein are methods of treating Chronic Inducible Urticaria (CIndU). In some instances, CIndU is chronic urticaria that has an attributable cause or trigger and is classified according to the stimulus that provokes weals to develop. In some instances, these stimuli that provoke weals to develop include stroking or scratching the skin (dermographism), exercise, and emotional upset (cholinergic urticaria). In some instances, CIndU is triggered by one or more of cold, heat, pressure, sunlight (e.g., in solar urticaria), contact with water or various chemicals (contact urticaria), or vibration.

In some instances, CIndU presents with weals. In some instances, weals appear on any site of the body. In some instances, weals are a few millimeters (e.g., about 1, 2, 3, 4, 5, 6, 7, 8, 9, 10, 20, or 50 mm) In some instances, the weals are about 1, 2, 3, 4, 5, or more cm. In some instances, weals present as white or red and are often surrounded by a red flare. In some instances, weals appear within minutes (about 1, 2, 3, 4, 5, 10, 20 minutes) after the stimulus. In some instances, the weals last for a few minutes (e.g., about 5, 10, 15, 20, 25, 30, or 45 minutes) up to a few hours (e.g., about 1, 2, 3, 4, 5 hours, or more). In some instances, the weals are round. In some instances, the weals form rings.

Disclosed herein are methods of treating a subject having CIndU which include administering an anti-IL-4R antibody (e.g., an anti-IL-4Rα antibody, e.g., dupilumab). Also disclosed are methods of alleviating, ameliorating, or preventing reactions associated with CIndU, which include administering an anti-IL-4R antibody (e.g., an anti-IL-4Rα antibody, e.g., dupilumab).

Solar Urticaria

Solar urticaria is a rare condition in which exposure to ultraviolet or UV radiation, or sometimes even visible light, induces a case of urticaria or hives that can appear in both covered and uncovered areas of the skin. In some instances, a stinging, itchy rash develops within minutes after a short period to light. In some instances, the rash may look like weals. In some instances, the rash is red and/or swollen. In some instances, if large areas of the body are affected, the loss of fluid into the skin may result in light-headedness, headache, nausea and vomiting. In some instances, solar urticaria is IgE-mediated.

Disclosed herein are methods of treating a subject having solar urticaria which include administering an anti-IL-4R antibody (e.g., an anti-IL-4Rα antibody, e.g., dupilumab). Also disclosed are methods of alleviating, ameliorating, or preventing reactions associated with solar urticaria, which include administering an anti-IL-4R antibody (e.g., an anti-IL-4Rα antibody, e.g., dupilumab).

Skin Infections (Generally)

Skin infections generally occur at the sites of skin damage produced by, for example, atopic dermatitis, burns, cracks in the skin, cuts, blisters, insect bites, surgical wounds, intravenous drug injection or sites of intravenous catheter insertion, or long-term usage of topical steroids. The skin infections can be localized or diffuse with severe inflammation of the epidermal, dermal and sub-cutaneous layers of the skin. They can be caused by various microbes including, but not limited to *Staphylococcus aureus, Streptococcus* spp., *Pseudomonas aeruginosa, Bacteroides* spp., Herpes simplex virus, coxsackievirus, molluscum contagiosum virus, vaccinia virus, *Candida albicans*, fungi such as *Microsporum* spp. and *Trichophyton* spp., *Penicillium* spp *Cladosporium* spp., *Alternaria* spp., and *Aspergillus* spp. Treatment of skin infections is disclosed in U.S. Pat. No. 10,370,449 B2, which is incorporated by reference in its entirety.

Disclosed herein are methods of treating a subject having a skin infection which include administering an anti-IL-4R antibody (e.g., an anti-IL-4Rα antibody, e.g., dupilumab). Also disclosed are methods of alleviating, ameliorating, or preventing reactions associated with skin infection, which include administering an anti-IL-4R antibody (e.g., an anti-IL-4Rα antibody, e.g., dupilumab).

Alopecia Areata

Alopecia areata is a medical condition, in which the hair falls out in patches. The hair can fall out on the scalp or elsewhere on the face and body. Alopecia areata is an autoimmune skin disease, which means that the immune system is recognizing the hair follicles as foreign and attacking them, causing round patches of hair loss. It can progress to total scalp hair loss (alopecia totalis) or complete body hair loss (alopecia universalis). The scalp is the most commonly affected area, but the beard or any hair-bearing site can be affected alone or together with the scalp. Alopecia areata occurs in males and females of all ages, and is a highly unpredictable condition that tends to recur.

Disclosed herein are methods of treating a subject having alopecia areata which include administering an anti-IL-4R antibody (e.g., an anti-IL-4Rα antibody, e.g., dupilumab). Also disclosed are methods of alleviating, ameliorating, or preventing reactions associated with alopecia areata, which include administering an anti-IL-4R antibody (e.g., an anti-IL-4Rα antibody, e.g., dupilumab).

Disclosed herein are methods of treating a subject having moderate to severe alopecia areata involving 30-100% of the scalp which include administering an anti-IL-4R antibody (e.g., an anti-IL-4Rα antibody, e.g., dupilumab). Also disclosed are methods of alleviating, ameliorating, or preventing reactions associated with moderate to severe alopecia areata involving 30-100% of the scalp, which include administering an anti-IL-4R antibody (e.g., an anti-IL-4Rα antibody, e.g., dupilumab).

Disclosed herein are methods of treating a subject having alopecia areata and atopic dermatitis (AD) by administering an anti-IL-4R antibody (e.g., an anti-IL-4Rα antibody, e.g., dupilumab). Also disclosed are methods of alleviating, ameliorating, or preventing reactions associated with alopecia areata and AD, which include administering an anti-IL-4R antibody (e.g., an anti-IL-4Rα antibody, e.g., dupilumab).

Disclosed herein are methods of treating a subject having alopecia areata but does not have AD by administering an anti-IL-4R antibody (e.g., an anti-IL-4Rα antibody, e.g., dupilumab). Also disclosed are methods of alleviating, ameliorating, or preventing reactions associated with alopecia areata without AD, which include administering an anti-IL-4R antibody (e.g., an anti-IL-4Rα antibody, e.g., dupilumab).

Cicatricial Alopecia

Cicatricial alopecia, also known as scarring hair loss, scarring alopecia or cicatricial alopecia lichen planus, is a disease that includes destruction of the hair follicle, replacement with scar tissue, and leads to permanent hair loss. In some aspects, the hair follicle is the target of a destructive inflammatory process. In some aspects, destruction of the hair follicle is incidental to a non-follicle-directed process or external injury, such as severe infections, burns, radiation, or tumors. In some instances, hair loss can be gradual, without symptoms, and unnoticed for long periods.

In some instances, inflammation occurs at the site of cicatricial alopecia. In some instances inflammation involves infiltration predominantly of lymphocytes or neutrophils. Cicatricial alopecias that involve predominantly lymphocytic inflammation include lichen planopilaris, frontal fibrosing alopecia, central centrifugal alopecia, and pseudopelade (Brocq). Cicatricial alopecias that are due to predominantly neutrophilic inflammation include folliculitis decalvans and tufted folliculitis. Sometimes the inflammation shifts from a predominantly neutrophilic process to a lymphocytic process. Cicatricial alopecias with a mixed inflammatory infiltrate include dissecting cellulitis and folliculitis keloidalis.

Disclosed herein are methods of treating a subject having cicatricial alopecia by administering an anti-IL-4R antibody (e.g., an anti-IL-4Rα antibody, e.g., dupilumab). Also disclosed are methods of alleviating, ameliorating, or preventing reactions associated with cicatricial alopecia, which include administering an anti-IL-4R antibody (e.g., an anti-IL-4Rα antibody, e.g., dupilumab).

Prurigo Nodularis

Prurigo nodularis (PN) is a skin disease that causes hard, itchy lumps (nodules) to form on the skin. The itching (pruritus) can be intense, causing people to scratch themselves to the point of bleeding or pain. Scratching can cause more skin lesions to appear. The itching is worsened by heat, sweating, or irritation from clothing. In some cases, people with PN have a history of other diseases including eczema (atopic dermatitis), lymphoma, HIV infection, severe anemia, or kidney disease.

Diagnosis of PN is based on observing signs such as extremely itchy skin with the formation of nodules. In some cases, a skin biopsy is used to confirm the diagnosis. Treatment can include corticosteroid creams, oral medications, cryotherapy, or photochemotherapy.

Disclosed herein are methods of treating a subject having PN which include administering an anti-IL-4R antibody (e.g., an anti-IL-4Rα antibody, e.g., dupilumab). Also disclosed are methods of alleviating, ameliorating, or preventing reactions associated with PN, which include administering an anti-IL-4R antibody (e.g., an anti-IL-4Rα antibody, e.g., dupilumab).

Chronic Pruritus of Unknown Origin (CPUO)

Chronic pruritus of unknown origin (CPUO; also called chronic idiopathic pruritus and generalized pruritus of unknown origin) presents as an itch lasting for a period of time (e.g., greater than 4, 5, 6, or more weeks) in the absence of a known cause. In some instances, the pruritus in CPUO is localized. In some instances, the pruritus in CPUO is generalized. In some instances, the skin of a subject having CPUO appears normal. In some instances, the skin of a subject having CPUO appears erythematous, rough, or bumpy. Repeated scratching may lead to secondary skin changes, such as lichenification (thickening, hyperpigmentation and enhanced skin markings), bleeding, or a localized secondary bacterial infection. In some instances, CPUO presents with one or more skin changes selected from a localized thickened plaque (lichen simplex, a type of eczema); nodular prurigo, characterized by pruritic nodules 10 to 20 mm in diameter; impetigo due to secondary bacterial infection following scratching, or any combination thereof.

Disclosed herein are methods of treating a subject having CPUO which include administering an anti-IL-4R antibody (e.g., an anti-IL-4Rα antibody, e.g., dupilumab). Also disclosed are methods of alleviating, ameliorating, or preventing reactions associated with CPUO, which include administering an anti-IL-4R antibody (e.g., an anti-IL-4Rα antibody, e.g., dupilumab).

Bullous Pemphigoid

Bullous pemphigoid is a rare skin condition that causes large, fluid-filled blisters. They develop on areas of skin that often flex, such as the lower abdomen, upper thighs or armpits. Bullous pemphigoid is most common in older adults.

Bullous pemphigoid occurs when the immune system attacks a thin layer of tissue below the outer layer of skin. The reason for this abnormal immune response is unknown, although it sometimes can be triggered by taking certain medications.

Bullous pemphigoid often goes away on its own in a few months, but can take as many as five years to resolve. Treatment usually helps heal the blisters and ease any itching. It can include corticosteroid medications, such as prednisone, and other drugs that suppress the immune system. Bullous pemphigoid can be life-threatening, especially for older people who are already in poor health.

Symptoms of bullous pemphigoid include one or more of itching skin, weeks or months before blisters form; large blisters that don't easily rupture when touched, often along creases or folds in the skin; skin around the blisters that is normal, reddish or darker than normal; eczema or a hive-like rash; and/or small blisters or sores in the mouth or other mucous membranes (benign mucous membrane pemphigoid).

Disclosed herein are methods of treating a subject having bullous pemphigoid which include administering an anti-IL-4R antibody (e.g., an anti-IL-4Rα antibody, e.g., dupilumab). Also disclosed are methods of alleviating, ameliorating, or preventing reactions associated with bullous pemphigoid, which include administering an anti-IL-4R antibody (e.g., an anti-IL-4Rα antibody, e.g., dupilumab).

Netherton Syndrome

Netherton syndrome is a disorder that affects the skin, hair, and immune system. Newborns with Netherton syndrome have skin that is red and scaly (ichthyosiform erythroderma), and the skin can leak fluid. Some affected infants are born with a tight, clear sheath covering their skin called a collodion membrane. This membrane is usually shed during the first few weeks of life. Because newborns with this disorder are missing the protection provided by normal skin, they are at risk of becoming dehydrated and developing infections in the skin or throughout the body (sepsis), which can be life-threatening. Affected babies can also fail to grow and gain weight at the expected rate (failure to thrive). The health of older children and adults with Netherton syndrome usually improves, although they often remain underweight and of short stature.

After infancy, the severity of the skin abnormalities varies among people with Netherton syndrome and can fluctuate over time. The skin can continue to be red and scaly, especially during the first few years of life. Some affected individuals have intermittent redness or experience outbreaks of a distinctive skin abnormality called ichthyosis linearis circumflexa, involving patches of multiple ring-like lesions. The triggers for the outbreaks are not known, but researchers suggest that stress or infections can be involved.

Itchiness is a common problem for affected individuals, and scratching can lead to frequent infections. Dead skin cells are shed at an abnormal rate and often accumulate in the ear canals, which can affect hearing if not removed regularly. The skin is abnormally absorbent of substances such as lotions and ointments, which can result in excessive blood levels of some topical medications. Because the ability of the skin to protect against heat and cold is impaired, affected individuals can have difficulty regulating their body temperature.

People with Netherton syndrome have hair that is fragile and breaks easily. Some strands of hair vary in diameter, with thicker and thinner spots. This feature is known as bamboo hair, trichorrhexis nodosa, or trichorrhexis invaginata. In addition to the hair on the scalp, the eyelashes and eyebrows can be affected. The hair abnormality in Netherton syndrome cannot be noticed in infancy because babies often have sparse hair.

Most people with Netherton syndrome have immune system-related problems such as food allergies, hay fever, asthma, or an inflammatory skin disorder called eczema.

Disclosed herein are methods of treating a subject having Netherton syndrome which include administering an anti-IL-4R antibody (e.g., an anti-IL-4Rα antibody, e.g., dupilumab). Also disclosed are methods of alleviating, ameliorating, or preventing reactions associated with Netherton syndrome, which include administering an anti-IL-4R antibody (e.g., an anti-IL-4Rα antibody, e.g., dupilumab).

Atopic Dermatitis (AD)

Atopic dermatitis (AD) is a chronic/relapsing inflammatory skin disease characterized by intense pruritus (e.g., severe itch) and by scaly and dry eczematous lesions. AD is often associated with other atopic disorders such as allergic rhinitis and asthma.

The pathophysiology of AD is influenced by a complex interplay between Immunoglobulin E (IgE)-mediated sensitization, the immune system, and environmental factors. The primary skin defect can be an immunological disturbance that causes IgE-mediated sensitization, with epithelial-barrier dysfunction that is the consequence of both genetic mutations and local inflammation. AD often begins in childhood before age 5 and can persist into adulthood.

Disclosed herein are methods of treating a subject having symptoms of AD which include administering an anti-IL-4R antibody (e.g., an anti-IL-4Rα antibody, e.g., dupilumab). In some aspects, AD is not moderate-to-severe atopic dermatitis. In some aspects, disclosed herein are methods of treating an adult subject having AD (but not moderate-to-severe atopic dermatitis). Also disclosed are methods of alleviating, ameliorating, or preventing reactions associated with symptoms of AD, which include administering an anti-IL-4R antibody (e.g., an anti-IL-4Rα antibody, e.g., dupilumab). Treatment of AD is disclosed in US-2017-0333557-A1 and U.S. Pat. No. 10,370,449 B2, each of which is incorporated by reference in its entirety.

Also disclosed herein are methods for treating patients with severe AD that is resistant to treatment or is inadequately controlled by systemic therapy (including a systemic immunosuppressant). In some instances, the present disclosure includes methods of treating patients with severe AD that is uncontrolled despite treatment with a systemic therapeutic agent. In some instances, the present disclosure includes methods of treating patients with severe AD for whom treatment with a systemic therapeutic agent (e.g., a systemic immunosuppressant) is medically inadvisable.

Disclosed herein are methods of treating a subject having severe AD which include administering an anti-IL-4R antibody (e.g., an anti-IL-4Rα antibody, e.g., dupilumab). Also disclosed are methods of alleviating, ameliorating, or preventing reactions associated with severe AD, which include administering an anti-IL-4R antibody (e.g., an anti-IL-4Rα antibody, e.g., dupilumab). In other embodiments, an anti-IL-4R antibody (e.g., an anti-IL-4Rα antibody, e.g., dupilumab) is administered in combination with a topical therapy (such as a topical corticosteroid or a topical calcineurin inhibitor). In certain embodiments, the systemic therapeutic agent is an immunosuppressant selected from cyclosporine A, methotrexate, mycophenolate mofetil, azathioprine, an oral corticosteroid, and/or interferon-gamma. Methods of treating subjects who do not respond adequately to systemic therapy is disclosed further in US-2018-0078603-A1, which is incorporated by reference in its entirety.

Ichthyosis and Congenital Ichthyosis

Ichthyosis is a family of genetic skin disorders characterized by dry and scaling skin that may be thickened or very thin. Ichthyosis usually presents at birth, or within the first year, and continues to affect the patient throughout their lifetime. Congenital ichthyosis is an autosomal recessive disorder (also called autosomal recessive congenital ichthyosis (ARCI)) that includes a heterogeneous group of disorders of keratinization characterized primarily by abnormal skin scaling over the whole body. In some instances, the main skin phenotypes of a subject having congenital ichthyosis are lamellar ichthyosis (LI) and nonbullous congenital ichthyosiform erythroderma (NCIE). In some instances subjects with congenital ichthyosis have scales that cover the entire body surface, including the flexural folds, and the scales are highly variable in size and color. In some instances, erythema is very mild and almost invisible. In some instances, a subject having congenital ichthyosis exhibits scarring alopecia, and many have secondary anhidrosis. In some instances, ichthyosis includes one or more of ichthyosis vulgaris, lamellar ichthyosis, epidermolytic hyperkeratosis, congenital ichthyosiform erythroderma, or X-linked ichthyosis.

Disclosed herein are methods of treating a subject having ichthyosis or congenital ichthyosis which include administering an anti-IL-4R antibody (e.g., an anti-IL-4Rα antibody, e.g., dupilumab). Also disclosed are methods of alleviating, ameliorating, or preventing reactions associated with ichthyosis or congenital ichthyosis, which include administering an anti-IL-4R antibody (e.g., an anti-IL-4Rα antibody, e.g., dupilumab).

Erythema Nodosum

Erythema nodosum is a type of skin inflammation that is located in a part of the fatty layer of skin. It is characterized by tender, red bumps, usually found symmetrically on the shins; fever; joint pain; and enlarged lymph nodes in the chest. Erythema nodosum can present with other conditions, including Streptococcal infections, sarcoidosis, Coccidioidomycosis, histoplasmosis, tuberculosis, psittacosis, ulcerative colitis or Crohn's disease, cancer, and pregnancy. In some instances, Erythema nodosum is acute. In some instances, Erythema nodosum is chronic.

Disclosed herein are methods of treating a subject having erythema nodosum which include administering an anti-IL-4R antibody (e.g., an anti-IL-4Rα antibody, e.g., dupilumab). Also disclosed are methods of alleviating, ameliorating, or preventing reactions associated with erythema nodosum, which include administering an anti-IL-4R antibody (e.g., an anti-IL-4Rα antibody, e.g., dupilumab).

Pyoderma Gangrenosum

Pyoderma gangrenosum is a rare condition that causes large, often painful ulcers to develop on skin. Classic pyoderma gangrenosum can occur on any skin surface. In some instances, the ulcers develop on a subject's legs. In some instances, pyoderma gangrenosum starts with a small, red bump on skin, which may resemble a spider bite. In some instances, within days, this bump can develop into a large, painful open sore. In some instances, pyoderma gangrenosum is chronic. In some instances, a subject with pyoderma gangrenosum presents with a fever and/or joint pain.

Disclosed herein are methods of treating a subject having pyoderma gangrenosum which include administering an anti-IL-4R antibody (e.g., an anti-IL-4Rα antibody, e.g., dupilumab). Also disclosed are methods of alleviating, ameliorating, or preventing reactions associated with pyoderma gangrenosum, which include administering an anti-IL-4R antibody (e.g., an anti-IL-4Rα antibody, e.g., dupilumab).

Erythema Multiforme

Erythema multiforme (EM) is an acute, sometimes self-limited, and sometimes recurring skin condition that is sometimes associated with certain infections and other various triggers. In some instances, EM is a skin condition caused by a hypersensitivity reaction to infections or drugs. It consists of a polymorphous eruption of macules, papules, and characteristic "target" lesions that are symmetrically distributed with a propensity for the distal extremities. There is minimal mucosal involvement.

Disclosed herein are methods of treating a subject having EM which include administering an anti-IL-4R antibody (e.g., an anti-IL-4Rα antibody, e.g., dupilumab). Also disclosed are methods of alleviating, ameliorating, or preventing reactions associated with EM, which include administering an anti-IL-4R antibody (e.g., an anti-IL-4Rα antibody, e.g., dupilumab).

Hemangiomas

Hemangiomas of skin and subcutaneous tissue are benign lesions with increased numbers of blood vessels on or under the surface of the skin. Hemangiomas of the skin are generally deep red or blue-purple. They appear as raised lesions or tumors on the skin. The deeper the hemangioma, the darker its color. Hemangiomas can affect numerous tissue types (individually or in combination), including skin, subcutaneous tissue, viscera, muscle, synovium, and bone. In some instances, hemangiomas do not spread to avascular tissue such as cartilage. In some aspects, hemangiomas occur in infants. In some aspects, hemangiomas occur in premature or low birth weight infants.

Disclosed herein are methods of treating a subject having hemangiomas of skin and/or subcutaneous tissue which include administering an anti-IL-4R antibody (e.g., an anti-IL-4Rα antibody, e.g., dupilumab). Also disclosed are methods of alleviating, ameliorating, or preventing reactions associated with hemangiomas of skin and/or subcutaneous tissue, which include administering an anti-IL-4R antibody (e.g., an anti-IL-4Rα antibody, e.g., dupilumab).

Lichen Planus

Lichen planus is a condition that can cause swelling and irritation in the skin, hair, nails and mucous membranes. On the skin, lichen planus usually appears as purplish, itchy, flat bumps that develop over several weeks. In the mouth, vagina, and other areas covered by a mucous membrane, lichen planus forms lacy white patches, sometimes with painful sores. In some instances, a subject with lichen planus presents with one or more of purplish, flat bumps, most often on the inner forearm, wrist or ankle, and sometimes the genitals; itching; blisters that break to form scabs or crusts; lacy white patches in the mouth or on the lips or tongue; painful sores in the mouth or vagina; hair loss; change in scalp color; and/or nail damage or loss. In some instances, lichen planus is triggered by hepatitis C infection, flu vaccine, certain pigments, chemicals and metals; pain relievers, such as ibuprofen and naproxen, certain medications for heart disease, high blood pressure, or arthritis.

Disclosed herein are methods of treating a subject having lichen planus which include administering an anti-IL-4R antibody (e.g., an anti-IL-4Rα antibody, e.g., dupilumab). Also disclosed are methods of alleviating, ameliorating, or preventing reactions associated with lichen planus, which include administering an anti-IL-4R antibody (e.g., an anti-IL-4Rα antibody, e.g., dupilumab).

Granuloma Faciale

Granuloma faciale is a rare benign skin condition, characterized by single or multiple erythematous (red) papules, plaques or nodules. In some instances, granuloma faciale is characterized by chronic leukocitoclastic vasculitis with dense infiltration of polimorfonucleares. In some instances, granuloma faciale affects facial areas of a subject. In some instances, a subject having granuloma faciale develops single or multiple cutaneous nodules on sun-exposed areas.

Disclosed herein are methods of treating a subject having granuloma faciale which include administering an anti-IL-4R antibody (e.g., an anti-IL-4Rα antibody, e.g., dupilumab). Also disclosed are methods of alleviating, ameliorating, or preventing reactions associated with granuloma faciale, which include administering an anti-IL-4R antibody (e.g., an anti-IL-4Rα antibody, e.g., dupilumab).

Exfoliative Dermatitis

Exfoliative dermatitis (also called erythroderma) is widespread erythema and scaling of the skin. In some instances, exfoliative dermatitis includes redness and peeling of the skin over large areas of the body. In some instances, it is caused by preexisting skin disorders, drugs, or cancer. In some instances, symptoms and signs are pruritus, diffuse erythema, epidermal sloughing, malaise, and chills. In some instances, diffuse erythema initially occurs in patches but spreads and involves all or nearly all of the body. In some instances, extensive epidermal sloughing leads to abnormal thermoregulation, nutritional deficiencies because of extensive protein losses, increased metabolic rate with a hypercatabolic state, and hypovolemia due to transdermal fluid losses.

Disclosed herein are methods of treating a subject having exfoliative dermatitis which include administering an anti-IL-4R antibody (e.g., an anti-IL-4Rα antibody, e.g., dupilumab). Also disclosed are methods of alleviating, ameliorating, or preventing reactions associated with exfoliative dermatitis, which include administering an anti-IL-4R antibody (e.g., an anti-IL-4Rα antibody, e.g., dupilumab).

Eccrine Sweat Disorders

Eccrine Sweat Disorders are a group of dysregulatory disorders of the major sweat glands of the human body (i.e., eccrine sweat glands). Eccrine sweat glands are found in virtually all skin, with the highest density in palm and soles, then on the head, but much less on the trunk and the extremities. Eccrine glands are sympathetically innervated, distributed over the entire body, and active from birth. Their secretions are watery and serve to cool the body in hot environments or during activity. Eccrine Sweat Disorders include, but are not limited to, hyperhidrosis, hypohidrosis, and miliaria. In some instances, alterations in the electrolyte composition of eccrine sweat can be observed in several systemic diseases, most notably cystic fibrosis.

Disclosed herein are methods of treating a subject having an eccrine sweat disorder which include administering an anti-IL-4R antibody (e.g., an anti-IL-4Rα antibody, e.g., dupilumab). Also disclosed are methods of alleviating, ameliorating, or preventing reactions associated with eccrine sweat disorder, which include administering an anti-IL-4R antibody (e.g., an anti-IL-4Rα antibody, e.g., dupilumab).

Nonsuppurative Otitis Media

Nonsuppurative otitis media, or acute otitis media (AOM) or Otitis media with effusion, is an otitis media which involves transudation of fluid in the middle ear without pus formation. In some instances, the subject having nonsuppurative otitis media is a child.

Disclosed herein are methods of treating a subject having nonsuppurative otitis media which include administering an anti-IL-4R antibody (e.g., an anti-IL-4Rα antibody, e.g., dupilumab). Also disclosed are methods of alleviating, ameliorating, or preventing reactions associated with nonsuppurative otitis media, which include administering an anti-IL-4R antibody (e.g., an anti-IL-4Rα antibody, e.g., dupilumab).

Acne

Acne is a skin condition that occurs when the hair follicles become plugged with oil and dead skin cells. It often causes whiteheads, blackheads or pimples, and usually appears on the face, forehead, chest, upper back and shoulders. Acne is most common among teenagers, though it affects people of all ages. In some instances, acne can cause emotional distress and scar the skin. Symptoms associated with acne include whiteheads (closed plugged pores); blackheads (open plugged pores); small red, tender bumps (papules); pimples (pustules), which are papules with pus at their tips; large, solid, painful lumps beneath the surface of the skin (nodules); and painful, pus-filled lumps beneath the surface of the skin (cystic lesions).

Disclosed herein are methods of treating a subject having acne which include administering an anti-IL-4R antibody (e.g., an anti-IL-4Rα antibody, e.g., dupilumab). Also disclosed are methods of alleviating, ameliorating, or preventing reactions associated with acne, which include administering an anti-IL-4R antibody (e.g., an anti-IL-4Rα antibody, e.g., dupilumab).

Pityriasis Rosea

Pityriasis rosea (or pityriasis; or rosea) is a rash that usually begins as a large circular or oval spot on the chest, abdomen, or back. In some instances, this spot can be up to 4 inches (10 centimeters) across.

In some instances, pityriasis rosea begins with a large, slightly raised, scaly patch—called the herald patch—on the back, chest or abdomen. In some instances, before the herald patch appears, a subject experiences headache, fatigue, fever, or sore throat. In some instances, a few days to a few weeks after the herald patch appears, a subject presents with smaller scaly spots across the back, chest, or abdomen that resemble a pine-tree pattern. In some instances, the rash causes itching, which is occasionally severe. In some instances, pityriasis rosea is triggered by a viral infection. In some instances, the viral infection is from a herpes virus.

Disclosed herein are methods of treating a subject having pityriasis rosea which include administering an anti-IL-4R antibody (e.g., an anti-IL-4Rα antibody, e.g., dupilumab). Also disclosed are methods of alleviating, ameliorating, or preventing reactions associated with pityriasis rosea, which include administering an anti-IL-4R antibody (e.g., an anti-IL-4Rα antibody, e.g., dupilumab).

Melanocytic Nevi

Melanocytic nevi are benign neoplasms or hamartomas composed of melanocytes. In some instances, disclosed herein are subjects having melanocytic nevi. Melanocytic nevi can be congenital or acquired. Melanocytic nevi are neoplasms resulting from the proliferation of melanocytes, the normal pigment-producing cells in the skin. Nevi are growth arrested, clonal neoplasms of melanocytes initiated by well-defined oncogenic mutations in the mitogen-activated protein kinase (MAPK) pathway, most commonly by BRAFV600E-activating mutation. In addition, they are pigmented in nature and located in skin, making nevi readily identifiable by visual examination and allowing for monitoring in real time Disclosed herein are methods of treating a subject having melanocytic nevi by administering an anti-IL-4R antibody (e.g., an anti-IL-4Rα antibody, e.g., dupilumab) to the subject. Also disclosed herein are methods of alleviating, ameliorating, or preventing reactions associated with melanocytic nevi by administering an anti-IL-4R antibody (e.g., an anti-IL-4Rα antibody, e.g., dupilumab) to the patient.

Pruritus

Pruritus (e.g., itchy skin) is defined as an unpleasant sensation of the skin that provokes the urge to scratch. It is a characteristic feature of many skin diseases and an unusual sign of some systemic diseases. In some instances, pruritus is localized. In some instances, pruritus is generalized. In some instances, pruritus is an acute condition. In some instances, pruritus is a chronic condition. Pruritus is a common manifestation of dermatologic diseases, including eczema, atopic dermatitis, and allergic contact dermatitis.

Disclosed herein are methods of treating a subject having pruritus by administering an anti-IL-4R antibody (e.g., an anti-IL-4Rα antibody, e.g., dupilumab) to the subject. Also disclosed herein are methods of alleviating, ameliorating, or preventing reactions associated with pruritus by administering an anti-IL-4R antibody (e.g., an anti-IL-4Rα antibody, e.g., dupilumab) to the patient.

Vitiligo

Vitiligo is a long-term skin condition characterized by patches of the skin losing pigment. The patches of skin affected become white and usually have sharp margins. In some instances, the hair from the skin of a subject having vitiligo become white. In some instances, the inside of the mouth and nose become white. Normally, the color of hair and skin is determined by melanin. Vitiligo occurs when the skin or hair cells cease making or make reduced amounts of melanin. In some instances, the discoloration first shows on sun-exposed areas, such as the hands, feet, arms, face and lips. In some instances, subjects under age 20 present with vitiligo.

Disclosed herein are methods of treating a subject having vitiligo by administering an anti-IL-4R antibody (e.g., an anti-IL-4Rα antibody, e.g., dupilumab) to the subject. Also disclosed herein are methods of alleviating, ameliorating, or preventing reactions associated with vitiligo by administering an anti-IL-4R antibody (e.g., an anti-IL-4Rα antibody, e.g., dupilumab) to the patient.

Phakomatoses, not Elsewhere Classified

Phakomatoses are a group of neurocutaneous disorders characterized by involvement of structures that arise from the embryonic ectoderm. The phakomatoses are a heterogeneous group of disorders primarily involving structures derived from the embryologic neuroectoderm. However, they commonly exhibit associated pathology in tissues derived from all three germ cell layers, most notably ectoderm (skin) and mesoderm (connective tissue). All the phakomatoses involve the central nervous system (CNS); some also affect the peripheral nervous system. Most are associated with cutaneous signs, and many have visceral and connective tissue (mesodermal) changes.

Disclosed herein are methods of treating a subject having one or more phakomatoses, not elsewhere classified by administering an anti-IL-4R antibody (e.g., an anti-IL-4Rα antibody, e.g., dupilumab) to the subject. Also disclosed herein are methods of alleviating, ameliorating, or preventing reactions associated with one or more phakomatoses, not elsewhere classified by administering an anti-IL-4R antibody (e.g., an anti-IL-4Rα antibody, e.g., dupilumab) to the patient.

Stevens-Johnson Syndrome

Stevens-Johnson syndrome is a rare, serious disorder of the skin and mucous membranes. It is typically a reaction to a medication or an infection. Often, it begins with flu-like symptoms, followed by a painful red or purplish rash that spreads and blisters. Then the top layer of the affected skin dies, sheds and then heals. Symptoms associated with Stevens-Johnson syndrome include fever; unexplained widespread skin pain; a red or purple skin rash that spreads; blisters on skin and the mucous membranes of the mouth, nose, eyes and genitals; and shedding of skin within days after blisters form.

Disclosed herein are methods of treating a subject having Stevens-Johnson syndrome by administering an anti-IL-4R antibody (e.g., an anti-IL-4Rα antibody, e.g., dupilumab) to the subject. Also disclosed herein are methods of alleviating, ameliorating, or preventing reactions associated with Stevens-Johnson syndrome by administering an anti-IL-4R antibody (e.g., an anti-IL-4Rα antibody, e.g., dupilumab) to the patient.

Gastrointestinal Indications

In some instances, disclosed are methods of treating gastrointestinal-related indications, including gastrointestinal-related disorder is ulcerative colitis, Whipple's disease, Behçet's disease, Wegener granulomatosis, or GERD.

Ulcerative Colitis

IL-4 is implicated in the pathogenesis of ulcerative colitis. Th2-type cytokines including IL-4 can predominate in the colonic mucosa of patients with this disorder. The use of an anti-IL-4R antibody (e.g., an anti-IL-4Rα antibody, e.g., dupilumab) to suppress the TH2 response can alleviate this condition.

In addition to ulcerative colitis, other disorders of the gastrointestinal tract or digestive system can be treated with an anti-IL-4R antibody (e.g., an anti-IL-4Rα antibody, e.g., dupilumab). Examples of such disorders include, but are not limited to, inflammatory bowel disease (IBD), with ulcerative colitis and Crohn's Disease being forms of IBD, gastritis, ulcers, and mucosal inflammation.

Any gastrointestinal condition in which IL-4 plays a role can be treated with an anti-IL-4R antibody (e.g., an anti-IL-4Rα antibody, e.g., dupilumab) in accordance with the present disclosure. For example, conditions involving IL-4-induced inflammation of part of the gastrointestinal tract can be treated with an anti-IL-4R antibody (e.g., an anti-IL-4Rα antibody, e.g., dupilumab). Particular embodiments are directed to treatment of chronic inflammatory conditions in the gastrointestinal tract.

Other embodiments are directed to conditions in which IL-4-induced barrier disruption plays a role, e.g., conditions characterized by decreased epithelial barrier function in at least a portion of the gastrointestinal tract. Such conditions can, for example, involve damage to the epithelium that is induced by IL-4, directly or indirectly.

The intestinal epithelium forms a relatively impermeable barrier between the lumen and the submucosa. Disruption of the epithelial barrier has been associated with conditions such as inflammatory bowel disease. See the discussion in Youakim, A. and M. Ahdieh (Am. J. Physiol. 276 (Gastrointest. Liver Physiol. 39):G1279-G1288, 1999), hereby incorporated by reference in its entirety. A damaged or "leaky" barrier can allow antigens to cross the barrier, which in turn elicits an immune response that can cause further damage to gastrointestinal tissue. Such an immune response can include recruitment of neutrophils or T cells, for example. An anti-IL-4R antibody (e.g., an anti-IL-4Rα antibody, e.g., dupilumab) can be administered to inhibit undesirable stimulation of an immune response.

Colitis is a chronic digestive disease characterized by inflammation of the inner lining of the colon. Infection, loss of blood supply in the colon, Inflammatory Bowel Disease (IBD) and invasion of the colon wall with collagen or lymphocytic white blood cells are all possible causes of an inflamed colon In some instances, colitis is viral colitis. In some instances, colitis is bacterial colitis. In some instances, colitis is caused by an allergic reaction. In some instances, colitis is caused by a reaction to food.

Disclosed herein are methods of treating a subject having colitis by administering an anti-IL-4R antibody (e.g., an anti-IL-4Rα antibody, e.g., dupilumab) to the subject. Also disclosed herein are methods of alleviating, ameliorating, or preventing reactions associated with colitis by administering an anti-IL-4R antibody (e.g., an anti-IL-4Rα antibody, e.g., dupilumab) to the patient.

Also disclosed herein are methods of treating a subject having ulcerative colitis which include administering an anti-IL-4R antibody (e.g., an anti-IL-4Rα antibody, e.g., dupilumab). Also disclosed are methods of alleviating, ameliorating, or preventing reactions associated with ulcerative colitis, which include administering an anti-IL-4R antibody (e.g., an anti-IL-4Rα antibody, e.g., dupilumab).

Whipple's Disease

*Tropheryma whippelii* is the causative bacterium for Whipple's Disease, also known as intestinal lipodystrophy and lipophagia granulomatosis. The disease is characterized by steatorrhea, frequently generalized lymphadenopathy, arthritis, fever, and cough. Also reported in Whipple's Disease patients are an abundance of "foamy" macrophages in the jejunal lamina propria, and lymph nodes containing periodic acid-schiff positive particles appearing bacilliform by electron microscopy (Steadman's Medical Dictionary, 26th Edition, Williams & Wilkins, Baltimore, Md., 1995).

The use of an anti-IL-4R antibody (e.g., an anti-IL-4Rα antibody, e.g., dupilumab) can benefit patients having (or at risk for developing) Whipple's Disease, by restoring a normal balance between the TH1 and TH2 components of the patient's immune response. Increased production of IL-4 (a TH2-type cytokine) and decreased levels of certain TH1-type cytokines have been associated with Whipple's Disease. TH2 cytokines can contribute to bacterial persistence, whereas a TH1 response plays a role in clearing the causative bacteria. Ann anti-IL-4Rα antibody (e.g., dupilumab) can be administered to patients infected with *T. whippelii*, whether or not the patient exhibits clinical symptoms of Whipple's Disease.

Disclosed herein are methods of treating a subject having Whipple's Disease which include administering an anti-IL-4R antibody (e.g., an anti-IL-4Rα antibody, e.g., dupilumab). Also disclosed are methods of alleviating, ameliorating, or preventing reactions associated with Whipple's Disease, which include administering an anti-IL-4R antibody (e.g., an anti-IL-4Rα antibody, e.g., dupilumab).

Behçet's Disease

Behçet's disease, or Behçet's syndrome, is a rare disorder that causes blood vessel inflammation. Behçet's disease presents with a variety of signs and symptoms in the digestive system, including abdominal pain, diarrhea and bleeding.

Disclosed herein are methods of treating a subject having Behçet's Disease which include administering an anti-IL-4R antibody (e.g., an anti-IL-4Rα antibody, e.g., dupilumab). Also disclosed are methods of alleviating, ameliorating, or preventing reactions associated with Behçet's Disease, which include administering an anti-IL-4R antibody (e.g., an anti-IL-4Rα antibody, e.g., dupilumab).

Wegener Granulomatosis

Wegener granulomatosis (or Granulomatosis with polyangiitis (GPA)), is a rare multisystem autoimmune disease. Its hallmark features include necrotizing granulomatous inflammation and pauci-immune vasculitis in small- and medium-sized blood vessels.

Disclosed herein are methods of treating a subject having Wegener granulomatosis which include administering an anti-IL-4R antibody (e.g., an anti-IL-4Rα antibody, e.g., dupilumab). Also disclosed are methods of alleviating, ameliorating, or preventing reactions associated with Wegener granulomatosis, which include administering an anti-IL-4R antibody (e.g., an anti-IL-4Rα antibody, e.g., dupilumab).

Gastroesophageal Reflux Disease (GERD)

Gastroesophageal reflux disease (GERD) occurs when stomach acid frequently flows back into the tube connecting the mouth and stomach. This backwash (acid reflux) can irritate the lining of the esophagus. In some instances, GERD includes acid reflux.

Disclosed herein are methods of treating a subject having GERD which include administering an anti-IL-4R antibody (e.g., an anti-IL-4Rα antibody, e.g., dupilumab). Also disclosed are methods of alleviating, ameliorating, or preventing reactions associated with GERD, which include administering an anti-IL-4R antibody (e.g., an anti-IL-4Rα antibody, e.g., dupilumab).

Eosinophilic Colitis

Eosinophilic colitis (EC) is a rare form of primary eosinophilic gastrointestinal disease with a bimodal peak of prevalence in neonates and young adults. EC remains a little understood condition in contrast to the increasingly recognized eosinophilic esophagitis. Clinical presentation of EC is highly variable according to mucosal, transmural, or serosal predominance of inflammation. EC has a broad differential diagnosis because colon tissue eosinophilia often occurs in parasitic infection, drug-induced allergic reactions, inflammatory bowel disease, and various connective tissue disorders, which require thorough searching for secondary causes that may be specifically treated with antibiotics or dietary and drug elimination.

Disclosed herein are methods of treating a subject having EC by administering an anti-IL-4R antibody (e.g., an anti-IL-4Rα antibody, e.g., dupilumab) to the subject. Also disclosed herein are methods of alleviating, ameliorating, or preventing reactions associated with EC by administering an anti-IL-4R antibody (e.g., an anti-IL-4Rα antibody, e.g., dupilumab) to the patient.

Interstitial Cystitis

Interstitial cystitis is a chronic condition causing bladder pressure, bladder pain and sometimes pelvic pain. The pain ranges from mild discomfort to severe pain. The condition is a part of a spectrum of diseases known as painful bladder syndrome. Symptoms of interstitial cystitis vary from person to person and include one or more of pelvic pain; a persistent, urgent need to urinate; frequent urination; and pain during sexual intercourse.

Disclosed herein are methods of treating a subject having interstitial cystitis by administering an anti-IL-4R antibody (e.g., an anti-IL-4Rα antibody, e.g., dupilumab) to the subject. Also disclosed herein are methods of alleviating, ameliorating, or preventing reactions associated with interstitial cystitis by administering an anti-IL-4R antibody (e.g., an anti-IL-4Rα antibody, e.g., dupilumab) to the patient.

Gastroenteritis

Gastroenteritis, also known as infectious diarrhea, is inflammation of the gastrointestinal tract, including the stomach and small intestine. Symptoms may include diarrhea, vomiting and abdominal pain. In some instances, fever, lack of energy and dehydration occur. In some instances, gastroenteritis is viral gastroenteritis. In some instances, gastroenteritis is bacterial gastroenteritis. In some instances, gastroenteritis is caused by an allergic reaction. In some instances, gastroenteritis is caused by a reaction to food.

Disclosed herein are methods of treating a subject having gastroenteritis by administering an anti-IL-4R antibody (e.g., an anti-IL-4Rα antibody, e.g., dupilumab) to the subject. Also disclosed herein are methods of alleviating, ameliorating, or preventing reactions associated with gastroenteritis by administering an anti-IL-4R antibody (e.g., an anti-IL-4Rα antibody, e.g., dupilumab) to the patient.

Kidney-Related Indications

In some instances, disclosed are methods of treating gastrointestinal-related indications, including nephrosis, glomerulonephritis, or Goodpasture syndrome.

Nephrosis

Nephrosis, also known as nephrotic syndrome, is kidney disease that is non-inflammatory and non-malignant. In the condition known as minimal change nephrosis, glomerular damage (believed to arise from structural changes in glomerular visceral epithelial cells) results in abnormalities that include proteinuria. A TH2-type immune response (especially secretion of the TH2-type cytokines IL-4 and IL-13) are implicated as playing a role in pathogenesis of minimal changes in nephrosis.

Disclosed herein are methods of treating a subject having nephrosis which include administering an anti-IL-4R antibody (e.g., an anti-IL-4Rα antibody, e.g., dupilumab). Also disclosed are methods of alleviating, ameliorating, or preventing reactions associated with nephrosis, which include administering an anti-IL-4R antibody (e.g., an anti-IL-4Rα antibody, e.g., dupilumab).

Glomerulonephritis

Glomerulonephritis is inflammation of the tiny filters, the glomeruli, in a kidney. Symptoms associated with glomerulonephritis include one or more of pink or cola-colored urine from red blood cells in urine, foamy urine due to excess protein (i.e., proteinuria), high blood pressure (hypertension), and fluid retention (edema) with swelling evident in the face, hands, feet, and/or abdomen.

In some instances, glomerulonephritis occurs without another indication. In some instances, glomerulonephritis presents with another indication. In some instances, glomerulonephritis presents with lupus. In some instances, glomerulonephritis presents with diabetes. In some aspects, glomerulonephritis is acute. In some instances, glomerulonephritis is chronic.

Disclosed herein are methods of treating a subject having glomerulonephritis which include administering an anti-IL-4R antibody (e.g., an anti-IL-4Rα antibody, e.g., dupilumab). Also disclosed are methods of alleviating, ameliorating, or preventing reactions associated with glomerulonephritis, which include administering an anti-IL-4R antibody (e.g., an anti-IL-4Rα antibody, e.g., dupilumab).

Goodpasture Syndrome

Goodpasture syndrome is a rare but serious autoimmune disease that affects the lungs and kidneys. The disease occurs when the body's immune system mistakenly produces antibodies against collagen in the lungs and kidneys. In some instances, a subject having Goodpasture syndrome presents with fatigue.

Disclosed herein are methods of treating a subject having Goodpasture syndrome which include administering an anti-IL-4R antibody (e.g., an anti-IL-4Rα antibody, e.g., dupilumab). Also disclosed are methods of alleviating, ameliorating, or preventing reactions associated with Goodpasture syndrome, which include administering an anti-IL-4R antibody (e.g., an anti-IL-4Rα antibody, e.g., dupilumab).

Chronic Tubulo-Interstitial Nephritis

Disclosed herein are subjects having chronic tubulo-interstitial nephritis. Chronic tubulo-interstitial nephritis is a frequent cause of acute kidney injury that can lead to chronic kidney disease (CKD). Chronic tubulo-Interstitial nephritis is associated with an immune-mediated infiltration of the kidney interstitium by inflammatory cells, which may progress to fibrosis. In some instances, subject present with non-specific symptoms. Etiology of tubulo-interstitial nephritis can be drug-induced, infectious, idiopathic, genetic, or related to a systemic inflammatory condition such as tubulo-interstitial nephritis and uveitis (TINU) syndrome, inflammatory bowel disease, or IgG4-associated immune complex multiorgan autoimmune disease (MAD).

Disclosed herein are methods of treating a subject having chronic tubulo-interstitial nephritis by administering an anti-IL-4R antibody (e.g., an anti-IL-4Rα antibody, e.g., dupilumab) to the subject. Also disclosed herein are methods of alleviating, ameliorating, or preventing reactions associated with chronic tubulo-interstitial nephritis by administering an anti-IL-4R antibody (e.g., an anti-IL-4Rα antibody, e.g., dupilumab) to the patient.

Hematuria

Disclosed herein are subjects having hematuria. Hematuria is the presence of blood in a subject's urine. In some instances, the hematuria is recurrent and persistent hematuria with other morphologic changes.

Disclosed herein are methods of treating a subject having hematuria by administering an anti-IL-4R antibody (e.g., an anti-IL-4Rα antibody, e.g., dupilumab) to the subject. Also disclosed herein are methods of alleviating, ameliorating, or preventing reactions associated with hematuria by administering an anti-IL-4R antibody (e.g., an anti-IL-4Rα antibody, e.g., dupilumab) to the patient.

Disclosed herein are methods of treating a subject having recurrent and persistent hematuria with other morphologic changes by administering an anti-IL-4R antibody (e.g., an anti-IL-4Rα antibody, e.g., dupilumab) to the subject. Also disclosed herein are methods of alleviating, ameliorating, or preventing reactions associated with recurrent and persistent hematuria with other morphologic changes by administering an anti-IL-4R antibody (e.g., an anti-IL-4Rα antibody, e.g., dupilumab) to the patient.

Prostate-Related Indications

In some instances, disclosed are methods of treating prostate-related indications, including benign prostate hyperplasia (BPH) or chronic prostatitis syndrome.

Benign Prostate Hyperplasia

Benign prostate hyperplasia (BPH), also known as benign prostate hypertrophy, can be treated with an anti-IL-4R antibody (e.g., an anti-IL-4Rα antibody, e.g., dupilumab). While not wishing to be bound by a particular mechanism of action, administration of an IL-4 inhibitor can benefit a patient with BPH by suppressing IL-4-induced inflammation, or by suppressing a TH2-type immune response.

Disclosed herein are methods of treating a subject having BPH which include administering an anti-IL-4R antibody (e.g., an anti-IL-4Rα antibody, e.g., dupilumab). Also disclosed are methods of alleviating, ameliorating, or preventing reactions associated with BPH, which include administering an anti-IL-4R antibody (e.g., an anti-IL-4Rα antibody, e.g., dupilumab).

Chronic Prostatitis Syndrome

Chronic prostatitis syndrome is an inflammation of the prostate gland. In some instances, chronic prostatitis syndrome presents with constant urge to urinate, burning pain when urinating, difficulty with urination, and pain. In some instances, chronic prostatitis syndrome is caused by a bacterial infection (e.g., chronic bacterial prostatitis).

Disclosed herein are methods of treating a subject having chronic prostatitis syndrome which include administering an anti-IL-4R antibody (e.g., an anti-IL-4Rα antibody, e.g., dupilumab). Also disclosed are methods of alleviating, ameliorating, or preventing reactions associated with chronic prostatitis syndrome, which include administering an anti-IL-4R antibody (e.g., an anti-IL-4Rα antibody, e.g., dupilumab).

Thyroid-Related Indications

In some instances, disclosed are methods of treating thyroid-related indications, including Grave's Disease and Hashimoto's Disease.

Grave's Disease

Antibodies directed against thyrotropin receptor play an important role in Grave's Disease (also called thyrotoxicosis with diffuse goiter), a disorder characterized by hyperthyroidism. Studies of cytokine production in Grave's Disease patients show a shift toward a TH2-type cytokine response. Use of an anti-IL-4R antibody (e.g., an anti-IL-4Rα antibody, e.g., dupilumab) to suppress the TH2-type immune response, and suppress antibody production, would benefit Grave's Disease patients.

Disclosed herein are methods of treating a subject having Grave's Disease which include administering an anti-IL-4R antibody (e.g., an anti-IL-4Rα antibody, e.g., dupilumab). Also disclosed are methods of alleviating, ameliorating, or preventing reactions associated with Grave's Disease, which include administering an anti-IL-4R antibody (e.g., an anti-IL-4Rα antibody, e.g., dupilumab).

Kawasaki Disease

Also known as the mucocutaneous lymph node syndrome, Kawasaki disease (KD) mainly afflicts young children. The disease is characterized by particular changes in the mucus membranes lining the lips and mouth, and by enlarged, tender lymph glands. Symptoms typically include fever, conjunctivitis, inflammation of the lips and mucous membranes of the mouth, swollen glands in the neck, and a rash covering the hands and feet, leading to hardened, swollen and peeling skin on hands and feet. In children with Kawasaki Disease (KD), inflammation of arteries (vasculitis) can develop. Due to the effect of the disease on the vascular system, KD reportedly is the main cause of acquired heart disease in children.

An anti-IL-4R antibody (e.g., an anti-IL-4Rα antibody, e.g., dupilumab) can be administered to patients with Kawasaki Disease, to reduce the elevated levels of IL-4 in the patient. Excessive IL-4 secretion and a deficiency in TH1-type cytokines contribute to the pathogenesis of the disease.

Disclosed herein are methods of treating a subject having KD which include administering an anti-IL-4R antibody (e.g., an anti-IL-4Rα antibody, e.g., dupilumab). Also disclosed are methods of alleviating, ameliorating, or preventing reactions associated with KD, which include administering an anti-IL-4R antibody (e.g., an anti-IL-4Rα antibody, e.g., dupilumab).

Hashimoto's Disease

Hashimoto's disease (also called Hashimoto's thyroiditis, chronic lymphocytic thyroiditis, or autoimmune thyroiditis) is an autoimmune disorder that can cause hypothyroidism, or underactive thyroid. With this disease, the immune system attacks the thyroid, which becomes damaged and cannot make enough thyroid hormones. In some instances, a subject having Hashimoto's disease also has elevate cholesterol compared to someone without Hashimoto's disease. In some instances, a subject having Hashimoto's disease has one or more of fatigue, weight gain, trouble tolerating cold, joint and muscle pain, constipation, dry and/or thinning hair, heavy or irregular menstrual periods and problems becoming pregnant, depression, memory problems, and a slowed heart rate.

Disclosed herein are methods of treating a subject having Hashimoto's Disease which include administering an anti-IL-4R antibody (e.g., an anti-IL-4Rα antibody, e.g., dupilumab). Also disclosed are methods of alleviating, ameliorating, or preventing reactions associated with Hashimoto's Disease, which include administering an anti-IL-4R antibody (e.g., an anti-IL-4Rα antibody, e.g., dupilumab).

Blood-Vessel-Related Indications

In some instances, disclosed are methods of treating gastrointestinal-related indications, including vasculitis, polyarteritis nodosa, lupus, or antiphospholipid antibody syndrome (APS).

Vasculitis

Vasculitis is an inflammation of the blood vessels. It causes changes in the blood vessel walls, including thickening, weakening, narrowing or scarring. These changes can restrict blood flow, resulting in organ and tissue damage. In some instances, a subject having vasculitis can present with one or more of fever, headache, fatigue, weight loss, general aches and pains, night sweats, rash and nerve problems, such as numbness or weakness.

Disclosed herein are methods of treating a subject having vasculitis which include administering an anti-IL-4R antibody (e.g., an anti-IL-4Rα antibody, e.g., dupilumab). Also disclosed are methods of alleviating, ameliorating, or preventing reactions associated with vasculitis, which include administering an anti-IL-4R antibody (e.g., an anti-IL-4Rα antibody, e.g., dupilumab).

Polyarteritis Nodosa

Polyarteritis nodosa (PAN) a blood vessel disease characterized by inflammation of small and medium-sized arteries (vasculitis), preventing them from bringing oxygen and food to organs. In some instances, a case of PAN occur in the 4th or 5th decade, although it can occur at any age. Men are about twice as likely to be affected as women. In some instances, a subject with PAN has an active hepatitis B infection.

Disclosed herein are methods of treating a subject having polyarteritis nodosa which include administering an anti-IL-4R antibody (e.g., an anti-IL-4Rα antibody, e.g., dupilumab). Also disclosed are methods of alleviating, ameliorating, or preventing reactions associated with polyarteritis nodosa, which include administering an anti-IL-4R antibody (e.g., an anti-IL-4Rα antibody, e.g., dupilumab).

Neurological-Related Indications

Multiple Sclerosis

Multiple sclerosis (MS) is a chronic neurological disorder defined by recurrent episodes of central nervous system (CNS) demyelination, ultimately culminating in physical and cognitive disability. While it is rare in the pediatric population, MS in children is likely to have a profound impact on their lifetime academic, social, and vocational achievements. MS is the leading cause of neurological disability in young adults in the western hemisphere. MS is considered to be an autoimmune disease of the CNS, in which the immune system repeatedly attacks the CNS, damaging both the myelin and axons. Since the site and severity of repeated immune attacks are different across individuals, the physical or cognitive disability caused is unpredictable and varies widely.

Disclosed herein are methods of treating a subject having MS by administering an anti-IL-4R antibody (e.g., an anti-IL-4Rα antibody, e.g., dupilumab) to the subject. Also disclosed herein are methods of alleviating, ameliorating, or preventing reactions associated with MS by administering an anti-IL-4R antibody (e.g., an anti-IL-4Rα antibody, e.g., dupilumab) to the patient.

Vogt-Koyanagi-Harada (VKH) Syndrome

Disclosed herein are methods of treating a subject having Vogt-Koyanagi-Harada (VKH) syndrome (or disease). VKH is a rare disorder generally of unknown origin that affects many body systems, including as the eyes, ears, skin, and the meninges. The most noticeable symptom is a rapid loss of vision. There may also be neurological signs such as severe headache, vertigo, nausea, and drowsiness. Additional symptoms of VKH include loss of hearing, alopecia, and aberrant skin color, and loss of pigmentation of the hair and eyelashes. In some instances, onset occurs at around 30 or 40 years of age.

Disclosed herein are methods of treating a subject having VKH by administering an anti-IL-4R antibody (e.g., an anti-IL-4Rα antibody, e.g., dupilumab) to the subject. Also disclosed herein are methods of alleviating, ameliorating, or preventing reactions associated with VKH by administering an anti-IL-4R antibody (e.g., an anti-IL-4Rα antibody, e.g., dupilumab) to the patient.

Amyotrophic Lateral Sclerosis (ALS)

Disclosed herein are methods of treating a subject having amyotrophic lateral sclerosis (ALS). ALS, also known as motor neuron disease (MND) or Lou Gehrig's disease, is a progressive disease that causes the death of neurons controlling voluntary muscles. ALS often begins with muscle twitching and weakness in a limb, or slurred speech. Eventually, ALS affects control of the muscles needed to move, speak, eat and breathe. In some instances, a subject having ALS presents with one or more symptoms that include difficulty walking or doing normal daily activities; tripping and falling; weakness in the leg, feet or ankles; hand weakness or clumsiness; slurred speech or trouble swallowing; muscle cramps and twitching in the arms, shoulders and tongue; inappropriate crying, laughing or yawning; or cognitive and behavioral changes.

Disclosed herein are methods of treating a subject having ALS by administering an anti-IL-4R antibody (e.g., an anti-IL-4Rα antibody, e.g., dupilumab) to the subject. Also disclosed herein are methods of alleviating, ameliorating, or preventing reactions associated with ALS by administering an anti-IL-4R antibody (e.g., an anti-IL-4Rα antibody, e.g., dupilumab) to the patient.

Neuromyelitis Optica (NMO)

Disclosed herein are methods of treating a subject having Neuromyelitis optica (NMO) (also called neuromyelitis optica spectrum disorder or Devic's disease). NMO is an autoimmune disorder in which white blood cells and antibodies primarily attack the optic nerves and the spinal cord. In some instances, white blood cells and antibodies attack the brain. In some instances, the damage to the optic nerves produces swelling and inflammation that cause pain and loss of vision. In some instances, the damage to the spinal cord causes weakness or paralysis in the legs or arms, loss of sensation, and problems with bladder and bowel function.

Disclosed herein are methods of treating a subject having NMO by administering an anti-IL-4R antibody (e.g., an anti-IL-4Rα antibody, e.g., dupilumab) to the subject. Also disclosed herein are methods of alleviating, ameliorating, or preventing reactions associated with NMO by administering an anti-IL-4R antibody (e.g., an anti-IL-4Rα antibody, e.g., dupilumab) to the patient.

Gynecology-Related Indications

In some instances, disclosed are methods of treating gynecology-related indications, including pre-eclampsia, antiphospholipid syndrome, or immune thrombocytopenia.

Pre-Eclampsia

Pre-eclampsia is a toxemia of late pregnancy. The condition is characterized by a sharp rise in blood pressure, generally accompanied by edema and albuminuria, during the third term of pregnancy.

Elevated TH1-type and TH2-type immune responses can play a role in the condition. One method provided herein includes administering an anti-IL-4R antibody (e.g., an anti-IL-4Rα antibody, e.g., dupilumab) to a pregnant woman who has developed pre-eclampsia. An anti-IL-4R antibody (e.g., an anti-IL-4Rα antibody, e.g., dupilumab) is administered in an amount, and for a period of time, sufficient to reduce the level of IL-4 (or of TH2-type cytokines collectively) to a level that is considered normal during pregnancy. In some aspects, an anti-IL-4R antibody (e.g., an anti-IL-4Rα antibody, e.g., dupilumab) is administered repeatedly throughout the duration of the pregnancy.

Disclosed herein are methods of treating a subject having pre-eclampsia which include administering an anti-IL-4R antibody (e.g., an anti-IL-4Rα antibody, e.g., dupilumab). Also disclosed are methods of alleviating, ameliorating, or preventing reactions associated with pre-eclampsia, which include administering an anti-IL-4R antibody (e.g., an anti-IL-4Rα antibody, e.g., dupilumab).

Antiphospholipid Syndrome

Antiphospholipid Syndrome occurs when the immune system mistakenly creates antibodies that make blood much more likely to clot. In some instances, a subject having Antiphospholipid Syndrome has repeat miscarriages or still-births. In some instances, Antiphospholipid Syndrome presents with one or more of blood clots, miscarriage, rash, chronic headaches, dementia, and seizures.

Disclosed herein are methods of treating a subject having Antiphospholipid Syndrome which include administering an anti-IL-4R antibody (e.g., an anti-IL-4Rα antibody, e.g., dupilumab). Also disclosed are methods of alleviating, ameliorating, or preventing reactions associated with Antiphospholipid Syndrome, which include administering an anti-IL-4R antibody (e.g., an anti-IL-4Rα antibody, e.g., dupilumab).

Immune Thrombocytopenia

Immune thrombocytopenia is a disorder characterized by a blood abnormality called thrombocytopenia, which is a shortage of blood cell fragments called platelets that are needed for normal blood clotting. In some instances, affected individuals can develop red or purple spots on the skin caused by bleeding just under the skin's surface. Small spots of bleeding under the skin are called purpura and larger spots are called ecchymosis.

Disclosed herein are methods of treating a subject having immune thrombocytopenia which include administering an anti-IL-4R antibody (e.g., an anti-IL-4Rα antibody, e.g., dupilumab). Also disclosed are methods of alleviating, ameliorating, or preventing reactions associated with immune thrombocytopenia, which include administering an anti-IL-4R antibody (e.g., an anti-IL-4Rα antibody, e.g., dupilumab).

Endometriosis

In some instances, a subject as disclosed herein has endometriosis. Endometriosis is a disorder in which tissue similar to the tissue that normally lines the inside of a uterus grows outside a uterus. Endometriosis is a common gynecological condition affecting an estimated 2 to 10 percent of American women of childbearing age. Symptoms of endometriosis may include: excessive menstrual cramps, abnormal or heavy menstrual flow and pain during intercourse.

Disclosed herein are methods of treating a subject having endometriosis by administering an anti-IL-4R antibody (e.g., an anti-IL-4Rα antibody, e.g., dupilumab) to the subject. Also disclosed herein are methods of alleviating, ameliorating, or preventing reactions associated with endometriosis by administering an anti-IL-4R antibody (e.g., an anti-IL-4Rα antibody, e.g., dupilumab) to the patient.

Inflammatory Disease of Cervix Uteri

In some instances, a subject as disclosed herein has inflammatory disease of cervix uteri (or cervicitis). Inflammatory disease of cervix uteri includes inflammation of the cervix.

In some instances, a subject having inflammatory disease of cervix uteri has symptoms of bleeding between menstrual periods, pain with intercourse or during a cervical exam, and abnormal vaginal discharge. In some instances, a subject having inflammatory disease of cervix uteri does not experience these signs or symptoms.

Disclosed herein are methods of treating a subject having inflammatory disease of cervix uteri by administering an anti-IL-4R antibody (e.g., an anti-IL-4Rα antibody, e.g., dupilumab) to the subject. Also disclosed herein are methods of alleviating, ameliorating, or preventing reactions associated with inflammatory disease of cervix uteri by administering an anti-IL-4R antibody (e.g., an anti-IL-4Rα antibody, e.g., dupilumab) to the patient.

Salpingitis In some instances, a subject as disclosed herein has salpingitis. Salpingitis is an infection and inflammation in the Fallopian tubes. In some instances, salpingitis results from sexually transmitted infections (STIs) that involve bacteria, such as chlamydia or gonorrhea. In some instances, a subject having salpingitis has one or more symptoms of foul-smelling vaginal discharge; yellow vaginal discharge; pain during ovulation, menstruation, or intercourse; spotting between periods; dull lower back pain; abdominal pain; nausea; vomiting; fever; or frequent urination.

Disclosed herein are methods of treating a subject having salpingitis by administering an anti-IL-4R antibody (e.g., an anti-IL-4Rα antibody, e.g., dupilumab) to the subject. Also disclosed herein are methods of alleviating, ameliorating, or preventing reactions associated with salpingitis by administering an anti-IL-4R antibody (e.g., an anti-IL-4Rα antibody, e.g., dupilumab) to the patient.

Oophoritis

In some instances, a subject as disclosed herein has oophoritis. In some instances, oophoritis is caused by a bacterial infection. In some instances, a subject having oophoritis presents with one or more of cysts, inflammation, and enlargement in one or both ovaries. In some instances, a subject having salpingitis has one or more symptoms of pain in the lower abdomen and pelvis; increased menstrual bleeding; bleeding between menstrual cycles; pain or bleeding during intercourse; heavy vaginal discharge, which may have a foul odor; burning sensations or pain during urination; or difficulty urinating.

Disclosed herein are methods of treating a subject having oophoritis by administering an anti-IL-4R antibody (e.g., an anti-IL-4Rα antibody, e.g., dupilumab) to the subject. Also disclosed herein are methods of alleviating, ameliorating, or preventing reactions associated with oophoritis by administering an anti-IL-4R antibody (e.g., an anti-IL-4Rα antibody, e.g., dupilumab) to the patient.

Infectious Disease

Acute Lymphadenitis

In some instances, a subject described herein has acute lymphadenitis. Lymphadenitis is an enlargement in one or more lymph nodes, usually due to infection. In some instances, lymphadenitis is acute. In some instances, a lymphadenitis infection caused by bacteria, a virus, or a fungus can spread to one or more lymph nodes. In some instances, acute lymphadenitis is localized (i.e., involves enlargement one or just a few nodes that are close to the area where the infection started). In some instances, acute lymphadenitis is generalized. Generalized acute lymphadenitis occurs in two or more lymph node groups and may be caused by an infection that spreads through the bloodstream or another illness that affects the whole body.

Disclosed herein are methods of treating a subject having acute lymphadenitis by administering an anti-IL-4R antibody (e.g., an anti-IL-4Rα antibody, e.g., dupilumab) to the subject. Also disclosed herein are methods of alleviating, ameliorating, or preventing reactions associated with acute lymphadenitis by administering an anti-IL-4R antibody (e.g., an anti-IL-4Rα antibody, e.g., dupilumab) to the patient.

Cancer

Cutaneous T-Cell Lymphomas

Cutaneous T-cell lymphomas (CTCLs) primarily affect skin and are characterized by proliferation of mature CD4+ T-helper cells. The pattern of cytokine production in the skin and blood is considered to be of major importance for the pathogenesis of CTCLs. Abnormal cytokine expression in CTCLs can be responsible for enhanced proliferation of the malignant cells and/or depression of the antitumor immune response. The most common forms of CTCL, mycosis fungoides (MF) and Sézary syndrome (SS), are characterized by proliferation of mature CD4+T-helper cells. Subjects with MF usually develop cutaneous patches and plaques and have an indolent course with a 5-year survival rate of ~87%. Zackheim et al., *J Am Acad Dermatol.* 1999 March; 40(3): 418-25.

Disclosed herein are methods of treating a subject having CTCLs which include administering an anti-IL-4R antibody (e.g., an anti-IL-4Rα antibody, e.g., dupilumab). Also disclosed are methods of alleviating, ameliorating, or preventing reactions associated with CTCLs, which include administering an anti-IL-4R antibody (e.g., an anti-IL-4Rα antibody, e.g., dupilumab).

Leukemia

Myeloid Leukemia

Myeloid Leukemia is a type of cancer that affects myeloid tissue. In some instances, the bone marrow makes abnormal myeloblasts, red blood cells, or platelets. In some instances myeloid leukemia is acute myeloid leukemia. In some instances, myeloid leukemia is chronic myeloid leukemia. In some instances, symptoms may include feeling tired, shortness of breath, easy bruising and bleeding, and increased risk of infection.

Disclosed herein are methods of treating a subject having myeloid leukemia which include administering an anti-IL-4R antibody (e.g., an anti-IL-4Rα antibody, e.g., dupilumab). Also disclosed are methods of alleviating, ameliorating, or preventing reactions associated with myeloid leukemia, which include administering an anti-IL-4R antibody (e.g., an anti-IL-4Rα antibody, e.g., dupilumab).

Monocytic Leukemia

Monocytic leukemia is a category of myeloid leukemia characterized by a dominance of monocytes in the marrow. When the monocytic cells are predominantly monoblasts, it can be subclassified into acute monoblastic leukemia. Monocytic leukemias may be subdivided into acute monocytic leukemia, acute myelomonocytic leukemia, and subacute and chronic myelomonocytic leukemia. The clinical features of acute monocytic and acute myelomonocytic leukemias are similar and are manifestations of bone marrow failure. In some instances, monocytic leukemia is acute monocytic leukemia (AML). In some instances, monocytic leukemia is chronic monocytic leukemia (CML).

Disclosed herein are methods of treating a subject having monocytic leukemia by administering an anti-IL-4R antibody (e.g., an anti-IL-4Rα antibody, e.g., dupilumab) to the subject. Also disclosed herein are methods of alleviating, ameliorating, or preventing reactions associated with monocytic leukemia by administering an anti-IL-4R antibody (e.g., an anti-IL-4Rα antibody, e.g., dupilumab) to the patient.

Cervical Cancer

Carcinoma In Situ of Cervix Uteri

Carcinoma In Situ Of Cervix Uteri (also called cervical carcinoma in situ) is also referred to as stage 0 cervical cancer. Carcinoma in situ (CIS) is a general term for an early stage cancer. In some instance, Carcinoma In Situ Of Cervix Uteri is noninvasive. In some instances, Carcinoma In Situ Of Cervix Uteri is confined to the surface of the cervix. In some instances, Carcinoma In Situ Of Cervix Uteri is associated with human papillomavirus virus (HPV) infection.

Disclosed herein are methods of treating a subject having Carcinoma In Situ Of Cervix Uteri which include administering an anti-IL-4R antibody (e.g., an anti-IL-4Rα antibody, e.g., dupilumab). Also disclosed are methods of alleviating, ameliorating, or preventing reactions associated with Carcinoma In Situ Of Cervix Uteri, which include administering an anti-IL-4R antibody (e.g., an anti-IL-4Rα antibody, e.g., dupilumab).

Chronic Myeloproliferative Disease

Chronic myeloproliferative disease or disorders are disorders are a group of slow-growing blood cancers in which the bone marrow which accumulate an abnormal number red blood cells, white blood cells, or platelets.

Disclosed herein are methods of treating a subject having a chronic myeloproliferative disease by administering an anti-IL-4R antibody (e.g., an anti-IL-4Rα antibody, e.g., dupilumab) to the subject. Also disclosed herein are methods of alleviating, ameliorating, or preventing reactions associated with a chronic myeloproliferative disease by administering an anti-IL-4R antibody (e.g., an anti-IL-4Rα antibody, e.g., dupilumab) to the patient.

Breast Cancer

Disclosed herein are methods of treating a subject having breast cancer by administering an anti-IL-4R antibody (e.g., an anti-IL-4Rα antibody, e.g., dupilumab) to the subject. Also disclosed herein are methods of alleviating, ameliorating, or preventing reactions associated with breast cancer by administering an anti-IL-4R antibody (e.g., an anti-IL-4Rα antibody, e.g., dupilumab) to the patient.

Malignant Neoplasm of the Breast

In some instances, a subject described herein has malignant breast cancer (e.g., malignant neoplasm of the breast). Malignant breast cancer forms from the uncontrolled growth of abnormal breast cells. Malignant tumors can invade and destroy surrounding tissue and spread to other parts of the body. In some instances, cancerous cells grow in ductal and/or lobular tissues.

Disclosed herein are methods of treating a subject having malignant breast cancer by administering an anti-IL-4R antibody (e.g., an anti-IL-4Rα antibody, e.g., dupilumab) to the subject. Also disclosed herein are methods of alleviating, ameliorating, or preventing reactions associated with malignant breast cancer by administering an anti-IL-4R antibody (e.g., an anti-IL-4Rα antibody, e.g., dupilumab) to the patient.

Carcinoma In Situ of Breast

Carcinoma in situ of breast (e.g., ductal carcinoma in situ (DCIS)) is the presence of abnormal cells inside a milk duct in the breast. DCIS is considered the earliest form of breast cancer. DCIS is noninvasive, meaning it has not spread out of the milk duct and has a low risk of becoming invasive. In some instances, a subject having DCIS has no signs or symptoms. In some instances, a subject has a lump in the breast, some discharge coming out of the nipple, or both.

Disclosed herein are methods of treating a subject having carcinoma in situ of breast by administering an anti-IL-4R antibody (e.g., an anti-IL-4Rα antibody, e.g., dupilumab) to the subject. Also disclosed herein are methods of alleviating, ameliorating, or preventing reactions associated with carcinoma in situ of breast by administering an anti-IL-4R antibody (e.g., an anti-IL-4Rα antibody, e.g., dupilumab) to the patient.

Prostate Cancer

Malignant Neoplasm of the Prostate

In some instances, subject disclosed herein have prostate cancer. In some instances, subjects disclosed herein have malignant prostate cancer. Prostate cancer is cancer that occurs in the prostate, a small walnut-shaped gland in men that produces the seminal fluid that nourishes and transports sperm. Prostate cancer is one of the most common types of cancer in men. In some instances, prostate cancer grows slowly and is initially confined to the prostate gland, where it may not cause serious harm. In some instances, prostate cancer spreads to other organs in a subject.

Disclosed herein are methods of treating a subject having malignant prostate cancer by administering an anti-IL-4R antibody (e.g., an anti-IL-4Rα antibody, e.g., dupilumab) to the subject. Also disclosed herein are methods of alleviating, ameliorating, or preventing reactions associated with malignant prostate cancer by administering an anti-IL-4R antibody (e.g., an anti-IL-4Rα antibody, e.g., dupilumab) to the patient.

Enhancing Efficacy of a Vaccine

Vaccines typically contain the causative agent of a disease, its products or its substitute which acts as an antigen without causing the disease (or causing mild disease, in some cases). Some current vaccines against, e.g., microbial pathogens, consist of live attenuated or non-virulent variant strains of microorganisms, or killed or otherwise inactivated organisms. Other vaccines utilize more or less purified components of pathogen lysates such as surface carbohydrates, recombinant pathogen-derived proteins that are sometimes fused to other molecules, or replicative viruses that produce an antigen from a pathogen. Vaccines work by inducing an endogenous immune response resulting in the activation of antigen-specific naive lymphocytes that then give rise to antibody-secreting B cells or antigen-specific effector and memory T cells or both. This approach can result in long-lived protective immunity that can be boosted from time to time by renewed exposure to the same antigenic material.

Vaccines commonly contain adjuvants that help to accelerate, prolong and/or enhance antigen-specific immune responses. Some commonly used adjuvants include, but are not limited to, aluminum salts (e.g., alum, aluminum phosphate, and aluminum hydroxide), Freund's complete adjuvant, Freund's incomplete adjuvant, Ribi's adjuvant, squalene, and MF59®.

In some aspects, the disclosure provides methods for enhancing the efficacy and/or safety of a vaccine in a subject. Also included are methods for increasing the immune response against a vaccine or for increasing the duration of protective immunity of a vaccine in a subject. In certain embodiments, the present disclosure provides methods for increasing protection against a disease in a subject and/or for preventing infection and transmission of said disease to an uninfected subject or for preventing progression of the disease to another disease. The methods, according to these aspects, include administering to a subject in need thereof an anti-IL-4R antibody (e.g., an anti-IL-4Rα antibody, e.g., dupilumab) in combination with a vaccine. In certain embodiments, the methods include selecting a subject that is susceptible to a microbial infection and administering to the subject in need thereof an anti-IL-4R antibody (e.g., an anti-IL-4Rα antibody, e.g., dupilumab) in combination with a vaccine against said microbial infection. In certain embodiments, an anti-IL-4R antibody (e.g., an anti-IL-4Rα antibody, e.g., dupilumab) is administered before, after or concurrent with a vaccine in a subject in need thereof. Methods of delivering vaccines is disclosed further in U.S. Pat. No. 10,314,904 B2, which is incorporated by reference in its entirety.

Disclosed herein are methods for preventing, treating, reducing, or ameliorating an adverse side effect (e.g., an allergic reaction) of a vaccine in a subject in need thereof. In certain embodiments, the present disclosure provides methods for preventing, reducing, or ameliorating T helper 2 (Th2) response elicited by a vaccine in a subject in need thereof. In certain embodiments, the present disclosure provides methods for reducing IgE induced by a vaccine in a subject in need thereof. The methods, according to these aspects, include administering an anti-IL-4R antibody (e.g., an anti-IL-4Rα antibody, e.g., dupilumab) in combination with a vaccine to a subject in need thereof.

Disclosed herein are methods of to reduce the number of vaccine doses, the methods including administering an anti- IL-4R antibody (e.g., an anti-IL-4Rα antibody, e.g., dupilumab) in combination with said vaccine to a subject in need thereof. In certain embodiments, the number of vaccine doses is reduced by one or more doses, e.g., by one dose, by two doses, or more as compared to a subject not administered an anti-IL-4R antibody (e.g., an anti-IL-4Rα antibody, e.g., dupilumab).

Other Indications

Allergy

Allergies and allergic diseases are serious medical conditions with consequences ranging from non-life threatening responses that resolve over time to life threatening effects such as anaphylaxis. Allergic reactions can result from contact or exposure to a variety of products such as certain food items, insect venom, plant-derived material (e.g., pollen), chemicals, drugs/medications, and animal dander.

As used herein, the phrases "allergic response," "allergic reaction," "allergic symptom," and the like, include one or more signs or symptoms selected from urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and/or organ dysfunction/failure. An "allergic response," "allergic reaction," "allergic symptom," etc., also includes immunological responses and reactions such as, e.g., increased IgE production and/or increased allergen-specific immunoglobulin production. In some instances, methods are provided for treating, preventing, or reducing the severity of an allergic response, an allergic reaction, an allergic symptom, or a combination thereof by administering an anti-IL-4R antibody (e.g., an anti-IL-4Rα antibody, e.g., dupilumab) to a subject.

In some instances, methods are provided for treating, preventing, or reducing the severity of an allergic reaction in a subject. The methods include administering a therapeutically effective amount of a pharmaceutical composition including an anti-IL-4R antibody (e.g., an anti-IL-4Rα antibody, e.g., dupilumab) to a subject in need thereof. The pharmaceutical composition including an anti-IL-4R antibody (e.g., an anti-IL-4Rα antibody, e.g., dupilumab) can be administered to the subject either before, during or after allergen exposure or manifestation of an allergic symptom.

In some instances, methods are provided for treating, preventing, or reducing the severity of an allergic reaction in a subject after the subject is identified as a candidate for therapy using the computational methods disclosed herein. The methods include administering a therapeutically effective amount of a pharmaceutical composition including an anti-IL-4R antibody (e.g., an anti-IL-4Rα antibody, e.g., dupilumab) to a subject in need thereof. The pharmaceutical composition including an anti-IL-4R antibody (e.g., an anti-IL-4Rα antibody, e.g., dupilumab) can be administered to the subject either before, during or after allergen exposure or manifestation of an allergic symptom.

Also included are methods for reducing total serum IgE levels in a subject who has been exposed to an allergen. The term "allergen," as used herein, includes any substance, chemical, particle or composition capable of stimulating an allergic response in a susceptible individual. Allergens can be contained within or derived from a food item such as, e.g., dairy products (e.g., cow's milk), egg, celery, sesame, wheat, soy, fish, shellfish, sugars (e.g., sugars present on meat such as alpha-galactose), peanuts, other legumes (e.g., beans, peas, soybeans, etc.), and tree nuts. An allergen can be contained within or derived from a non-food item such as, e.g., dust (e.g., containing dust mite), pollen, insect venom (e.g., venom of bees, wasps, mosquitos, fire ants, etc.), mold, animal fur, animal dander, wool, latex, metals (e.g., nickel), household cleaners, detergents, medication, cosmetics (e.g., perfumes, etc.), drugs (e.g., penicillin, sulfonamides, salicylate, etc.), therapeutic monoclonal antibodies (e.g., cetuximab), ragweed, grass and birch. Exemplary pollen allergens include, e.g., tree pollens such as birch pollen, cedar pollen, oak pollen, alder pollen, hornbeam pollen, aesculus pollen, willow pollen, poplar pollen, plantanus pollen, tilia pollen, olea pollen, Ashe juniper pollen, and Alstonia scholaris pollen.

The present disclosure also includes methods for treating, preventing, or reducing the severity of an allergic reaction triggered by any of the aforementioned allergens or classes of allergens. For example, the allergic reaction can be triggered by consumption or exposure to a food item (e.g., milk, egg, wheat, soy, fish, shellfish, peanut or tree nut). As another example, the allergic reaction can be triggered by a non-food allergen (e.g., insect venom, dust, mold, animal dander, pollen, latex, medication, ragweed, grass, or birch).

Allergy and allergen-specific indications are further disclosed in U.S. Pat. No. 10,392,439 B2 and WO-2018/045130 A2, both of which are incorporated by reference in their entirety.

Angioneurotic Edema, Initial Encounter

Angioneurotic edema is a rare disease that includes relapsing subcutaneous or submucosal edema caused by a deficiency in C1Inh (inhibitor of the C1 fraction of complement). In some instances, disclosed herein are methods to treat a subject having an initial encounter of angioneurotic edema. Angioedema is an area of swelling or urticaria of the deep dermis, subcutaneous, or submucosal tissue due to vascular leakage. ACE inhibitors are the main etiology, followed by the hereditary forms and the acquired forms. Quantitative and qualitative measurements of C1 inhibitors are important to differentiate the common form of HAE from the variant form.

Disclosed herein are methods of treating a subject having angioneurotic edema, initial encounter by administering an anti-IL-4R antibody (e.g., an anti-IL-4Rα antibody, e.g., dupilumab) to the subject. Also disclosed herein are methods of alleviating, ameliorating, or preventing reactions associated with angioneurotic edema, initial encounter by administering an anti-IL-4R antibody (e.g., an anti-IL-4Rα antibody, e.g., dupilumab) to the patient.

Anaphylaxis

Anaphylaxis is a severe, whole-body allergic reaction to a chemical that has become an allergen. In some instances, it can occur within seconds or minutes of exposure an allergen, such as peanuts or a bee sting. Symptoms associated with anaphylaxis include, but are not limited to, skin reactions, including hives and itching and flushed or pale skin; low blood pressure; constriction of the airways and a swollen tongue or throat, which can cause wheezing and trouble breathing; a weak and rapid pulse; nausea; vomiting; diarrhea; and/or dizziness or fainting.

Disclosed herein are methods of treating a subject having anaphylaxis which include administering an anti-IL-4R antibody (e.g., an anti-IL-4Rα antibody, e.g., dupilumab). Also disclosed are methods of alleviating, ameliorating, or preventing reactions associated with anaphylaxis, which include administering an anti-IL-4R antibody (e.g., an anti-IL-4Rα antibody, e.g., dupilumab).

Arthritis (Including Septic Arthritis)

An anti-IL-4R antibody (e.g., an anti-IL-4Rα antibody, e.g., dupilumab) can be used to treat septic arthritis, which also is known as reactive arthritis or bacterial arthritis.

Septic arthritis can be triggered by (result from, or develop subsequent to) infection with such microbes as *Staphylococcus aureus, Chlamydia trachomatis, Yersinia* e.g., *Y. enterocolitica, Salmonella*, e.g., *S. enteritidis, Shigella* and *Campylobacter. S. aureus* has been reported to be the major human pathogen in septic arthritis, responsible for the majority of cases.

IL-4 and IL-4-dependent Th2 responses play roles in promoting septic arthritis. An anti-IL-4R antibody (e.g., an anti-IL-4Rα antibody, e.g., dupilumab) is employed in accordance with the disclosure, to inhibit IL-4 and also to suppress the Th2 response in patients having septic arthritis or at risk for developing septic arthritis.

IL-4 increases bacterial burden and bacterial persistence in joints, by inhibiting clearance of the bacteria. An anti-IL-4R antibody (e.g., an anti-IL-4Rα antibody, e.g., dupilumab) can be employed to assist in the clearance of bacteria associated with reactive arthritis, thereby reducing clinical manifestations such as swelling in joints. An anti-IL-4R antibody (e.g., an anti-IL-4Rα antibody, e.g., dupilumab) can be administered to a human patient afflicted with septic arthritis, to reduce IL-4-mediated joint inflammation. In one approach, an anti-IL-4R antibody (e.g., an anti-IL-4Rα antibody, e.g., dupilumab) is injected into a joint, e.g., into synovial fluid in the knee.

Administering an anti-IL-4R antibody (e.g., an anti-IL-4Rα antibody, e.g., dupilumab) can benefit patients having (or at risk for) septic arthritis by suppressing a TH2 response and promoting a TH1 response against the infection. TH2 cytokines can contribute to bacterial persistence in the joint, whereas a TH1 response plays a role in eliminating the bacteria.

An anti-IL-4R antibody (e.g., an anti-IL-4Rα antibody, e.g., dupilumab) can be administered to patients infected with bacteria or other microbes such as those listed above, to prevent development of septic arthritis. An anti-IL-4R antibody (e.g., an anti-IL-4Rα antibody, e.g., dupilumab) can be administered after diagnosis with such an infection, but before development of clinical symptoms of septic arthritis.

After a subject is identified as a candidate for therapy using the computational methods disclosed herein, an anti-IL-4R antibody (e.g., an anti-IL-4Rα antibody, e.g., dupilumab) can be administered to patients infected with bacteria or other microbes such as those listed above, to prevent development of septic arthritis. An anti-IL-4R antibody (e.g., an anti-IL-4Rα antibody, e.g., dupilumab) can be administered after diagnosis with such an infection, but before development of clinical symptoms of septic arthritis.

Postinfective and Reactive Arthropathies

An arthropathy is a disease of a joint and in some instances, it includes inflammation. Among general causes of an arthropathy are traumatic (sprain, dislocation, fracture etc.), intra- or postinfectious causes (septic arthritis, osteomyelitis, viral arthritis, poststreptococcal arthritis etc.), inflammatory/immunological causes (transient synovitis, reactive arthritis, etc.), tumors (bone tumors, metastases, etc.), degenerative diseases (Legg Calve Perthes disease, osteochondritis dissecans etc.).

Postinfective arthropathies (or postinfectious arthropathies) occur when a joint is infected and include, for example, septic arthritis, osteomyelitis, viral arthritis, and poststreptococcal arthritis. Disclosed herein are methods of treating a subject having postinfective arthropathies which include administering an anti-IL-4R antibody (e.g., an anti-IL-4Rα antibody, e.g., dupilumab). Also disclosed are methods of alleviating, ameliorating, or preventing reactions associated with postinfective arthropathies, which include administering an anti-IL-4R antibody (e.g., an anti-IL-4Rα antibody, e.g., dupilumab).

Reactive arthropathies includes the development of sterile inflammatory arthritis as a sequel to remote infection, often in the gastrointestinal or urogenital tract. The diagnosis is mainly clinical, and based on acute oligoarticular arthritis of larger joints developing within 2-4 weeks of the preceding infection. Disclosed herein are methods of treating a subject having reactive arthropathies which include administering an anti-IL-4R antibody (e.g., an anti-IL-4Rα antibody, e.g., dupilumab). Also disclosed are methods of alleviating, ameliorating, or preventing reactions associated with reactive arthropathies, which include administering an anti-IL-4R antibody (e.g., an anti-IL-4Rα antibody, e.g., dupilumab).

Asthma

Asthma is a chronic inflammatory disease of the airways characterized by airway hyper responsiveness, acute and chronic bronchoconstriction, airway edema, and mucus plugging. An anti-IL-4R antibody (e.g., an anti-IL-4Rα antibody, e.g., dupilumab) can be used to treat asthma by improving "asthma-associated parameters."

The disclosure includes methods for improving one or more asthma-associated parameters in a subject in need thereof, wherein the methods include administering a pharmaceutical composition including an anti-IL-4R antibody (e.g., an anti-IL-4Rα antibody, e.g., dupilumab) to the subject. Examples of "asthma-associated parameters" include: (a) forced expiratory volume in 1 second (FEV1); (b) peak expiratory flow rate (PEF), including morning PEF (AM PEF) and evening PEF (PM PEF); (c) use of an inhaled bronchodilator such as albuterol or levalbuterol; (d) five-item Asthma Control Questionnaire (ACQ5) score; (d) nighttime awakenings; and (e) 22-item Sino-Nasal Outcome Test (SNOT-22) score. An "improvement in an asthma-associated parameter" means an increase from baseline of one or more of FEV1, AM PEF or PM PEF, and/or a decrease from baseline of one or more of daily albuterol/levalbuterol use, ACQ5 score, average nighttime awakenings or SNOT-22 score. As used herein, the term "baseline," with regard to an asthma-associated parameter, means the numerical value of the asthma-associated parameter for a patient prior to or at the time of administration of a pharmaceutical composition of the present disclosure. Methods for treating asthma is disclosed further in U.S. Pat. No. 9,574,004 B2; U.S. Pat. No. 10,137,193 B2; and WO 2019/089473 A1, each of which is incorporated by reference in its entirety.

As used herein, the term "asthma" can be used interchangeably with "intermittent asthma." "Asthma" and "intermittent asthma" refer to asthma in which one or any combination of the following are true: symptoms occur 2 or fewer days per week; symptoms do not interfere with normal activities; nighttime symptoms occur fewer than 2 days per month; or one or more lung function tests (e.g., forced expiratory volume in one second (FEV1) and/or peak expiratory flow (PEF) of greater than 80%) are normal when the subject is not suffering from an asthma attack. The present disclosure includes methods for improving intermittent asthma in a subject, which include administering a pharmaceutical composition including an anti-IL-4R antibody (e.g., an anti-IL-4Rα antibody, e.g., dupilumab) to the subject.

As used herein, the term "persistent asthma" refers to asthma that is more severe than asthma/intermittent asthma. A subject suffering from persistent asthma experiences one or more of the following: symptoms more than 2 days per week; symptoms that interfere with normal activities; nighttime symptoms that occur more than 2 days per month; or one or more lung function tests (e.g., forced expiratory volume in one second (FEV1) and/or peak expiratory flow (PEF) of less than 80%) that are not normal when the subject is not suffering from an asthma attack; the subject relies on daily asthma control medication; the subject has taken a systemic steroid more than once in the last year after a severe asthma flare-up; or use of a short-acting beta-2 agonist more than two days per week for relief of asthma symptoms. The present disclosure includes methods for improving persistent asthma in a subject, which include administering a pharmaceutical composition including an anti-IL-4R antibody (e.g., an anti-IL-4Rα antibody, e.g., dupilumab) to the subject.

Asthma/intermittent asthma and persistent asthma can be categorized as "mild," "moderate," "severe" or "moderate-to-severe." "Mild intermittent asthma" is defined as having symptoms less than once a week, and having forced expiratory volume in one second (FEV1) or peak expiratory flow (PEF)≥80%. "Mild persistent asthma" differs in that symptoms frequency is greater than once per week but less than once per day, and variability in FEV1 or PEF is <20%-30%. "Moderate intermittent asthma" is defined as having symptoms less than once a week, and having forced expiratory volume in one second (FEV1) or peak expiratory flow (PEF) of 60-80% "Moderate persistent asthma" is defined as having daily symptoms, exacerbations that can affect activity and/or sleep, nocturnal symptoms more than once a week, daily use of inhaled short-acting beta-2 agonist and having forced expiratory volume in one second (FEV1) or peak expiratory flow (PEF) of 60-80%. "Severe intermittent asthma" is defined as having symptoms less than once a week, and having forced expiratory volume in one second (FEV1) or peak expiratory flow (PEF) of 60%. "Severe persistent asthma" is defined as having daily symptoms, frequent exacerbations that can affect activity and/or sleep, frequent nocturnal symptoms, limitation of physical activities, daily use of inhaled short-acting beta-2 agonist, and having forced expiratory volume in one second (FEV1) or peak expiratory flow (PEF) of 60%. "Moderate-to-severe intermittent asthma" is defined as having symptoms between those of moderate intermittent asthma and severe intermittent asthma. "Moderate-to-severe persistent asthma" is defined as having symptoms between those of moderate persistent asthma and severe persistent asthma.

The present disclosure includes methods for improving mild, moderate, severe, or moderate-to-severe, mild intermittent, mild persistent, moderate intermittent, moderate persistent, severe intermittent, severe persistent, moderate-to-severe intermittent, moderate-to-severe persistent asthma in a subject, which include administering a pharmaceutical composition including an anti-IL-4R antibody (e.g., an anti-IL-4Rα antibody, e.g., dupilumab) to the subject.

As used herein, the term "inadequately controlled asthma" refers to patients whose asthma is either "not well controlled" or "very poorly controlled" as defined by the "Expert Panel Report 3: Guidelines for the Diagnosis and Management of Asthma," National Heart, Blood and Lung Institute, NIH, Aug. 28, 2007. "Not well controlled asthma" is defined as having symptoms greater than two days per week, nighttime awakenings one to three times per week, some limitations on normal activity, short-acting beta2-agonist use for symptom control greater than two days per week, FEV1 of 60-80% of predicted and/or personal best, an ATAQ score of 1-2, an ACQ score of 1.5 or greater, and an ACT score of 16-19. "Very poorly controlled asthma" is defined as having symptoms throughout the day, nighttime awakenings four times or more per week, extreme limitations on normal activity, short-acting beta2-agonist use for symptom control several times per day, FEV1 of less than 60% of predicted and/or personal best, an ATAQ score of 3-4, an ACQ score of N/A, and an ACT score of less than or equal to 15.

The present disclosure includes methods for improving inadequately controlled, not well controlled, very poorly controlled asthma in a subject in need thereof, which include administering a pharmaceutical composition including an anti-IL-4R antibody (e.g., an anti-IL-4Rα antibody, e.g., dupilumab) to the subject.

In some instances, a subject is identified as having moderate to severe uncontrolled asthma if the subject receives such a diagnosis from a physician, e.g., based on the Global Initiative for Asthma (GINA) 2009 Guidelines, and one or more of the following criteria: i) Existing treatment with moderate- or high-dose ICS/LABA (2 fluticasone propionate 250 µg twice daily or equipotent ICS daily dosage) with a stable dose of ICS/LABA for greater than or equal to 1 month prior to administration of the loading dose of an anti-IL-4R antibody (e.g., an anti-IL-4Rα antibody, e.g., dupilumab); ii) FEV1 40 to 80% predicted normal prior to administration of the loading dose of an anti-IL-4R antibody (e.g., an anti-IL-4Rα antibody, e.g., dupilumab); iii) ACQ-5 score greater than or equal to 1.5 prior to administration of the loading dose of an anti-IL-4R antibody (e.g., an anti-IL-4Rα antibody, e.g., dupilumab); iv) Reversibility of at least 12% and 200 mL in FEV1 after 200 µg to 400 µg (2 to 4 inhalations) of salbutamol/albuterol prior to administration of the loading dose of an anti-IL-4R antibody (e.g., an anti-IL-4Rα antibody, e.g., dupilumab); or v) has experienced, within 1 year prior to administration of the loading dose of an anti-IL-4R antibody (e.g., an anti-IL-4Rα antibody, e.g., dupilumab), any of the following events: a) treatment with greater than or equal to 1 systemic (oral or parenteral) steroid burst for worsening asthma, b) hospitalization or an emergency/urgent medical care visit for worsening asthma. The present disclosure includes methods for treating a subject diagnosed by a physician as having one or more of the above criteria, which includes administering a pharmaceutical composition including an anti-IL-4R antibody (e.g., an anti-IL-4Rα antibody, e.g., dupilumab) to the subject.

After a subject is identified as a candidate for therapy using the computational methods disclosed herein, an anti-IL-4R antibody (e.g., an anti-IL-4Rα antibody, e.g., dupilumab) can be administered to a subject with asthma.

Severe Asthma with Fungal Sensitivity (SAFS)

In some instances, a subject disclosed herein presents with Severe Asthma with Fungal Sensitivity (SAFS). SAFS can be conceptualized as a continuum of fungal sensitization, with asthma at one end and allergic bronchopulmonary aspergillosis at the other. It is diagnosed by the presence of severe asthma, fungal sensitization, and exclusion of allergic bronchopulmonary aspergillosis. SAFS presents with severe asthma, a total IgE<1,000 IU/mL, and sensitization to any fungus by skin prick test or sIgE. See Denning et al., *Clin Transl Allergy*. 2014; 4: 14, and Agarwal, each of which is incorporated by reference in its entirety. In some instances, SAFS is a result of an infection of one or more of an *Alternaria* spp., an *Aspergillus* spp., an *Aureobasidium* spp., a *Botrytis* spp., a *Candida* spp., a *Cladosporium* spp., an *Epicoccum* spp., a *Helminthosporium* spp., *Penicillium* spp., a *Trichophyton* spp., or any combination thereof.

Disclosed herein are methods of treating a subject having SAFS which include administering an anti-IL-4R antibody (e.g., an anti-IL-4Rα antibody, e.g., dupilumab). Also disclosed are methods of alleviating, ameliorating, or preventing reactions associated with SAFS, which include administering an anti-IL-4R antibody (e.g., an anti-IL-4Rα antibody, e.g., dupilumab).

Nasal Polyposis

Nasal polyposis (NP) is a clinical condition characterized by the presence of multiple polyps in the upper nasal cavity, originating from the ostiomeatal complex. NP is a T helper cell-2 (Th-2) driven inflammatory process affecting the mucosa of the nose and paranasal sinuses. Eosinophils and their products are hallmarks of nasal polyp-associated inflammation as elevated levels of interleukin-5 (IL-5; promotes eosinophil survival and differentiation), eosinophil cationic protein (ECP), and eotaxin (eosinophil chemoattractant), factors that attract and activate eosinophils, are typically found in nasal polyps. Eosinophils are the predominant inflammatory cell found in the sinuses and nasal polyps, and nasal polyps are also associated with elevated levels of IgE.

NP is characterized by long-term symptoms of nasal obstruction and congestion, reduction in or loss of sense of smell, anterior and posterior rhinorrhea, and facial pain. The presence or absence of nasal polyps can be confirmed for example by performing endoscopy, and the presence and extent of sinus and polyp involvement can be confirmed by methods such as coronal computed tomography (CT) scans.

As used herein, a "nasal polyp" is an overgrowth of tissue in one or more of the nasal cavities. The condition of nasal polyps is called "nasal polyposis." About 80% of nasal polyps are highly edematous and filled with eosinophils. Nasal polyps can also present as fibrous, glandular or cystic.

An anti-IL-4R antibody (e.g., an anti-IL-4Rα antibody, e.g., dupilumab) can be used to treat nasal polyposis associated with a variety of conditions. For example, nasal polyposis is associated with sinusitis, rhinitis (e.g., allergic and non-allergic rhinitis), asthma (e.g., moderate-to-severe asthma), NSAID sensitivity (e.g., aspirin sensitivity), and infection, such as bacterial and fungal infection. Bacterial infections include, for example, staphylococcus infections. A subject with nasal polyposis can have a chronic infection, such as a chronic bacterial infection, e.g., a chronic *Staphylococcus aureus* infection. In some instances, the subject has recurring nasal polyposis, such as can be associated with recurring sinusitis. In some instances, the subject has cystic fibrosis or NARES (Non-Allergic Rhinitis with Eosinophilia Syndrome). In other instances, the subject has a relapse of nasal polyposis after receiving surgery to treat the polyps. Risk factors for nasal polyposis include genetic susceptibility, anatomic abnormality, mucociliary impairment, infection, and local immunologic imbalance.

An anti-IL-4R antibody (e.g., an anti-IL-4Rα antibody, e.g., dupilumab) can be used to treat nasal polyposis in patients who have never previously received a treatment or surgery for NP. An anti-IL-4R antibody (e.g., an anti-IL-4Rα antibody, e.g., dupilumab) can be used to treat nasal polyposis in patients who have previously undergone surgery, such as a nasal surgery, such as for treatment of nasal polyps. In certain instances, an anti-IL-4R antibody (e.g., an anti-IL-4Rα antibody, e.g., dupilumab) is administered to a subject whose nasal polyposis has relapsed after the subject received prior treatment for the polyps, such as a prior nasal surgery.

Disclosed herein are methods of treating a subject having NP by administering an anti-IL-4R antibody (e.g., an anti-IL-4Rα antibody, e.g., dupilumab). Also disclosed herein are methods of alleviating, ameliorating, or preventing reactions associated with NP by administering an anti-IL-4R antibody (e.g., an anti-IL-4Rα antibody, e.g., dupilumab).

After a subject is identified as a candidate for therapy using the computational methods disclosed herein, an anti-IL-4R antibody (e.g., an anti-IL-4Rα antibody, e.g., dupilumab) can be administered to a subject with asthma. Also disclosed herein are methods of alleviating, ameliorating, or preventing reactions associated with NP by administering an anti-IL-4R antibody (e.g., an anti-IL-4Rα antibody, e.g., dupilumab) after a subject is identified as a candidate for therapy using the computational methods disclosed herein.

Nasal Polyposis is described in further detail in U.S. Pat. No. 10,059,771 B2, which is incorporated by reference in its entirety.

Sinusitis and Rhinitis

As used herein, the term "sinusitis" refers to any inflammatory condition characterized by inflammation of the paranasal sinuses, including inflammation of the maxillary, frontal, ethmoid and/or sphenoid paranasal sinuses. An anti-IL-4R antibody (e.g., an anti-IL-4Rα antibody, e.g., dupilumab) is suitable for treatment of nasal polyposis associated with acute sinusitis, subacute sinusitis, chronic sinusitis and recurrent sinusitis. Acute sinusitis is characterized by a sudden onset of cold-like symptoms such as runny, stuffy nose and facial pain that does not go away after 10 to 14 days. Acute sinusitis typically lasts less than four weeks. Subacute sinusitis lasts four to eight weeks. Chronic sinusitis lasts eight weeks or longer, and recurrent sinusitis is characterized by sinusitis episodes that occur three or more times in one year. More than 80% of patients with chronic sinusitis with nasal polyps have eosinophilic upper airway inflammation.

Many patients with chronic sinusitis have "chronic hyperplastic eosinophilic sinusitis," which is characterized by marked inflammation of the sinuses, increased eosinophils and mixed mononuclear cells, and a relative paucity of neutrophils. Some of these patients have one or more of associated nasal polyps, asthma, and aspirin or NSAID sensitivity. An anti-IL-4R antibody (e.g., an anti-IL-4Rα antibody, e.g., dupilumab) can be used to treat nasal polyposis in a subject who has chronic hyperplastic eosinophilic sinusitis.

The term "rhinitis" refers to an allergic response, such as to a common allergen ("allergic rhinitis," e.g., perennial allergic rhinitis) or to an environmental irritant ("non-allergic rhinitis"). In some instances, a subject has allergic rhinitis. Symptoms of allergic rhinitis include sneezing; stuffy or runny nose; sinus pressure, and pain or throbbing in the cheeks or nose; and itching in the nose, throat, eyes and ears.

In some instances, the rhinitis is chronic rhinitis. Chronic rhinitis is long term nasal inflammation. In some instances, chronic rhinitis is seasonal. In some instances, chronic rhinitis occurs in winter months. In some instances, a subject described herein has chronic rhinitis.

Symptoms of non-allergic rhinitis include constriction or inflammation in the nasal passages which leads to many of the same symptoms of allergic rhinitis. Non-allergic rhinitis can be caused, for example, by strong chemical or smoky environments, or by long-term use of certain medications or dependency on nasal sprays.

As used herein, the term "rhinosinusitis" refers to a condition that has symptoms of both rhinitis and sinusitis. Rhinosinusitis includes acute rhinosinusitis and chronic rhinosinusitis. Acute rhinosinusitis can be caused by an infection, such as a bacterial, viral or fungal infection, or by a chemical irritation. Cigarette-smoke-induced acute rhinosinusitis and chlorine fume-induced chronic rhinosinusitis are examples of rhinosinusitis. NP is most commonly associated with chronic rhinosinusitis (CRS), which is characterized by mucosal inflammation of the nasal cavity and paranasal sinuses with symptoms lasting more than 8 weeks. Chronic eosinophilic rhinosinusitis with nasal polyps is a condition that lasts longer than 8 weeks.

Obstructive Sleep Apnea (OSA) is a common disorder with serious consequences that is associated with rhinosinusitis, with >80% of OSA patients undiagnosed, and undertreated due to inadequate treatment options. OSA is caused by collapse of the pharyngeal airway during sleep due to the sleep state-related loss of pharyngeal muscle activity. High nasal resistance can contribute to pharyngeal collapse as well by increasing the suction pressure downstream in the velo- and oropharynx. Therefore, a drug that reduces nasal congestion and pharyngeal edema, such as an anti-IL-4R antibody (e.g., an anti-IL-4Rα antibody, e.g., dupilumab), could potentially improve OSA in some patients.

Chronic sinusitis (CS), an inflammatory condition of the sinuses, is a common syndrome, with estimates of prevalence as high as 13% in Western populations. CS and chronic rhinosinusitis (CRS) are conditions that last longer than eight weeks. The underlying causes of acute sinusitis and acute rhinosinusitis can lead to chronic sinusitis or chronic rhinosinusitis if the resulting inflammation persists for more than 8 weeks. Chronic rhinosinusitis includes for example, eosinophilic chronic hyperplastic rhinosinusitis.

In some instances, chronic sinusitis is chronic rhinosinusitis with nasal polyposis or CRS without nasal polyps (CRSwNP). CRSwNP has characteristics with high infiltration of tissue eosinophilia with a burst of Th2 inflammatory cytokine. Defects in the innate function of the airway epithelial barrier, including diminished expression of antimicrobial products and loss of barrier integrity, combined with colonization by fungi and bacteria likely play a critical role in the development of chronic inflammation in CRSwNP. See Hulse et al., *Clin Exp Allergy.* 2015 February; 45(2): 328-346, which is incorporated by reference in its entirety.

Disclosed herein are methods of treating a subject having CRSwNP which include administering an anti-IL-4R antibody (e.g., an anti-IL-4Rα antibody, e.g., dupilumab). Also disclosed are methods of alleviating, ameliorating, or preventing reactions associated with CRSwNP, which include administering an anti-IL-4R antibody (e.g., an anti-IL-4Rα antibody, e.g., dupilumab).

In some instances, chronic sinusitis is chronic rhinosinusitis sans nasal polyposis or CRS without nasal polyps (CRSsNP). In some instances, CRSsNP is thought to result from recurrent episodes of acute rhinosinusitis or occlusion of the sinus ostium secondary to anatomic variation, which may contribute to hypoxia development in sinus cavities. When compared to CRSsNP or control, CRSwNP has increased levels of Th2 mediators including IL-5, IL-13, and eotaxin-2. See Stevens et al., *Am J Respir Crit Care Med.* 2015; 192:682-694, which is incorporated by reference in its entirety. In some instances, certain diseases predispose a subject to CRSsNP. In some instances, predisposing diseases include allergic and non-allergic upper and lower airway diseases, epithelial cell disorders, immunodeficiencies, autoimmune diseases, and some infectious diseases. Additionally, in some instances, environmental and host factors, examples of which include smoking, a higher incidence of abnormal biofilms, and innate immune defects play a role in the pathogenesis of this disease. CRSsNP is characterized by histologic abnormalities, including basement membrane thickening (e.g., fibrosis) and goblet cell hyperplasia. In some instances, neutrophils and several chemokines, TGF-β and CXCL-8, play a role in CRSsNP remodeling. See Cho et al., *J Allergy Clin Immunol Pract.* 2016 July-August; 4(4): 575-582, which is incorporated by reference in its entirety.

Disclosed herein are methods of treating a subject having CRSsNP which include administering an anti-IL-4R antibody (e.g., an anti-IL-4Rα antibody, e.g., dupilumab). Also disclosed are methods of alleviating, ameliorating, or preventing reactions associated with CRSsNP, which include administering an anti-IL-4R antibody (e.g., an anti-IL-4Rα antibody, e.g., dupilumab).

In some instances, methods disclosed herein include treatment of allergic fungal rhinosinusitis (AFRS). In some instances, AFRS includes a hypersensitivity reaction to fungal antigens. In some instances, a subject having AFRS also has CRSwNP. In some instances, the fungus is from the genus *Aspergillus*. In some instances, AFRS presents with a thick, tenacious, eosinophilic secretion. This mucin is grossly and microscopically similar to that found in the lungs of patients with allergic bronchopulmonary aspergillosis (ABPA). See Glass and Amedee, *Ochsner J.* 2011 Fall; 11(3): 271-275, which is incorporated by reference in its entirety.

Disclosed herein are methods of treating a subject having AFRS which include administering an anti-IL-4R antibody (e.g., an anti-IL-4Rα antibody, e.g., dupilumab). Also disclosed are methods of alleviating, ameliorating, or preventing reactions associated with AFRS, which include administering an anti-IL-4R antibody (e.g., an anti-IL-4Rα antibody, e.g., dupilumab).

Additional subcategories of chronic sinusitis (and chronic rhinosinusitis) include, e.g., superantigen-induced eosinophilic chronic sinusitis (e.g., sinusitis induced by exo- and endo-toxins produced by bacteria such as *Staphylococcus aureus*); allergic fungal sinusitis (e.g., sinusitis induced by fungi such as *Aspergillus* or *Alternaria*); non-allergic fungal eosinophilic chronic sinusitis; and aspirin-exacerbated eosinophilic chronic sinusitis.

Disclosed herein are methods of treating a subject having chronic sinusitis (and chronic rhinosinusitis) which include administering an anti-IL-4R antibody (e.g., an anti-IL-4Rα antibody, e.g., dupilumab). Also disclosed are methods of alleviating, ameliorating, or preventing reactions associated with chronic sinusitis (and chronic rhinosinusitis), which include administering an anti-IL-4R antibody (e.g., an anti-IL-4Rα antibody, e.g., dupilumab).

After a subject is identified as a candidate for therapy using the computational methods disclosed herein, an anti-IL-4R antibody (e.g., an anti-IL-4Rα antibody, e.g., dupilumab) can be administered to a subject having chronic sinusitis (and chronic rhinosinusitis). Also disclosed herein are methods of alleviating, ameliorating, or preventing reactions associated having chronic sinusitis (and chronic rhinosinusitis) by administering an anti-IL-4R antibody (e.g., an anti-IL-4Rα antibody, e.g., dupilumab) after a subject is identified as a candidate for therapy using the computational methods disclosed herein. CS is further disclosed in U.S. Pat. No. 10,066,017 B2, which is incorporated by reference in its entirety.

Additional Indications

The above indications have been determined based at least in part using computational methods that analyze data obtained from over 90 million patients and predict therapeutic outcomes for specific drugs. Starting with those predictions, the present inventors have identified various diseases and disorders that be treated using an anti-IL-4R antibody (e.g., an anti-IL-4Rα antibody, e.g., dupilumab). However, in some instances, the IL-4Rα-related disorder is not one of atopic dermatitis, asthma, chronic rhinosinusitis with nasal polyposis, eosinophilic esophagitis, a peanut allergy, a grass allergy, chronic obstructive pulmonary disease (COPD), prurigo nodularis, bullous pemphigoid, chronic spontaneous urticaria (CSU), allergic bronchopulmonary aspergillosis (ABPA), or any combination thereof. In some instances, the IL-4Rα-related disorder is not atopic dermatitis. In some instances, the IL-4Rα-related disorder is not asthma. In some instances, the IL-4Rα-related disorder is not chronic rhinosinusitis with nasal polyposis. In some instances, the IL-4Rα-related disorder is not eosinophilic esophagitis. In some instances, the IL-4Rα-related disorder is not a peanut allergy. In some instances, the IL-4Rα-related disorder is not a grass allergy. In some instances, the IL-4Rα-related disorder is not chronic obstructive pulmonary disease (COPD). In some instances, the IL-4Rα-related disorder is not prurigo nodularis. In some instances, the IL-4Rα-related disorder is not bullous pemphigoid. In some instances, the IL-4Rα-related disorder is not chronic spontaneous urticaria (CSU). In some instances, the IL-4Rα-related disorder is not allergic bronchopulmonary aspergillosis (ABPA).

EXAMPLES

The disclosure is further described in the following examples, which do not limit the scope of the disclosure described in the claims.

Example 1: Drug Repurposing of Dupilumab

Figure 3:
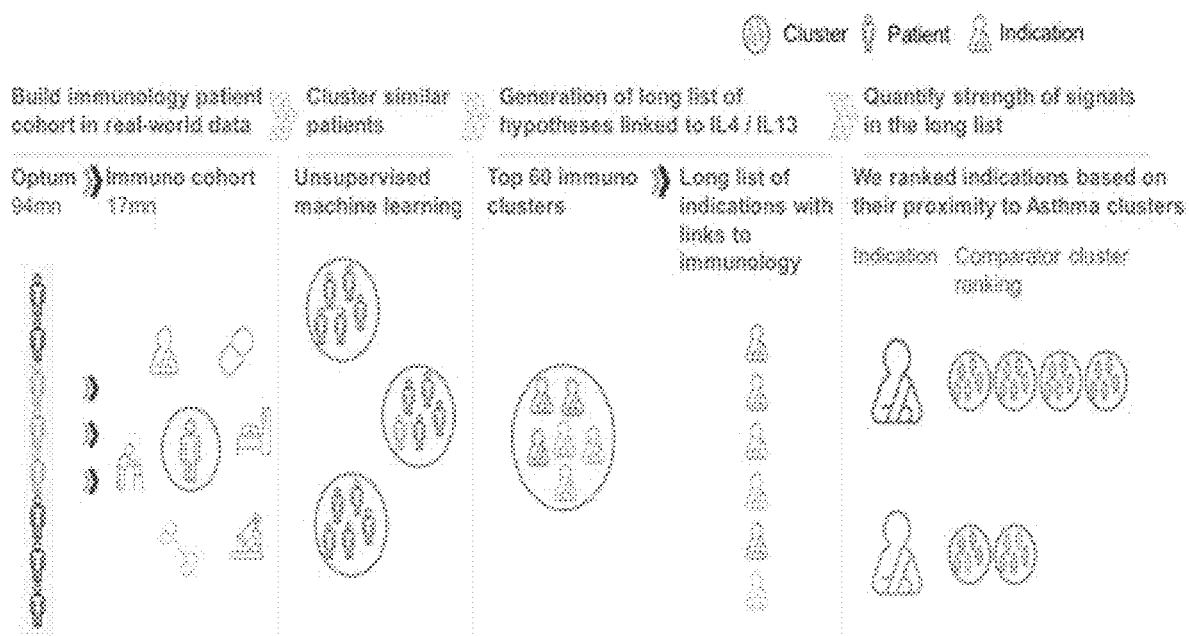
FIG. 3 is a diagram illustrating an experiment using the systems and methods described in this specification.

FIG. 3 is a diagram illustrating an experiment using the systems and methods described in this specification. The experiment was conducted to validate a RWD-driven protocol for drug repurposing of Dupilumab, which is an anti-IL-4/IL-13 drug, in order to identify novel indications of the drug. One goal of the experiment was to reduce drug development cost and time to market, while minimizing attrition and risk. A hybrid approach was applied using scientific and clinical competences through KOL expertise, commercial assessment, and analytics combined with real world data.

Data Source: The Optum Humedica dataset for the years 2014 to 2018 was used. The database contained electronic medical records for 94 million patients identifiable by a key identifier, that allowed matching of patients across different data tables. The database collected information on EMR data, such as diagnosis, lab test, procedures, medications, patient events, insurance, biomarkers, measurements, clinical status and lifestyle parameters, microbiology, and prescriptions. Natural Language Processing (NLP)-driven tables were not included, due to limited data coverage and clinical relevance. Furthermore, data tables that were incomplete or contained irrelevant information were excluded. A total of 5 data tables were included which reduced the data source to 40 million patients.

Selection of Patients: Indicators for patient selection were based on the clinical framework related to the underlying immunology pathways, as shown in Table 7.

TABLE 7

Factors used to identify indications to consider for patient selection

| Factor | Focused lens - Th2 dysfunction causing disease | Medium lens - Th2 response associated with disease | Broad lens - Th2 response plausibly associated with disease |
|---|---|---|---|
| Pathway mechanisms | Eosinophilia IL-4 pathway IL-5 pathway IL-13 pathway | Hypersensitivity type 1 Hypersensitivity type 4 Pruritus | Correlated autoimmune conditions Other autoimmune and/or inflammatory pathways End organ inflammatory conditions (e.g., cardio inflammatory, respiratory, renal) Oncology pathways |
| Related clinical conditions | Eosinophilic esophagitis Eosinophilic granulomatosis with polyangiitis (Churg-Strauss Syndrome) | Anaphylaxis Allergic conjunctivitis Urticaria | Thyroiditis Pancreatitis Amyloidosis Basel cell carcinoma |
| Therapeutic analogues | IL-4 inhibitors IL-5 inhibitors IL-13 inhibitors | Downstream pathway modulators JAK inhibitors STAT inhibitors GATA inhibitors IL-25 Upstream pathway modulators IL-2 inhibitors | Other pathway determining interleukin targets: IL-1, IL-6, IL-12, IL-21, IL-23 Downstream interleukin targets: IL-9, IL-17, IL-22 Other potential proinflammatory targets: IFN, TGFβ, TNFα |
| Data and epidemiology | Eosinophilic conditions | Hypersensitivity type 1 conditions | Autoimmune conditions Inflammatory conditions Oncology diseases |
| LCM strategy alignment | Eosinophilic esophagitis Adjunctive therapy for peanut and grass allergy | Chronic rhinosinusitis Chronic spontaneous urticaria Atopic keratoconjunctivitis | |

Data from adult patients (aged≥18 years old) with at least one diagnosis, medication, lab test and procedure who ever suffered from an IL-4/IL-13 pathway (i.e., signaling pathway) associated diagnosis and who were active in the 5 year window 2014-2018, were used in the analysis. Using these criteria of immunology conditions and data completeness, the resulting cohort consisted of 17 million unique patients.

Five factors (as shown in Table 7) were considered for identifying indications. These factors were searched through sources on Doctor Evidence engine database, a medical evidence software and services company composed of several platforms (DOC Library, DOC Data, Doctor Evidence, DOC Label, DOC Search) and including PubMed, ClinicalTrials.gov, WHO, and so forth. Information within these factors was then classified according to three lenses based on Th2 response: focused, medium and broad. For example, diseases were allocated to the focused or medium lens based on their direct and indirect relationship with IL-4/IL-13 mechanism of action on the Th2 pathway respectively, and to the broad lens if they were associated with a broader inflammatory response. Moving from the focused to the broad lens increased the range of indicators to be considered and reduced the likelihood of molecule impact. Indications in the broad lens were eventually excluded from the analysis as their mechanistic link wasn't specific enough to meet criteria for identifying patient populations with similar characteristics. Hence, only indications for the focused and medium lenses were included in the experiment. A final list of 208 indications were included for analysis across 17 broad systems.

Selection of features: Broad features (patient characteristics) were selected to capture the available information in the Optum dataset; then, features selected by clinical experts were prioritized and validated to ensure that all essential variables were included, and the variable values made clinical sense. When appropriate, certain features were retained while others (certain demographics) were created de novo (as shown by V1 as described later with reference to FIG. 4). New features were added based on clinical input and demographics, medication, comorbidities, procedures and laboratory tests data specific to immunology. Bespoke feature classes were created and added to the analysis iteratively (as shown by V2 and V3 as described later with reference to FIG. 4) to increase data completeness, representativeness, and collect more information on the severity of the disease and drug response.

A robust approach was used to ensure the completeness of the features in the final database. Two validation steps, based on patient and feature mapping across the Optum database and the generated table, were taken to verify that the features were generated correctly. First, to validate whether the patient features in Optum mapped to our data table correctly, the percentage of patients with at least one feature family was calculated and it was determined whether this number was identical in Optum Humedica and our data table. Second, to validate whether the features mapped to the correct patient, ten random patients were tracked from the raw Optum Humedica data to the generated dataset, to ensure identical mapping of features in the two datasets. After the feature validation had demonstrated the correct mapping, the algorithm was run on 17 million patients with 2700 features included.

Clustering: A clustering technique was used to group patients together that share similar characteristics as defined by features related to the IL-4/IL-13 pathway. The clustering looked for similarities between patients based on their features. The generated clusters resulted in finding correlations among conditions, even if they weren't present in the same patient. Clinical inputs were embedded in various stages of the process to ensure the clinical relevance of the results. Thus, disease experts' clinical inputs assisted in the creation of clinically relevant cohorts, in the inclusion and grouping of clinically relevant features and finally in the cluster validation and assessment. Features were identified as being distinctive in clusters if they occurred more frequently than in the general population.

Figure 4:
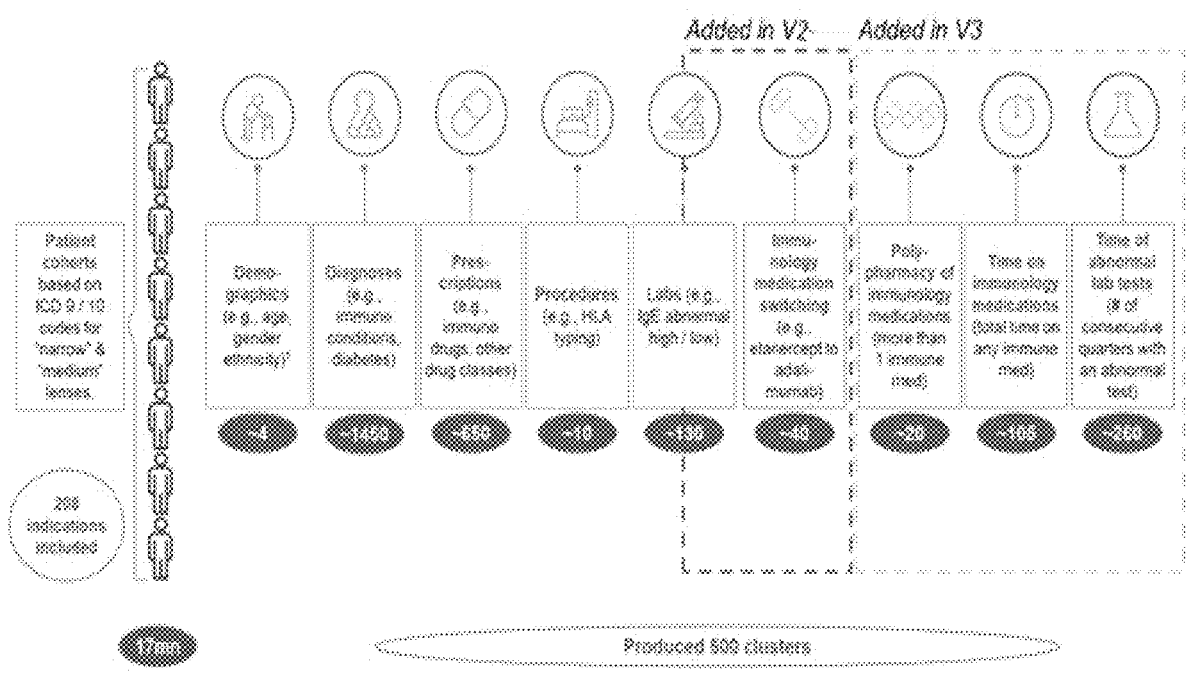
FIG. 4 is a diagram illustrating the ordered list of features for the input data that created the feature vector used for clustering. The feature vector was created using Multiple Correspondence Analysis (MCA).

Multiple Correspondence Analysis (MCA) was used to reduce the dimensions of the features. Bisecting K-means was then utilized to split the data into 500 clusters, to provide an appropriate and effective separation of patients with sufficiently 'tight' but stable clusters and allow a large number of clusters that exhibited immuno-relatedness to be used for the indication scoring. The clusters identified through the process were validated and assessed by clinical experts. This step facilitated the reduction in risk of non-interpretability of the clusters and ensured the absence of overlapping features between the different clusters. The clustering approach ran on 2700 features and 17 million patients (see FIG. 4). The number of clusters produced at the end of the algorithm was 500 (FIG. 4).

Identification of new indications (i.e., relevant patient characteristics): Further assessment, clinical and commercial judgement were performed to obtain a short list of priority signals and identify the most clinically relevant indications across clusters based on the cluster outputs. Four methodological steps were used. The first one selected the top 60 clusters among the 500 ranked, based on immunology enrichment, stability, purity, and size. Three measures were calculated for the features included in each cluster to determine the selection: distinctiveness, the number of patients presenting the feature within each cluster, and the immunology score. The distinctiveness, also called "lift score", measured how distinctive a feature is within a cluster versus the rest of the population (e.g. if males represent 50% of the population and 75% of the cluster, then the lift score is equal to 1.5). Only the features with a lift score>1 (meaning they occurred in the cluster at a higher rate than expected compared to a broader population) and appearing in ≥10% of the patients were considered for defining (and naming) a cluster and developing themes of clusters. In addition, each selected feature was given a score according to its type (disease, drug, laboratory test or procedure) and immunology relevance. The features scores within each cluster were summed up and normalized. The clusters were then considered as immunology-specific if they met a pre-defined threshold of the score of 50%. As a second step, the clusters were selected according to stability, purity, and the number of patients. The stability was assessed using four methods: 1. reproducing the clusters on different sizes of data, 2. changing the initializing seeds of the clusters, 3. changing the number of clusters produced and 4. applying a train-test method. For each cluster in the train set, stability is defined as the maximum proportion of patients that are also grouped together in the test set. Purity was measured by the intra-cluster variance of MCA components of patients within that cluster, resulting in homogenous and dense clusters. A cluster is included in the analysis if it has more than 50% stability and is in the highest 20% of purity. In addition, all the indications judged by subject-matter experts as relevant to the core cluster theme were considered for evaluation, regardless of the number of patients in which these features appeared (might be <10%). These new indications were then ranked based on the frequency of co-occurrence with each of the four established indications (referential) of dupilumab (asthma, atopic dermatitis, IgE allergy, and the composite immunology score) in the third step. The co-occurrence was measured by calculating the proportion of patient-weighted clusters that contain both the indication and the referential. In the last step, the final list of indications was further characterized by clinical and commercial feasibility. The clinical assessment retained the indications that showed a distinct clinical diagnosis. Based on the ranking with the IL-4/IL-13 referential, conditions that did not appear in the top 30 were deleted as they looked to be poorly related to IL-4/IL-13 modulation. The commercial assessment was possible only for a subset of clinically plausible indications, where the data on forecast sales and competitor assets were available. In addition, multiple factors were also considered for the commercial assessment: the link to the IL-4/IL-13 pathway, whether found or not in the literature, the worldwide prevalence of the indication and the disability-adjusted life year (DALY) of the indication (per 100,000 life years).

Results: FIG. 4 is a diagram illustrating the ordered list of features for the input data that created the feature vector used for clustering. The feature vector was created using Multiple Correspondence Analysis (MCA). The final cohort of 17 million patients, extracted from Optum Humedica, was analyzed to assess data completeness and representativeness across the selected features. In the medium lens population, the cohort of patients was composed of 59% females, mostly Caucasian (77%), with mean age at last activity of 53 years (SD=19 years) and mean follow up period of 7.4 years. Patients presented most frequently ICD10 codes for acute sinusitis (25.2%), allergic rhinitis, unspecified (20.6%), and other and unspecified asthma (19.4%) as immunology conditions. The most frequent immunology-related medications were prednisone (28.0%), fluticasone furoate (22.2%), and methylprednisolone (13.3%), and 0.4% of patients underwent allergen immunotherapy injections and beta2 glycoprotein antibody measurement. Most of the patients were tested for white blood cell count (70.8%), absolute neutrophils count (ANC) (64.3%), and absolute lymphocyte count (ALC) (63.8%). The clustering procedure created 500 clusters (see FIG. 4), out of which 125 were classified as both enriched for immune conditions and stable. Of these 125, 110 were also classified as pure. Among these, 60 clusters containing the largest number of patients per cluster were retained and analyzed for clinically relevant signals. Following the validation process, 84% of the clusters were considered highly stable using the train-test method, 90% and 99% of the top 20 clusters were reproduced regardless of the seed position and the number of patients in data table respectively. Six cluster themes were identified based on the features included in the clusters and reproduced in part also in the V2 and V3 iterations: multi-organ immunological impact, neoplasia, asthma and other hypersensitivities, musculoskeletal dysfunction, cardiometabolic spectrum, and gynecology & maternity conditions. Among them, 250 indications were selected by cluster assessment (Table 8). These 250 indications were ranked to identify the top 30 indications, based on co-occurrence with at least one of four referential "immunological conditions": asthma, atopic dermatitis, hyperimmunoglobulin E (IgE) syndrome and a broader composite immunology score. The rankings are shown in FIGS. 6A-6D. The indications in the four referential groups (minus indications known to be part of a clinical trial already, including investigator-initiated trials) were then re-ranked to generate the lists shown in FIGS. 7A-7D. The italicized indications appear in more than one comparator group. These four lists were compared and used to consider which new indications should be prioritized for further review. A list of 86 indications were accordingly identified as highest priority (Table 9).

TABLE 8

250 Indications Selected by Cluster Assessment

Indications

Acanthosis Nigricans
Acne
Acute Lymphadenitis
Acute Nephritic Syndrome
Acute Nephritic Syndrome With Unspecified Morphologic Changes
Acute Pericarditis
Acute Sinusitis
Addisonian Crisis
Adult-Onset Still'SDisease
Allergic And Dietetic Gastroenteritis And Colitis
Allergic Bronchopulmonary Aspergillosis
Allergic Dermatitis Of Eyelid
Allergic Rhinitis
Allergic Rhinitis, Unspecified TABLE 8-continued 250 Indications Selected by Cluster Assessment Indications Allergy Status To Drugs, Medicaments And Biological Substances
Alopecia Areata
Amyloidosis
Amyotrophic Eateral Sclerosis
Anaphylaxia
Anca-Vasculitis
Angioneurotic Edema, Initial Encounter
Ankylosing Spondylitis
Arthropathic Psoriasis
Atopic Conjunctivitis
Autoimmune Lymphoproliferative Syndrome [Alps]
Autoimmune Thyroiditis
Benign Neoplasm Of Unspecified Kidney
Benign Neuroendocrine Tumors
Benign Prostatic Hyperplasia
Bronchiectasis
Bullous Pemphigoid
Carcinoma In Situ Of Breast
Carcinoma In Situ Of Cervix Uteri
Celiac Disease
Cellulitis And Acute Lymphangitis
Cholecystitis
Chronic Diseases Of Tonsils And Adenoids
Chronic Giant Papillary Conjunctivitis
Chronic Hepatitis, Not Elsewhere Classified
Chronic Kidney Disease (Ckd)
Chronic Laryngitis And Laryngotracheitis
Chronic Myelomonocytic Leukemia
Chronic Myeloproliferative Disease
Chronic Nasopharyngitis
Chronic Nephritic Syndrome
Chronic Rhinitis
Chronic Rhinitis, Nasopharyngitis And Pharyngitis
Chronic Sinusitis
Chronic Tubulo-Interstitial Nephritis
Cicatricial Alopecia [Scarring Hair Loss]
Coalworker'S Pneumoconiosis
Congenital Ichthyosis, Unspecified
Conjunctivitis
Contact Dermatitis
Coronary Atherosclerosis
Cr(E)St Syndrome
Crohn's Disease [Regional Enteritis]
Cystitis
Dermatitis Due To Substances Taken Internally
Dermatitis Herpetiformis
Dermatitis, Unspecified
Dermatopolymyositis
Diffuse (Eosinophilic) Fasciitis
Diverticular Disease Of Intestine
Drug-& Heavy-Metal-Induced Tubulo-Interstitial & TublrCond
Drug-And Heavy-Metal-Induced Tubulo-Interstitial And Tubular Conditions
Dyshidrosis[Pompholyx]
Eccrine Sweat Disorders
Eczematous Dermatitis Of Eyelid
Emphysema
Encephalitis, Myelitis And Encephalomyelitis
End Stage Renal Disease
Endometriosis
Eosinophilia
Eosinophilic Colitis
Eosinophilic Esophagitis
Eosinophilic Gastritis Or Gastroenteritis
Epidermolysis Bullosa
Erythema Multiforme
Erythema Nodosum
Esophagitis
Essential (Hemorrhagic) Thrombocythemia
Exfoliative Dermatitis
Extrinsic Allergic Alveolitis
Felty'SSyndrome
Fibroblastic Disorders
Follicular Lymphoma TABLE 8-continued 250 Indications Selected by Cluster Assessment Indications Food Allergy
Fuchs' HeterochromicCyclitis
Gastritis And Duodenitis
Gastro-Esophageal Reflux Disease
Giant Cell Arteritis With Polymyalgia Rheumatica
Gout
Graft-Versus-Host Disease
Granuloma Faciale [Eosinophilic Granuloma Of Skin]
Guillain-Barre Syndrome
Hemangioma Of Skin And Subcutaneous Tissue
Hepatic Fibrosis
Hepatic Fibrosis With Hepatic Sclerosis
Hereditary Hemorrhagic Telangiectasia
Hodgkin Lymphoma
Hyperimmunoglobulin E [Ige] Syndrome
Hypersensitivity Pneumonitis Due To Organic Dust
Hypertrophy Of Adenoids
Idiopathic Pulmonary Fibrosis
Inflammatory Disease Of Cervix Uteri
Inflammatory Polyarthropathy
Inflammatory Polyneuropathy
Interstitial Cystitis (Chronic)
Iridocyclitis
Irritable Bowel Syndrome
Juvenile Ankylosing Spondylitis
Juvenile Rheumatoid Arthritis
Kaposi'SSarcoma
Keratitis
Lichen Planus
Lichen Simplex ChronicusAnd Prurigo
Localized Scleroderma [Morphea]
Lupus (Sle/Ln)
Lymphoid Leukemia
Malignant Immunoproliferative Diseases And Certain
Other B-Cell Lymphomas
Malignant Melanoma Of Skin
Malignant Neoplasm Of Bladder
Malignant Neoplasm Of Brain
Malignant Neoplasm Of Breast
Malignant Neoplasm Of Bronchus And Lung
Malignant Neoplasm Of Cervix Uteri
Malignant Neoplasm Of Colon
Malignant Neoplasm Of Esophagus
Malignant Neoplasm Of Eye And Adnexa
Malignant Neoplasm Of Head, Face And Neck
Malignant Neoplasm Of Kidney, Except Renal Pelvis
Malignant Neoplasm Of Liver And Intrahepatic Bile Ducts
Malignant Neoplasm Of Nasal Cavity And Middle Ear
Malignant Neoplasm Of Ovary
Malignant Neoplasm Of Pancreas
Malignant Neoplasm Of Prostate
Malignant Neoplasm Of Rectum
Malignant Neoplasm Of Small Intestine
Malignant Neoplasm Of Stomach
Malignant Neoplasm Of Testis
Malignant Neoplasm Of Thyroid Gland
Malignant Neuroendocrine Tumors
Mastoiditis And Related Conditions
Mature T/Nk-Cell Lymphomas
Melanocytic Nevi
Melanoma In Situ
Merkel Cell Carcinoma
Mesothelioma
Monocytic Leukemia
Multiple Myeloma And Malignant Plasma Cell Neoplasms
Multiple Sclerosis
Myasthenia Gravis And Other Myoneural Disorders
Myelodysplastic Syndromes
Myelofibrosis
Myeloid Leukemia
Myeloid Leukemia
Myositis
Nasal Polyp
Nephrotic Syndrome
Neurofibromatosis, Type 2
Neuromyelitis Optica [Devic]
Non-Celiac Gluten Sensitivity
Non-Follicular Lymphoma
Nonsuppurative Otitis Media
Nummular Dermatitis
Obstructive Sleep Apnea (Adult) (Pediatric)
Optic Neuritis
Orchitis And Epididymitis
Osteo-Arthritis
Other And Unspecified Allergy
Other Chronic Obstructive Pulmonary Disease
Other Dermatomyositis
Other Female Pelvic Inflammatory Diseases
Other Forms Of Systemic Sclerosis
Other Giant Cell Arteritis
Other Phakomatoses, Not Elsewhere Classified
Other Respiratory Conditions Due To Chemicals, Gases, Fumes And Vapors
Other Specified And Unspecified Types Of Non-Hodgkin Lymphoma
Other Specified Dermatitis
Other Specified Disorders Involving The Immune Mechanism, Not Elsewhere Classified
Other Specified Disorders Of Nose And Nasal Sinuses
Other Specified Systemic Involvement Of Connective Tissue
Other Specified Types Of T/Nk-Cell Lymphoma
Otitis Externa
Otosclerosis
Pityriasis Rosea
Pneumoconiosis Due To Dust Containing Silica
Polyarteritis Nodosa And Related Conditions
Polycythemia Vera
Polymyalgia Rheumatica
PostinfectiveAnd Reactive Arthropathies
Primary Adrenocortical Insufficiency
Primary Biliary Cirrhosis
Progressive Systemic Sclerosis
Pruritus
Pruritus, Unspecified
Psoriasis
Pulmonary Eosinophilia, Not Elsewhere Classified
Pulmonary Fibrosis, Unspecified
Pyoderma Gangrenosum
Radiodermatitis, Unspecified
Rapidly Progressive Nephritic Syndrome
Recurrent And Persistent Hematuria With Other Morphologic Changes
Rheumatoid Arthritis
Rheumatoid Bursitis
Rheumatoid Nodule
Rosacea
Salpingitis And Oophoritis
Sarcoidosis
Scleritis
Seborrheic Dermatitis
Seborrheic Keratosis
Secondary And Unspecified Malignant Neoplasm Of Lymph Nodes
Secondary Malignant Neoplasm Of Resp And Digestive Organs
Secondary Neuroendocrine Tumors
Severe Combined Immunodeficiency [Scid] With Low Or Normal B-Cell Numbers
Sicca Syndrome [Sjogren]
Simple And Mucopurulent Chronic Bronchitis
Solar Urticaria
Stevens-Johnson Syndrome
Stomatitis And Related Lesions
Synovitis And Tenosynovitis
Systemic Mastocytosis
Systemic Sclerosis Induced By Drug And Chemical
Systemic Sclerosis, Unspecified
Thyroiditis
Thyrotoxicosis With Diffuse Goiter
Toxic Epidermal Necrolysis [Lyell]
Transplant Rejection
Type 1 Diabetes Mellitus TABLE 8-continued 250 Indications Selected by Cluster Assessment Indications Type 1 Diabetes Mellitus With Circulatory Complications
Type 1 Diabetes Mellitus With Ketoacidosis
Type 1 Diabetes Mellitus With Kidney Complications
Type 1 Diabetes Mellitus With Neurological Complications
Type 1 Diabetes Mellitus With Ophthalmic Complications
Type 1 Diabetes Mellitus With Other Specified Complications
Type 1 Diabetes Mellitus With Unspecified Complications
Type 1 Diabetes Mellitus Without Complications
Ulcerative Colitis
Unifocal Langerhans-Cell Histiocytosis
Upper Respiratory Tract Hypersensitivity Reaction, Site Unspecified
Urticaria
Vernal Conjunctivitis
Vitiligo
Vogt-Koyanagi Syndrome The list of 86 indications (Table 9) was further characterized by clinical and commercial feasibility: among them several didn't represent an as-yet distinct clinical diagnosis or had poorly understood clinical rationale for IL-4/IL-13 modulation and others didn't have readily commercial assessment information. Many of the indications had already been considered by the project team as follow-on indications for Dupixent®.

TABLE 9

Indications identified and characterized by machine-learning method

| Conditions | Treatment Area |
| --- | --- |
| Upper respiratory tract hyper-sensitivity reaction, site unspecified | Respiratory |
| Anaphylaxis | Allergy |
| Other female pelvic inflammatory diseases | Gynecology |
| Chronic diseases of tonsils and adenoids | ENT |
| Hypertrophy of adenoids | ENT |
| Endometriosis | Gynecology |
| Inflammatory disease of cervix uteri | Gynecology |
| Other and unspecified allergy | Allergy |
| Other specified disorders of nose and nasal sinuses | ENT |
| Eosinophilic colitis | Gastroenterology |
| Allergic and dietetic gastroenteritis and colitis | Gastroenterology |
| Eosinophilic gastritis or gastroenteritis | Gastroenterology |
| Salpingitis and oophoritis | Gynecology |
| Acute lymphadenitis | Infectious disease |
| Nonsuppurative otitis media | ENT |
| Interstitial cystitis (chronic) | Urology |
| Carcinoma in situ of cervix uteri | Oncology |
| Allergic bronchopulmonary aspergillosis | Respiratory |
| Angioneurotic edema, initial encounter | Allergy |
| Chronic tubulo-interstitial nephritis | Renal |
| Acute sinusitis | Respiratory |
| Eosinophilia | Rheumatology |
| Allergic rhinitis | Allergy |
| Polyarteritis nodosa and related conditions | Rheumatology |
| Hyperimmunoglobulin E [IgE] syndrome | Immunology |
| Myositis | Rheumatology |
| Postinfective and reactive arthropathies | Rheumatology |
| Acne | Dermatology |
| Erythema multiforme | Dermatology |
| Pityriasis Rosea | Dermatology |
| Vernal conjunctivitis | Allergy |
| Epidermolysis bullosa | Dermatology |
| Eczematous dermatitis of eyelid | Dermatology |
| Allergic dermatitis of eyelid | Dermatology |
| Systemic mastocytosis | Hematology |
| Hemangioma of skin and subcutaneous tissue | Dermatology |
| Dyshidrosis [pompholyx] | Dermatology |
| Lichen planus | Dermatology |
| Dermatitis herpetiformis | Dermatology |
| Rosacea | Dermatology |

TABLE 9-continued

Indications identified and characterized by machine-learning method

| Conditions | Treatment Area |
| --- | --- |
| Cicatricial alopecia [scarring hair loss] | Dermatology |
| Otosclerosis | ENT |
| Severe combined immunodeficiency [SCID] with low or normal b-cell numbers | Immunology |
| Melanocytic nevi | Dermatology |
| Granuloma faciale [eosinophilic granuloma of skin] | Dermatology |
| Exfoliative dermatitis | Dermatology |
| Other specified dermatitis | Dermatology |
| Eccrine sweat disorders | Dermatology |
| Seborrheic dermatitis | Dermatology |
| Chronic giant papillary conjunctivitis | Allergy |
| Dermatitis, unspecified | Dermatology |
| Scleritis | Rheumatology |
| Solar urticaria | Dermatology |
| Other respiratory conditions due to chemicals, gases, fumes and vapors | Respiratory |
| Pruritus | Dermatology |
| Vitiligo | Dermatology |
| Chronic rhinitis, nasopharyngitis and pharyngitis | Respiratory |
| Erythema nodosum | Dermatology |
| Other phakomatoses, not elsewhere classified | Dermatology |
| Stevens-Johnson syndrome | Dermatology |
| Other specified systemic involvement of connective tissue | Rheumatology |
| Pyoderma gangrenosum | Dermatology |
| Felty's syndrome | Rheumatology |
| Graft-versus-host disease | Hematology |
| Adult-onset Still's disease | Rheumatology |
| Other specified disorders involving the immune mechanism, not elsewhere classified | Immunology |
| Monocytic leukemia | Oncology |
| Myeloid leukemia_general | Oncology |
| Mastoiditis and related conditions | ENT |
| Extrinsic allergic alveolitis | Respiratory |
| Chronic myeloproliferative disease | Oncology |
| Simple and mucopurulent chronic bronchitis | Respiratory |
| Recurrent and persistent hematuria with other morphologic changes | Renal |
| Multiple sclerosis | Neurology |
| Juvenile rheumatoid arthritis | Rheumatology |
| Vogt-koyanagi syndrome | Neurology |
| Thyrotoxicosis with diffuse goiter | Endocrinology |
| Ulcerative colitis | Gastroenterology |
| Amyotrophic lateral sclerosis | Neurology |
| Malignant neoplasm of breast | Oncology |
| Autoimmune thyroiditis | Endocrinology |
| Chronic nasopharyngitis | Respiratory |
| Neuromyelitis optica [Devic] | Neurology |
| Carcinoma in situ of breast | Oncology |
| Malignant neoplasm of prostate | Oncology |
| Otitis externa | ENT |

Example 2: Extension of Drug Repurposing to Patients that have a "Dupilumab-Like" Patient Profile In Example 1, a real world-data (RWD)-driven approach to identify novel indications in the IL-4/IL-13 pathway was performed on a group of about 17 million subjects ("Group I"). To confirm that the 86 indications identified in Example 1 are representative of indications identified when a drug known to target the IL-4/IL-13 pathway is used as the referential, a larger population cohort ("Group II") was created using the same criteria as Example 1, and using data from Optum Humedica from 2014-2019, which includes one additional year of patients. This cohort included 19 million patients. Dupilumab (Dupixent®) targets the IL-4/IL-13 pathway and is approved in the US and Europe for the treatment of atopic dermatitis, asthma and chronic rhinosinusitis with nasal polyposis. Compared to Example 1 (i.e. Group I), Group II included more subjects treated with dupilumab (identified with a "dupi-treated" flag), due to the additional year of data available. This second study aimed to answer the question "What level of support do we have for the 86 indications identified in the study of Example 1, when the referential is a dupilumab treated patient profile?"

Figure 8:
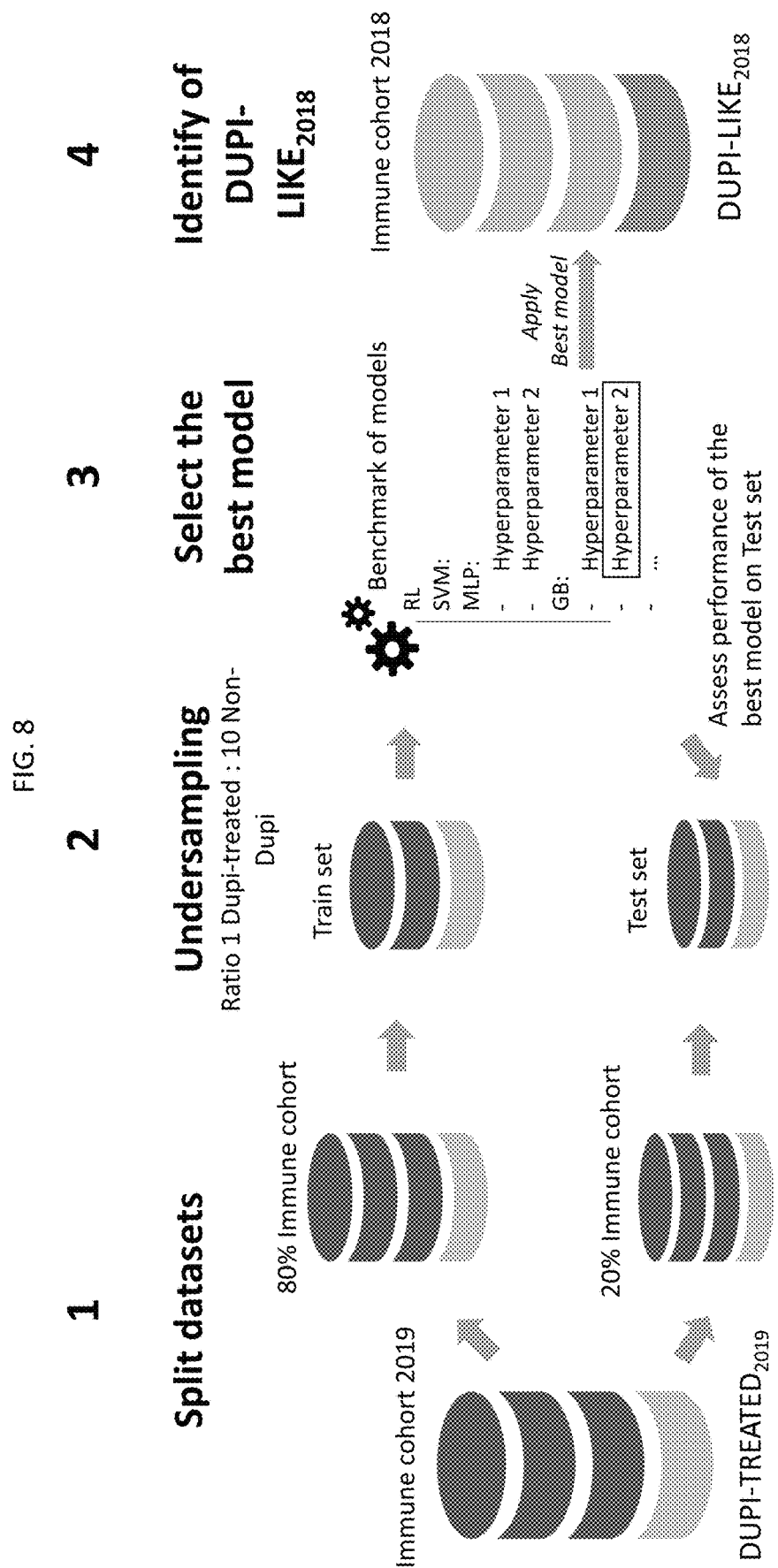
FIG. 8 is a description of the machine-based learning method to create a dupi-like flag cohort.

To generate a cohort to represent dupilumab-treated or dupilumab-eligible or potentially eligible patients, a machine learning method was used to flag "dupilumab like" (i.e., "dupi-like") patients. The cohort of subjects in Group II was split into two datasets: one with 80% of the cohort, to make a training set, and another with 20% of the cohort, to make a testing set (see FIG. 8). In each dataset, subjects with a "dupi-treated" flag served as positive controls. The subjects without a dupi-treated flag ("dupi-not-treated") in each dataset (80% of the cohort and 20% of the cohort) were randomly removed until the "dupi-not-treated":"dupi-treated" ratio was 10:1. Predictive models were trained on the 80% cohort to predict a "dupi-like" patient profile, using MCA components defined based on 2,500 of the 2,700 features from Example 1.

After selecting the best model and hyperparameters that achieved a "best predictive model," the identified "best predictive model" was tested on the remaining 20% of the cohort. In the remaining 20% of the cohort test dataset, the model predicted "dupi-not-treated" subjects just as likely to be receptive to dupilumab as "dupi-treated" subjects (i.e. Recall is 0.7 and precision is 0.4 for sensitive not precise threshold 0.1). Using this "best predictive model," a "dupi-like" flag was produced in the cohort of 17 million patients from Example 1 (Group I). Using the "dupi-like" flag, the list of 250 indications provided in Example 1 were re-ranked to identify a list of top 30 indications based on co-occurrence with the "dupi-like" flag ("the dupi-like indications list") (see Table 9).

Example 3: Comparison of Indications Identified in Example 1 and Indications Identified in Example 2

Example 1 provided a list of 86 indications that would be predicted to be receptive to dupilumab. Example 2 provided a list of 30 indications that would be predicted to be receptive to dupilumab (see Table 10). As shown in Table 10, 24 of the top 30 ranked indications overlap with the top 30 ranked indications in the four referential groups utilized in Example 1, suggesting that each strategy provides a consistent list of indications that would be receptive to treatment with an IL-4 inhibitor such as dupilumab.

TABLE 10

Overlap of indications from Example 1 and Example 2

| Feature | Top 30 ranked indications for "dupi-like" referential (Example 2) | | Overlapping top 30 ranked indications for each 4 referentials from Example 1 | | | |
|---|---|---|---|---|---|---|
| | "dupi-like" threshold $0.5^a$ ranking top30 | "dupi-like" threshold $0.1^b$ ranking top30 | Asthma ranking top30 | Atopic dermatitis ranking top30 | IgE ranking top30 | Immune ranking top30 |
| UPPER RESPIRATORY TRACT HYPERSENSITIVITY REACTION, SITE UNSPECIFIED | 1 | 1 | 1 | | 1 | 1 |
| NONSUPPURATIVE OTITIS MEDIA | 1 | 1 | 1 | | 1 | 1 |
| Vernal conjunctivitis | 1 | 1 | | 1 | | 1 |
| SEVERE COMBINED IMMUNODEFICIENCY [SCID] WITH LOW OR NORMAL B-CELL NUMBERS | 1 | 1 | | 1 | 1 | |
| SYSTEMIC MASTOCYTOSIS | 1 | 1 | | 1 | 1 | |
| ALLERGIC AND DIETETIC GASTROENTERITIS AND COLITIS | 1 | 1 | 1 | | 1 | |
| EOSINOPHILIC GASTRITIS OR GASTROENTERITIS | 1 | 1 | 1 | | 1 | |
| HYPERIMMUNOGLOBULIN E [IGE] SYNDROME | 1 | 1 | 1 | | 1 | |
| EOSINOPHILIC COLITIS | 1 | 1 | 1 | | 1 | |
| OTHER SPECIFIED DISORDERS INVOLVING THE IMMUNE MECHANISM, NOT ELSEWHERE CLASSIFIED | 1 | 1 | | | 1 | |
| POSTINFECTIVE AND REACTIVE ARTHROPATHIES | 1 | 1 | | | 1 | |
| OTHER SPECIFIED SYSTEMIC INVOLVEMENT OF CONNECTIVE TISSUE | 1 | 1 | | | 1 | |
| ERYTHEMA MULTIFORME | 1 | 1 | | | 1 | |
| ERYTHEMA NODOSUM | 1 | 1 | | | 1 | |

TABLE 10-continued

Overlap of indications from Example 1 and Example 2

| | Top 30 ranked indications for "dupi-like" referential (Example 2) | | Overlapping top 30 ranked indications for each 4 referentials from Example 1 | | | |
|---|---|---|---|---|---|---|
| Feature | "dupi-like" threshold 0.5[a] ranking top30 | "dupi-like" threshold 0.1[b] ranking top30 | Asthma ranking top30 | Atopic dermatitis ranking top30 | IgE ranking top30 | Immune ranking top30 |
| HEMANGIOMA OF SKIN AND SUBCUTANEOUS TISSUE | 1 | 1 | | 1 | | |
| CICATRICIAL ALOPECIA [SCARRING HAIR LOSS] | 1 | 1 | | 1 | | |
| ECCRINE SWEAT DISORDERS | 1 | 1 | | 1 | | |
| DERMATITIS HERPETIFORMIS | 1 | 1 | | 1 | | |
| EXFOLIATIVE DERMATITIS | 1 | 1 | | 1 | | |
| EPIDERMOLYSIS BULLOSA | 1 | 1 | | 1 | | |
| PRURITUS | 1 | 1 | | 1 | | |
| ROSACEA | 1 | 1 | | 1 | | |
| DIFFUSE (EOSINOPHILIC) FASCIITIS | 1 | 1 | | | | |
| PNEUMOCONIOSIS DUE TO DUST CONTAINING SILICA | 1 | 1 | | | | |
| THYROIDITIS | 1 | 1 | | | | |
| KERATITIS | 1 | 1 | | | | |
| Atopic Conjunctivitis | 1 | | | | | 1 |
| ALLERGIC DERMATITIS OF EYELID | 1 | | | 1 | | |
| CHRONIC RHINITIS, NASOPHARYNGITIS AND PHARYNGITIS | 1 | | | | | |
| CHRONIC NASOPHARYNGITIS | 1 | | | | | |
| ANGIONEUROTIC EDEMA, INITIAL ENCOUNTER | | 1 | 1 | | 1 | |
| ADULT-ONSET STILL'S DISEASE | | 1 | | | 1 | |
| SICCA SYNDROME [SJOGREN] | | 1 | | | | |
| ARTHROPATHIC PSORIASIS | | 1 | | | | |

[a] A dupi-like threshold of 0.5 indicates a referential that included a less permissive cohort, which would include permissive predicted dupi-like patients.
[b] A dupi-like threshold of 0.1 indicates a test set that included a more permissive cohort, which would include more predicted dupi-like patients.

OTHER ASPECTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of treating a subject with an anti-interleukin-4 receptor alpha (anti-IL-4Rα) antibody, comprising administering a therapeutically effective amount of an anti-IL-4Rα antibody to a subject exhibiting at least one symptom of a disorder selected from the group consisting of an esophageal-related disorder, a lung-related disorder, a blood-related disorder, a gastrointestinal-related disorder, a kidney-related disorder, a prostate-related disorder, Kawasaki's disease, a thyroid-related disorder, a blood-vessel-related disorder, a pregnancy-related disorder, and a cancer,
   wherein the anti-IL-4Rα antibody comprises:
   a variable heavy chain CDR1 of SEQ ID NO:1 (GFTFRDYA);
   a variable heavy chain CDR2 of SEQ ID NO:2 (ISGSGGNT);
   a variable heavy chain CDR3 of SEQ ID NO:3 (AKDRLSITIRPRYYGLDV);
   a variable light chain CDR1 of SEQ ID NO:4 (QSLLYSIGYNY);
   a variable light chain CDR2 of SEQ ID NO:5 (LGS); and
   a variable light chain CDR3 of SEQ ID NO:6 (MQALQTPYT).

2. The method of claim 1, wherein the anti-IL-4Rα antibody comprises a heavy chain variable region (VH) comprising the amino acid sequence of SEQ ID NO:13 and a light chain variable region (VL) comprising the amino acid sequence of SEQ ID NO:14.

3. The method of claim 1, wherein the subject is human.

4. The method of claim 1, wherein the administering is selected from:
   (a) intradermal, intramuscular, intraperitoneal, intravenous, subcutaneous, intranasal, or epidural administration;
   (b) via a pre-filled syringe;
   (c) via a pre-filled pen; or
   (d) via an autoinjector.

5. The method of claim 1, wherein the anti-IL-4Rα antibody is administered over multiple doses.

6. The method of claim 1, wherein the anti-IL-4Rα antibody is administered at a dose of about 0.0001 to about 10 mg/kg of patient body weight.

7. The method of claim 1, further comprising administering a second therapeutic agent selected from a second antibody or antigen binding fragment thereof, a soluble cytokine receptor, an IgE antagonist, or an anti-asthma medication,
   wherein the anti-asthma medication is a corticosteroid, a non-steroidal agent, a beta agonist, a leukotriene antagonist, a xanthine, fluticasone, salmeterol, or albuterol.

8. The method of claim 1, wherein the lung-related disorder is lung fibrosis.

9. The method of claim 1, wherein the lung-related disorder is lung cirrhosis.

10. The method of claim 1, wherein the lung-related disorder is chronic fibrotic lung disease.

11. The method of claim 1, wherein the lung-related disorder is cystic fibrosis.

12. The method of claim 1, wherein the lung-related disorder is bleomycin-induced pneumopathy and fibrosis.

13. The method of claim 1, wherein the lung-related disorder is pulmonary alveolar proteinosis.

14. The method of claim 1, wherein the lung-related disorder is adult respiratory distress syndrome.

15. The method of claim 1, wherein the lung-related disorder is sarcoidosis.

16. The method of claim 1, wherein the lung-related disorder is tuberculosis.

17. The method of claim 1, wherein the lung-related disorder is aspirin-exacerbated respiratory disease.

18. The method of claim 1, wherein the blood-related disorder is sickle cell disease.

19. The method of claim 1, wherein the blood-related disorder is Churg-Strauss syndrome.

20. The method of claim 1, wherein the blood-related disorder is autoimmune lymphoproliferative syndrome.

21. The method of claim 1, wherein the blood-related disorder is systemic lupus erythematosus.

22. The method of claim 1, wherein the blood-related disorder is antiphospholipid antibody syndrome (APS).

23. The method of claim 1, wherein the blood-related disorder is autoimmune hemolytic anemia.

24. The method of claim 1, wherein the esophageal-related disorder is Barrett's esophagus.

25. The method of claim 1, wherein the esophageal-related disorder is eosinophilic gastritis.

26. The method of claim 1, wherein the esophageal-related disorder is achalasia.

27. The method of claim 1, wherein the esophageal-related disorder is gastroesophageal reflux disease (GERD).

28. The method of claim 1, wherein the gastrointestinal-related disorder is ulcerative colitis.

29. The method of claim 1, wherein the gastrointestinal-related disorder is Whipple's disease.

30. The method of claim 1, wherein the gastrointestinal-related disorder is Behçet's disease.

31. The method of claim 1, wherein the gastrointestinal-related disorder is Wegener granulomatosis.

32. The method of claim 1, wherein the kidney-related disorder is nephrosis.

33. The method of claim 1, wherein the kidney-related disorder is glomerulonephritis.

34. The method of claim 1, wherein the kidney-related disorder is Goodpasture syndrome.

35. The method of claim 1, wherein the prostate-related disorder is benign prostrate hyperplasia.

36. The method of claim 1, wherein the prostate-related disorder is chronic prostatitis syndrome.

37. The method of claim 1, wherein the disorder is Kawasaki's disease.

38. The method of claim 1, wherein the pregnancy-related disorder is pre-eclampsia.

39. The method of claim 1, wherein the pregnancy-related disorder is antiphospholipid syndrome.

40. The method of claim 1, wherein the pregnancy-related disorder is immune thrombocytopenia.

41. The method of claim 1, wherein the cancer is a cutaneous T-cell lymphoma.

42. The method of claim 1, wherein the administering is via a pre-filled syringe.

43. The method of claim 1, wherein the administering is via a pre-filled pen.

44. The method of claim 1, wherein the administering is via an autoinjector.

45. The method of claim 1, wherein the anti-IL-4Rα antibody is administered to the subject as an initial dose followed by one or more secondary doses.

46. The method of claim 45, wherein the initial dose is about 600 mg and each secondary dose is about 300 mg.

47. The method of claim 45, wherein the initial dose is about 400 mg and each secondary dose is about 200 mg.

48. The method of claim 45, wherein each secondary dose is administered every 2 weeks.

\* \* \* \* \*

UNITED STATES PATENT AND TRADEMARK OFFICE
CERTIFICATE OF CORRECTION

PATENT NO. : 11,723,974 B2  
APPLICATION NO. : 17/115618  
DATED : August 15, 2023  
INVENTOR(S) : Paul Bryce et al.

Page 1 of 1

It is certified that error appears in the above-identified patent and that said Letters Patent is hereby corrected as shown below:

On the Title Page

Item (73) Assignee, delete "Sanofi-Aventis Biotechnology," and insert -- Sanofi Biotechnology --

Signed and Sealed this
Twenty-seventh Day of January, 2026

John A. Squires
*Director of the United States Patent and Trademark Office*

SEQUENCE LISTING

<160> NUMBER OF SEQ ID NOS: 19

<210> SEQ ID NO 1
<211> LENGTH: 8
<212> TYPE: PRT
<213> ORGANISM: Artificial Sequence
<220> FEATURE:
<223> OTHER INFORMATION: part of peptide that binds IL-4R
<220> FEATURE:

```
<221> NAME/KEY: MISC_FEATURE
<223> OTHER INFORMATION: Anti-IL-4R-alpha HC CDR1

<400> SEQUENCE: 1

Gly Phe Thr Phe Arg Asp Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: part of peptide that binds IL-4R
<220> FEATURE:
<221> NAME/KEY: MISC_FEATURE
<223> OTHER INFORMATION: Anti-IL-4R-alpha HC CDR2

<400> SEQUENCE: 2

Ile Ser Gly Ser Gly Gly Asn Thr
1               5

<210> SEQ ID NO 3
<211> LENGTH: 18
<212> TYPE: PRT
<213> ORGANISM: Artificial Sequence
<220> FEATURE:
<223> OTHER INFORMATION: part of peptide that binds IL-4R
<220> FEATURE:
<221> NAME/KEY: MISC_FEATURE
<223> OTHER INFORMATION: Anti-IL-4R-alpha HC CDR3

<400> SEQUENCE: 3

Ala Lys Asp Arg Leu Ser Ile Thr Ile Arg Pro Arg Tyr Tyr Gly Leu
1               5                   10                  15

Asp Val

<210> SEQ ID NO 4
<211> LENGTH: 11
<212> TYPE: PRT
<213> ORGANISM: Artificial Sequence
<220> FEATURE:
<223> OTHER INFORMATION: part of peptide that binds IL-4R
<220> FEATURE:
<221> NAME/KEY: MISC_FEATURE
<223> OTHER INFORMATION: Anti-IL-4R-alpha LC CDR1

<400> SEQUENCE: 4

Gln Ser Leu Leu Tyr Ser Ile Gly Tyr Asn Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: part of peptide that binds IL-4R
<220> FEATURE:
<221> NAME/KEY: MISC_FEATURE
<223> OTHER INFORMATION: Anti-IL-4R-alpha LC CDR2

<400> SEQUENCE: 5

Leu Gly Ser
1

<210> SEQ ID NO 6
<211> LENGTH: 9
<212> TYPE: PRT
<213> ORGANISM: Artificial Sequence
```

```
<220> FEATURE:
<223> OTHER INFORMATION: part of peptide that binds IL-4R
<220> FEATURE:
<221> NAME/KEY: MISC_FEATURE
<223> OTHER INFORMATION: Anti-IL-4R-alpha LC CDR3

<400> SEQUENCE: 6

Met Gln Ala Leu Gln Thr Pro Tyr Thr
1               5

<210> SEQ ID NO 7
<211> LENGTH: 24
<212> TYPE: DNA
<213> ORGANISM: Artificial Sequence
<220> FEATURE:
<223> OTHER INFORMATION: part of peptide that binds IL-4R
<220> FEATURE:
<221> NAME/KEY: misc_feature
<223> OTHER INFORMATION: Anti-IL-4R-alpha HC CDR1

<400> SEQUENCE: 7
ggattcacct ttagagacta tgcc                                            24

<210> SEQ ID NO 8
<211> LENGTH: 24
<212> TYPE: DNA
<213> ORGANISM: Artificial Sequence
<220> FEATURE:
<223> OTHER INFORMATION: part of peptide that binds IL-4R
<220> FEATURE:
<221> NAME/KEY: misc_feature
<223> OTHER INFORMATION: Anti-IL-4R-alpha HC CDR2

<400> SEQUENCE: 8
attagtggtt ccggtggtaa caca                                            24

<210> SEQ ID NO 9
<211> LENGTH: 54
<212> TYPE: DNA
<213> ORGANISM: Artificial Sequence
<220> FEATURE:
<223> OTHER INFORMATION: part of peptide that binds IL-4R
<220> FEATURE:
<221> NAME/KEY: misc_feature
<223> OTHER INFORMATION: Anti-IL-4R-alpha HC CDR3

<400> SEQUENCE: 9
gcgaaagatc gactctctat aacaattcgc ccacgctatt atggtttgga cgtc           54

<210> SEQ ID NO 10
<211> LENGTH: 33
<212> TYPE: DNA
<213> ORGANISM: Artificial Sequence
<220> FEATURE:
<223> OTHER INFORMATION: part of peptide that binds IL-4R
<220> FEATURE:
<221> NAME/KEY: misc_feature
<223> OTHER INFORMATION: Anti-IL-4R-alpha LC CDR1

<400> SEQUENCE: 10
cagagcctcc tgtatagtat tggatacaac tat                                  33

<210> SEQ ID NO 11
<211> LENGTH: 9
<212> TYPE: DNA
<213> ORGANISM: Artificial Sequence
<220> FEATURE:
<223> OTHER INFORMATION: part of peptide that binds IL-4R
<220> FEATURE:
```

-continued

```
<221> NAME/KEY: misc_feature
<223> OTHER INFORMATION: Anti-IL-4R-alpha LC CDR2

<400> SEQUENCE: 11 ttgggttct                                                                9

<210> SEQ ID NO 12
<211> LENGTH: 27
<212> TYPE: DNA
<213> ORGANISM: Artificial Sequence
<220> FEATURE:
<223> OTHER INFORMATION: part of peptide that binds IL-4R
<220> FEATURE:
<221> NAME/KEY: misc_feature
<223> OTHER INFORMATION: Anti-IL-4R-alpha LC CDR3

<400> SEQUENCE: 12
atgcaagctc tacaaactcc gtacact                                           27

<210> SEQ ID NO 13
<211> LENGTH: 124
<212> TYPE: PRT
<213> ORGANISM: Artificial Sequence
<220> FEATURE:
<223> OTHER INFORMATION: part of peptide that binds IL-4R
<220> FEATURE:
<221> NAME/KEY: MISC_FEATURE
<223> OTHER INFORMATION: Anti-IL-4R-alpha Heavy chain variable region

<400> SEQUENCE: 13

Glu Val Gln Leu Val Glu Ser Gly Gly Gly Leu Glu Gln Pro Gly Gly
1               5                  10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 14
<211> LENGTH: 112
<212> TYPE: PRT
<213> ORGANISM: Artificial Sequence
<220> FEATURE:
<223> OTHER INFORMATION: part of peptide that binds IL-4R
<220> FEATURE:
<221> NAME/KEY: MISC_FEATURE
<223> OTHER INFORMATION: Anti-IL-4R-alpha Light chain variable region

<400> SEQUENCE: 14

Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu Tyr Ser
            20                  25                  30

Ile Gly Tyr Asn Ty

```
                  35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 15
<211> LENGTH: 372
<212> TYPE: DNA
<213> ORGANISM: Artificial Sequence
<220> FEATURE:
<223> OTHER INFORMATION: part of peptide that binds IL-4R
<220> FEATURE:
<221> NAME/KEY: misc_feature
<223> OTHER INFORMATION: Anti-IL-4R-alpha Heavy chain variable region

<400> SEQUENCE: 15
gaggtgcagc tggtggagtc tgggggaggc ttggaacagc cggggggtc cctgagactc      60 tcctgtgcag gctctggatt caccttaga gactatgcca tgacctgggt ccgccaggct     120
ccagggaagg gactgagtg gtctcatct attagtggtt ccgtggtaa cacatactac       180 gcagactccg tgaagggccg gttcaccatc tccagagaca attccaagaa cacgctgtat    240
ctgcaaatga acagcctgag agccgaggac acggccgtat attactgtgc gaaagatcga    300
ctctctataa caattcgccc acgctattat ggtttggacg tctggggcca agggaccacg    360
gtcaccgtct cc                                                         372

<210> SEQ ID NO 16
<211> LENGTH: 336
<212> TYPE: DNA
<213> ORGANISM: Artificial Sequence
<220> FEATURE:
<223> OTHER INFORMATION: part of peptide that binds IL-4R
<220> FEATURE:
<221> NAME/KEY: misc_feature
<223> OTHER INFORMATION: Anti-IL-4R-alpha Light chain variable region

<400> SEQUENCE: 16
gacatcgtga tgacccagtc tccactctcc ctgcccgtca cccctggaga gccggcctcc      60
atctcctgca ggtctagtca gagcctcctg tatagtattg atacaacta tttggattgg      120 tacctgcaga agtcagggca gtctccacag ctccttatct atttgggttc taatcgggcc     180
tccggggtcc ctgacaggtt cagtggcagt ggatcaggca cagattttac actgaaaatc     240
agcagagtgg aggctgagga tgttgggttt tattactgca tgcaagctct acaaactccg     300
tacacttttg gccaggggac caagctggag atcaaa                              336

<210> SEQ ID NO 17
<211> LENGTH: 451
<212> TYPE: PRT
<213> ORGANISM: Artificial Sequence
<220> FEATURE:
<223> OTHER INFORMATION: part of peptide that binds IL-4R
<220> FEATURE:
<221> NAME/KEY: MISC_FEATURE
<223> OTHER INFORMATION: Anti-IL-4R-alpha Heavy Chain

<400> SEQUENCE: 17
```

```
Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Lys Thr Tyr Thr Cys
    195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

Gln Glu Asp Pro Glu Val Gln Phe Asn Trp Tyr Val Asp Gly Val Glu
    275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Gln Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
```

```
                    420                 425                 430
Met His Glu Ala Leu His Asn His Tyr Thr Gln Lys Ser Leu Ser Leu
            435                 440                 445

Ser Leu Gly
    450

<210> SEQ ID NO 18
<211> LENGTH: 219
<212> TYPE: PRT
<213> ORGANISM: Artificial Sequence
<220> FEATURE:
<223> OTHER INFORMATION: part of peptide that binds IL-4R
<220> FEATURE:
<221> NAME/KEY: MISC_FEATURE
<223> OTHER INFORMATION: Anti-IL-4R-alpha Light Chain

<400> SEQUENCE: 18

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 19
<211> LENGTH: 207
<212> TYPE: PRT
<213> ORGANISM: Homo sapiens
<220> FEATURE:
<221> NAME/KEY: MISC_FEATURE
<223> OTHER INFORMATION: Human IL-4R

<400> SEQUENCE: 19

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30
```

```
Leu Arg Leu Leu Tyr Gln Leu Val Phe Leu Leu Ser Glu Ala His Thr
    35                  40                  45
Cys Ile Pro Glu Asn Asn Gly Gly Ala Gly Cys Val Cys His Leu Leu
    50                  55                  60
Met Asp Asp Val Val Ser Ala Asp Asn Tyr Thr Leu Asp Leu Trp Ala
65                  70                  75                  80
Gly Gln Gln Leu Leu Trp Lys Gly Ser Phe Lys Pro Ser Glu His Val
             85                  90                  95
Lys Pro Arg Ala Pro Gly Asn Leu Thr Val His Thr Asn Val Ser Asp
            100                 105                 110
Thr Leu Leu Leu Thr Trp Ser Asn Pro Tyr Pro Pro Asp Asn Tyr Leu
        115                 120                 125
Tyr Asn His Leu Thr Tyr Ala Val Asn Ile Trp Ser Glu Asn Asp Pro
    130                 135                 140
Ala Asp Phe Arg Ile Tyr Asn Val Thr Tyr Leu Glu Pro Ser Leu Arg
145                 150                 155                 160
Ile Ala Ala Ser Thr Leu Lys Ser Gly Ile Ser Tyr Arg Ala Arg Val
            165                 170                 175
Arg Ala Trp Ala Gln Cys Tyr Asn Thr Thr Trp Ser Glu Trp Ser Pro
        180                 185                 190
Ser Thr Lys Trp His Asn Ser Tyr Arg Glu Pro Phe Glu Gln His
        195                 200                 205
```